US012384850B2

(12) United States Patent
Zhu et al.

(10) Patent No.: US 12,384,850 B2
(45) **Date of Patent: *Aug. 12, 2025**

(54) GUIDANCE AND NAVIGATION CONTROL PROTEINS AND METHOD OF MAKING AND USING THEREOF

(71) Applicants: SYSTIMMUNE, INC., Redmond, WA (US); SICHUAN BAILI PHARMACEUTICAL CO. LTD., Chengdu (CN)

(72) Inventors: Yi Zhu, Chengdu (CN); Ole Olsen, Everett, WA (US); Dong Xia, Redmond, WA (US); David Jellyman, Duvall, WA (US); Katrina Bykova, Seattle, WA (US); Anne-Marie K. Rousseau, Seattle, WA (US); Bill Brady, Bothell, WA (US); Blair Renshaw, Renton, WA (US); Brian Kovacevich, Snohomish, WA (US); Yu Liang, Redmond, WA (US); Camilla Wang, Sammamish, WA (US); Zeren Gao, Redmond, WA (US)

(73) Assignee: SYSTIMMUNE, INC., Redmond, WA (US)

(*) Notice: Subject to any disclaimer, the term of this patent is extended or adjusted under 35 U.S.C. 154(b) by 33 days.

This patent is subject to a terminal disclaimer.

(21) Appl. No.: 16/615,124

(22) PCT Filed: Jun. 22, 2018

(86) PCT No.: PCT/US2018/039160

§ 371 (c)(1),
(2) Date: Nov. 19, 2019

(87) PCT Pub. No.: WO2019/005641

PCT Pub. Date: Jan. 3, 2019

(65) Prior Publication Data

US 2022/0002425 A1 Jan. 6, 2022

Related U.S. Application Data

(60) Provisional application No. 62/648,880, filed on Mar. 27, 2018, provisional application No. 62/648,888, filed on Mar. 27, 2018, provisional application No. 62/551,032, filed on Aug. 28, 2017, provisional application No. 62/551,065, filed on Aug. 28, 2017, provisional application No. 62/551,035, filed on Aug. 28, 2017, provisional application No. 62/545,603, filed on Aug. 15, 2017, provisional application No. 62/524,553, filed on Jun. 25, 2017, provisional application No. 62/524,557, filed on Jun. 25, 2017, provisional application No. 62/524,558, filed on Jun. 25, 2017, provisional application No. 62/524,554, filed on Jun. 25, 2017.

(51) Int. Cl.

| | |
|---|---|
| ***C07K 16/28*** | (2006.01) |
| ***A61K 35/17*** | (2015.01) |
| ***A61K 39/00*** | (2006.01) |
| ***A61K 47/68*** | (2017.01) |
| ***A61K 47/69*** | (2017.01) |
| ***A61P 35/02*** | (2006.01) |

(52) U.S. Cl.

CPC .......... *C07K 16/2878* (2013.01); *A61K 35/17* (2013.01); *A61K 39/0011* (2013.01); *A61K 39/001102* (2018.08); *A61K 47/6849* (2017.08); *A61K 47/6901* (2017.08); *A61P 35/02* (2018.01); *C07K 16/2803* (2013.01); *C07K 16/2827* (2013.01); *C07K 2317/31* (2013.01)

(58) Field of Classification Search

CPC ............ C07K 16/2878; C07K 16/2803; C07K 16/2827; C07K 2317/31; A61K 47/6849; A61K 47/6901; A61P 35/02

See application file for complete search history.

(56) References Cited

U.S. PATENT DOCUMENTS 11,787,863 B2 * 10/2023 Zhu .................... C07K 16/2803 424/135.1
12,029,761 B2 * 7/2024 Zhu ...................... C12N 5/0636

(Continued)

FOREIGN PATENT DOCUMENTS

WO WO 2009/132037 A 10/2009
WO WO2016/173605 A 11/2016

(Continued)

OTHER PUBLICATIONS

Malia et al, Proteins, 2016, 84:427-434. (Year: 2016).*
Barthelemy et al, Journal of Biological Chemistry, 2008, 283:3639-3654. (Year: 2008).*
Beiboer et al, Journal of Molecular Biology, 2000, 296:833-849. (Year: 2000).*
Choi et al, 2011, Molecular Biosystems, 2011, 7:3327-3334. (Year: 2011).*

(Continued)

*Primary Examiner* — Gary B Nickol
*Assistant Examiner* — Cheom-Gil Cheong
(74) *Attorney, Agent, or Firm* — EPIMED LLC

(57) ABSTRACT

The application provides guidance and navigation control (GNC) proteins. In one embodiment, the GNC protein Comprises a T-cell binding moiety and a cancer-targeting moiety, wherein the T-cell binding moiety has a binding specificity to a T-cell receptor comprising CD3, CD28, PDL1, PD1, OX40, 4-1BB, GITR, TIGIT, TIM-3, LAG-3, CTLA4, CD40, VISTA, ICOS, BTLA, Light, NKp30, CD28H, CD27, CD226, CD96, CD112R, A2AR, CD160, CD244, CECAM1, CD200R, TNFRSF25 (DR3), or a combination thereof, and wherein the cancer targeting moiety has a binding specificity to a cancer cell receptor.

13 Claims, 12 Drawing Sheets

Specification includes a Sequence Listing.

(56) References Cited

U.S. PATENT DOCUMENTS

| | | | | |
|---|---|---|---|---|
| 2007/0036783 | A1* | 2/2007 | Humeau | A61P 31/18 530/391.1 |
| 2008/0299137 | A1 | 12/2008 | Svendsen et al. | |
| 2012/0164067 | A1 | 6/2012 | Latham et al. | |
| 2020/0157213 | A1* | 5/2020 | Zhu | C07K 16/2809 |
| 2022/0002406 | A1* | 1/2022 | Zhu | C07K 16/2827 |

FOREIGN PATENT DOCUMENTS

| | | |
|---|---|---|
| WO | WO2017/086367 | 5/2017 |
| WO | WO 2017/093408 Y | 6/2017 |
| WO | WO 2017/106383 A | 6/2017 |

OTHER PUBLICATIONS

De Genst et al, Developmental and Comparative Immunology, 2006, 30:187-98. (Year: 2006).*

Griffiths et al, The EMBO Journal, 1993, 12:725-734. (Year: 1993).*

Klimka et al, British Journal of Cancer, 2000, 83:252-260. (Year: 2000).*

Ward et al, Nature, 1989, 341:544-546. (Year: 1989).*

English translation of WO2017086367. (Year: 2017).*

* cited by examiner

FIGURE 1. GNC proteins are characterized by their composition of multiple antigen binding domains (AgBd) and linkers.
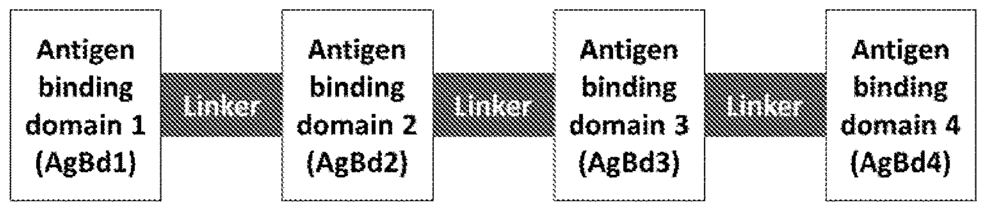

FIGURE 2. General format of a tetra-specific GNC antibody.
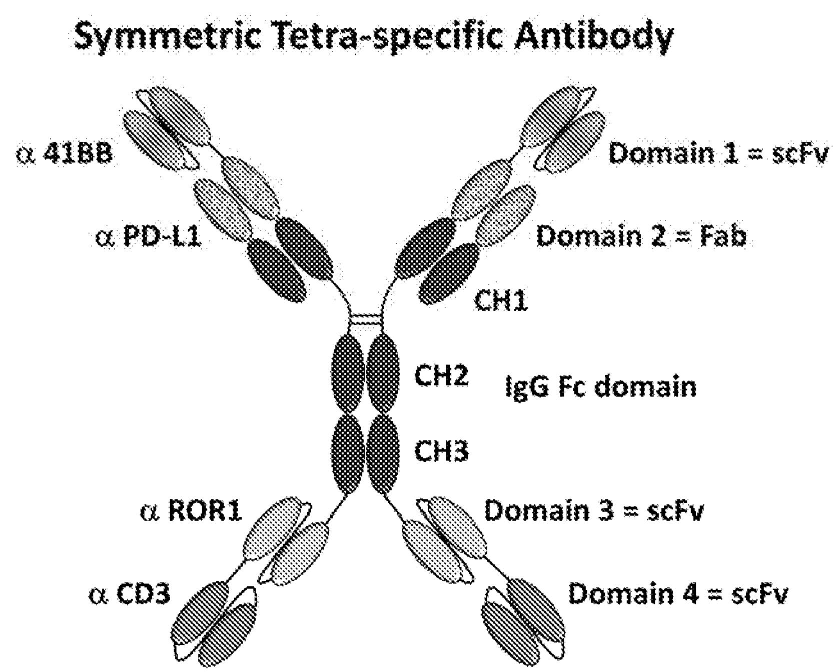

FIGURE 3. A tetra-specific GNC antibody binds to both a T cell and a tumor cell through multiple AgBds.
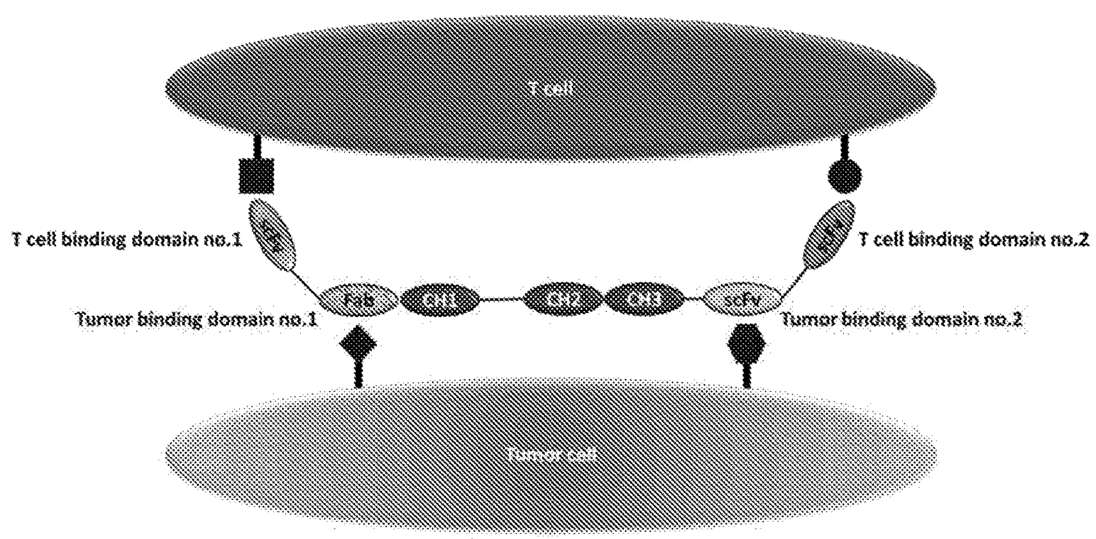

FIGURE 4. Tetra-specific GNC antibodies binding to human ROR1 transfected CHO cells.
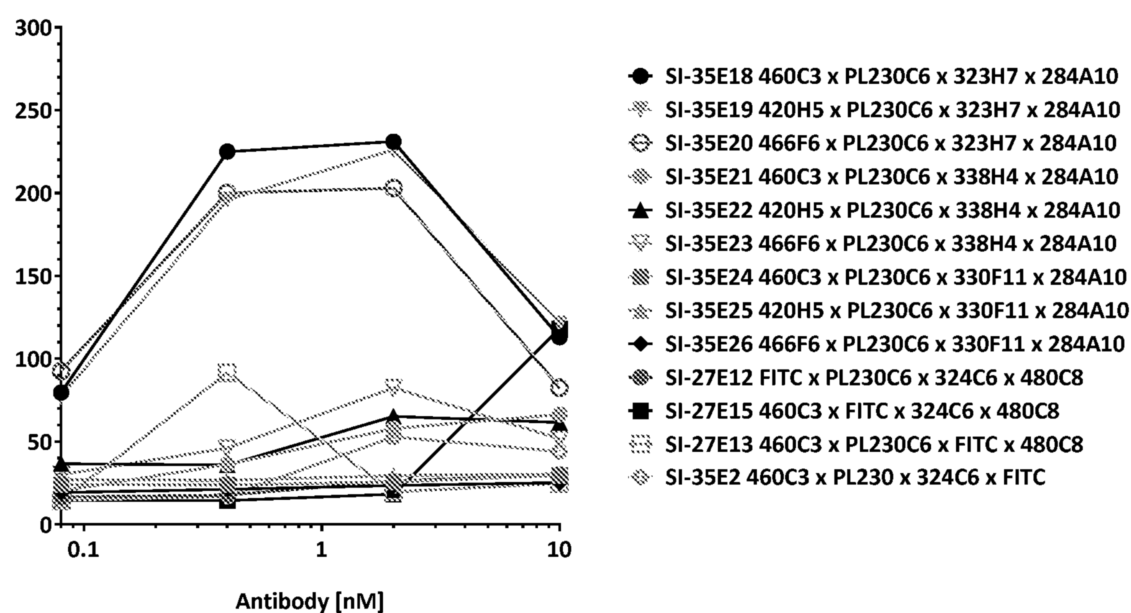

FIGURE 5. Tetra-specific GNC antibodies binding to human 41BB transfected CHO cells.
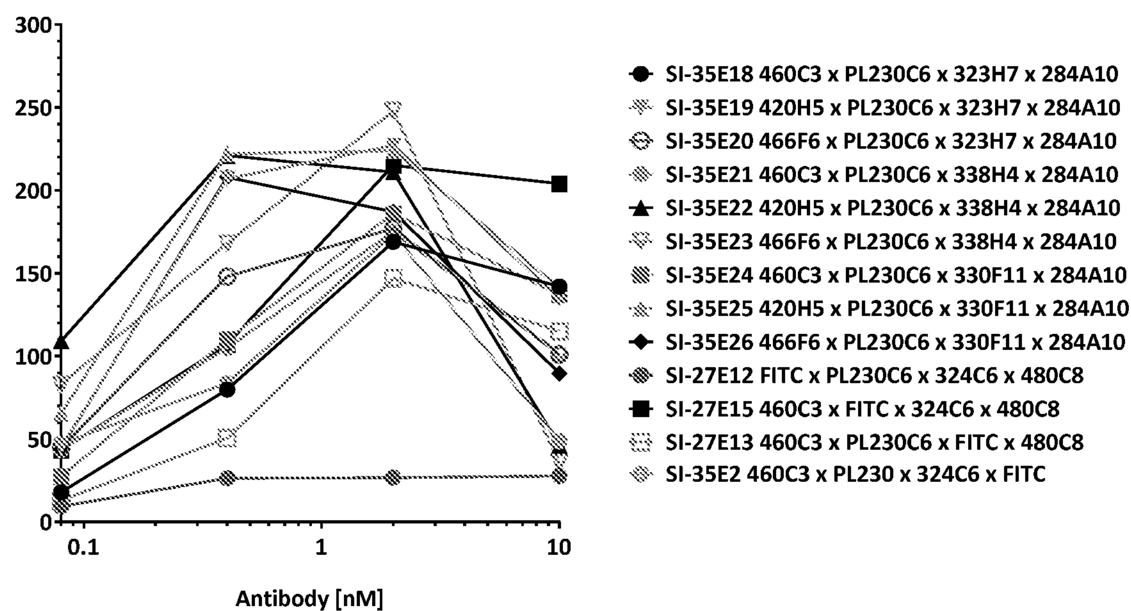

FIGURE 6. Tetra-specific GNC antibodies binding to human PD-L1 transfected CHO cells.
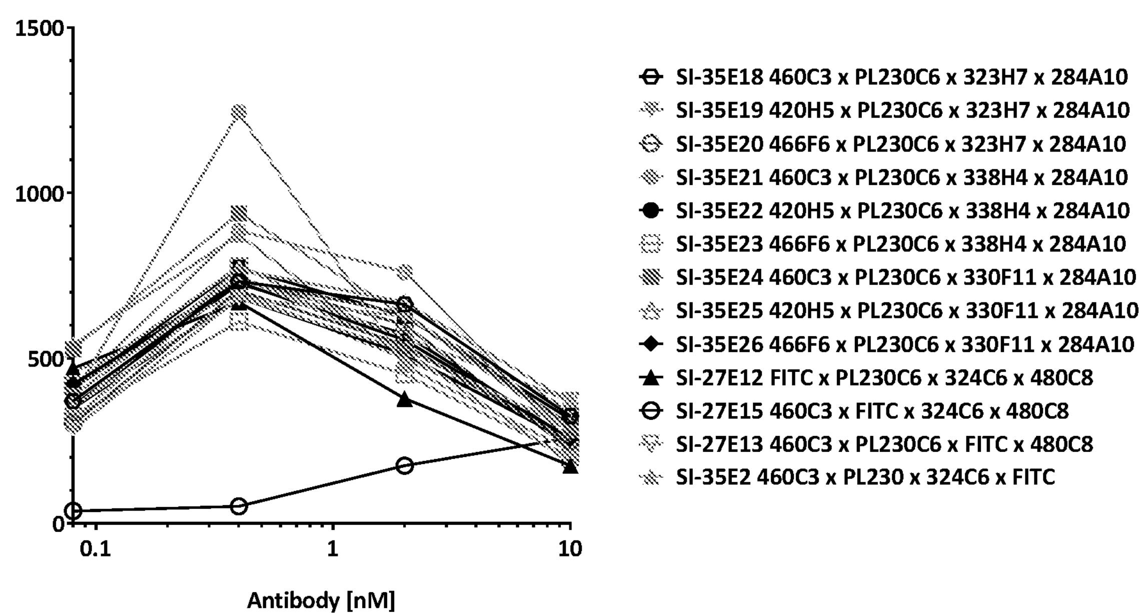

FIGURE 7. Tetra-specific GNC antibodies with the binding domain 323H7 which is specific for the Ig domain of ROR1 meditated RTCC of the B-ALL cell line Kasumi2 with PBMC as effectors.
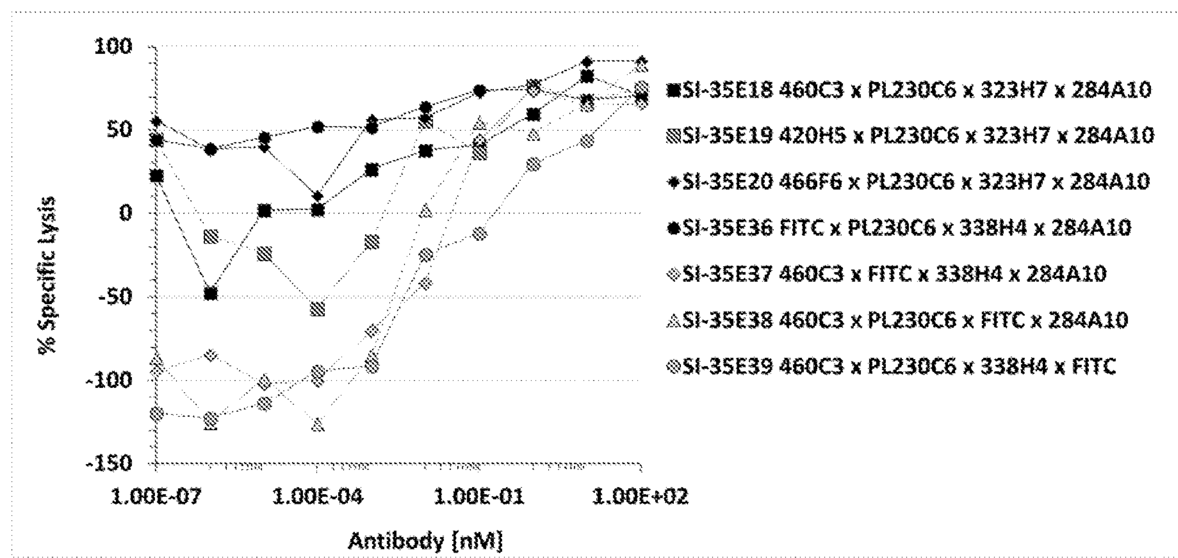

FIGURE 8. Tetra-specific GNC antibodies with the binding domain 323H7 which is specific for the Ig domain of ROR1 meditated RTCC of the B-ALL cell line Kasumi2 with CD8+, CD45RO+ memory T cells as effectors.
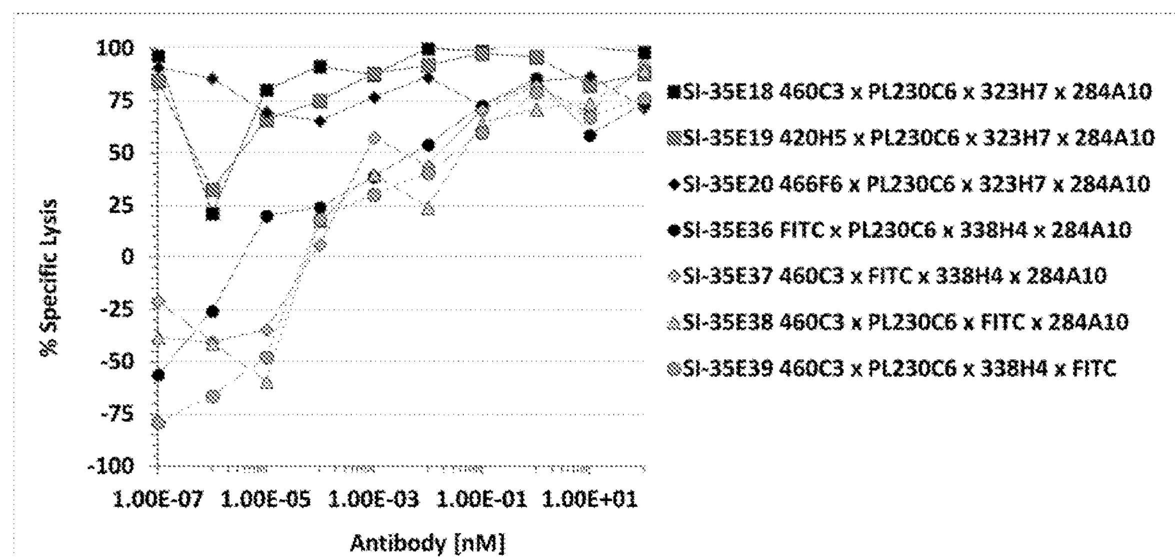

FIGURE 9. Tetra-specific GNC antibodies with the binding domain 323H7 which is specific for the Ig domain of ROR1 meditated RTCC of the B-ALL cell line Kasumi2 with CD8+, CD45RA+ naive T cells as effectors.
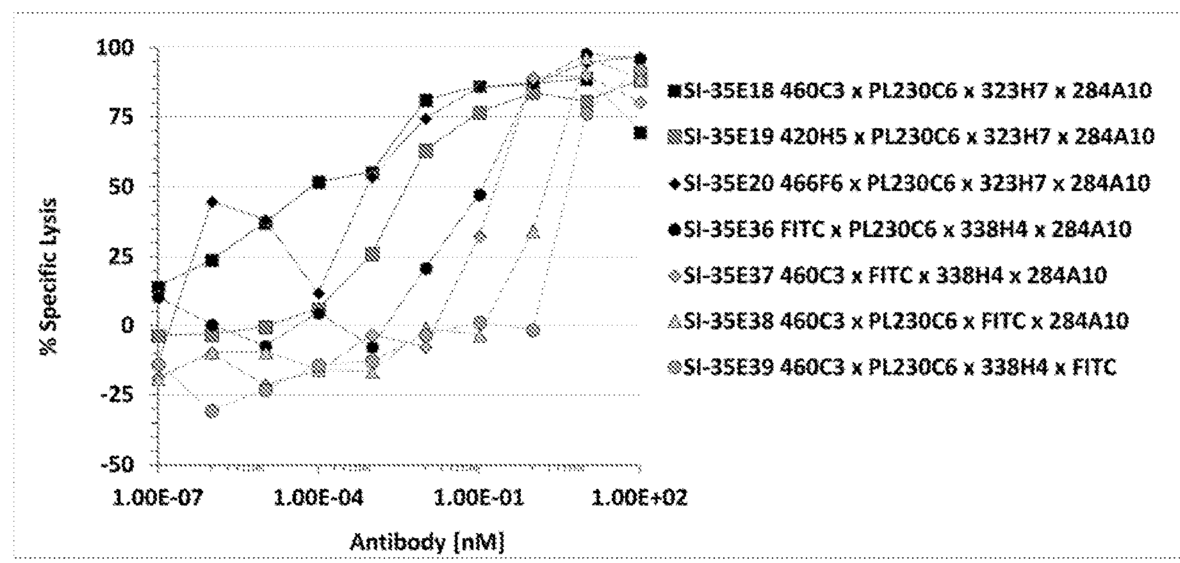

FIGURE 10. Tetra-specific GNC antibodies with the binding domain 338H4 which is specific for the Frizzled domain of ROR1 meditated RTCC of the B-ALL cell line Kasumi2 with PBMC as effectors.
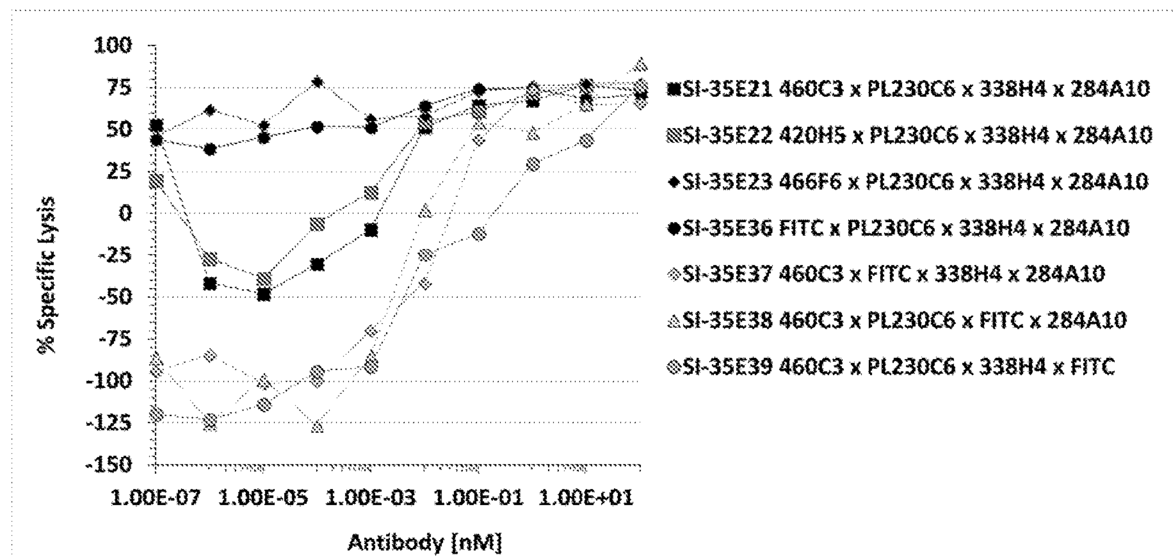

FIGURE 11. Tetra-specific antibodies with the binding domain 338H4 which is specific for the Frizzled domain of ROR1 meditated RTCC of the B-ALL cell line Kasumi2 with CD8+, CD45RO+ memory T cells as effectors.
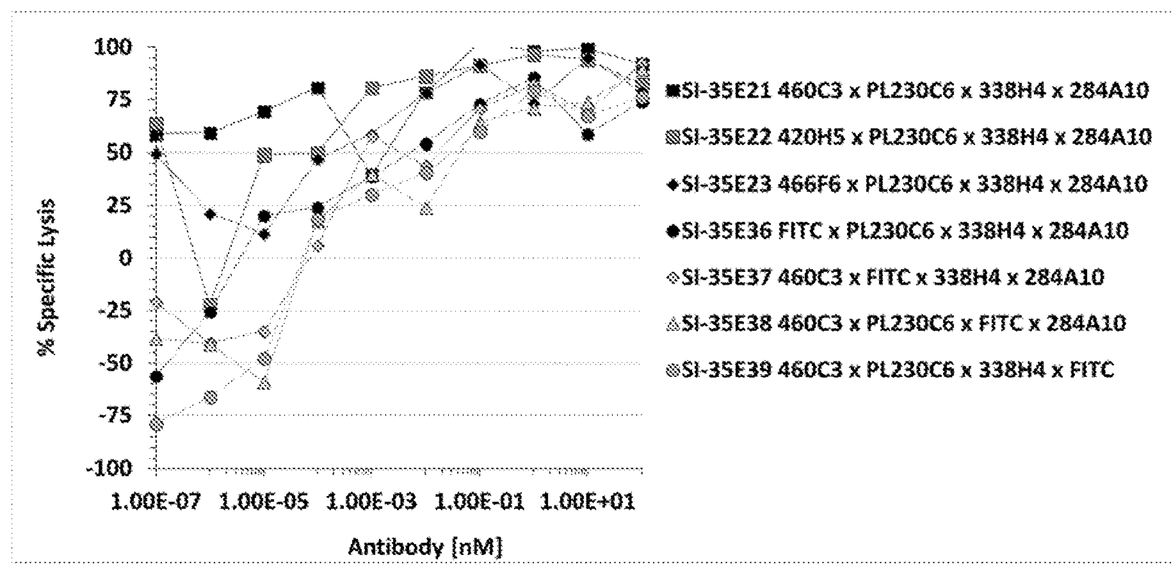

FIGURE 12. Tetra-specific GNC antibodies with the binding domain 338H4 which is specific for the Frizzled domain of ROR1 meditated RTCC of the B-ALL cell line Kasumi2 with CD8+, CD45RA+ naive T cells as effectors.
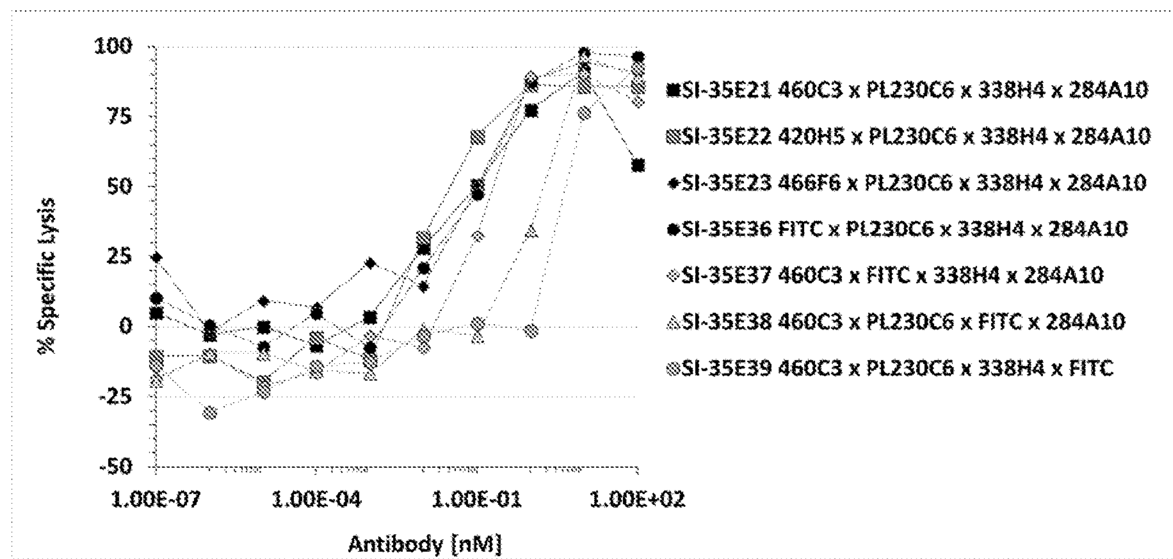

GUIDANCE AND NAVIGATION CONTROL PROTEINS AND METHOD OF MAKING AND USING THEREOF

CROSS REFERENCE TO RELATED APPLICATIONS

This application claims the benefit of U.S. Provisional Patent Application No. 62/648,880 filed Mar. 27, 2018, U.S. Provisional Patent Application No. 62/648,888 filed Mar. 27, 2018, U.S. Provisional Patent Application No. 62/551,032 filed Aug. 28, 2017, U.S. Provisional Patent Application No. 62/524,553 filed Jun. 25, 2017, U.S. Provisional Patent Application No. 62/545,603 filed Aug. 15, 2017, U.S. Provisional Patent Application No. 62/551,035 filed Aug. 28, 2017, U.S. Provisional Patent Application No. 62/551,065 filed Aug. 28, 2017, U.S. Provisional Patent Application No. 62/524,554 filed Jun. 25, 2017, U.S. Provisional Patent Application No. 62/524,557 filed Jun. 25, 2017, and U.S. Provisional Patent Application No. 62/524,558 filed Jun. 25, 2017, the entire disclosures of which are expressly incorporated by reference herein.

TECHNICAL FIELD

The present application generally relates to the technical field of Guidance and Navigation Control (GNC) proteins with multi-specific binding activities against surface molecules on both immune cells and tumor cells, and more particularly relates to making and using GNC proteins.

BACKGROUND

Cancer cells develop various strategies to evade the immune system. One of the underlaying mechanisms for the immune escape is the reduced recognition of cancer cells by the immune system. Defective presentation of cancer specific antigens or lack of thereof results in immune tolerance and cancer progression. In the presence of effective immune recognition tumors use other mechanisms to avoid elimination by the immune system. Immunocompetent tumors create suppressive microenvironment to downregulate the immune response. Multiple players are involved in shaping the suppressive tumor microenvironment, including tumor cells, regulatory T cells, Myeloid-Derived Suppressor cells, stromal cells, and other cell types. The suppression of immune response can be executed in a cell contact-dependent format as well as in and a contact-independent manner, via secretion of immunosuppressive cytokines or elimination of essential survival factors from the local environment. Cell contact-dependent suppression relies on molecules expressed on the cell surface, e.g. Programmed Death Ligand 1 (PD-L1), T-lymphocyte-associated protein 4 (CTLA-4) and others [Dunn, et al., 2004, Immunity, 21(2): 137-48; Adachi & Tamada, 2015, Cancer Sci., 106(8): 945-50].

As the mechanisms by which tumors evade recognition by the immune system continue to be better understood new treatment modalities that target these mechanisms have recently emerged. On Mar. 25, 2011, the U. S. Food and Drug Administration (FDA) approved ipilimumab injection (Yervoy, Bristol-Myers Squibb) for the treatment of unresectable or metastatic melanoma. Yervoy binds to cytotoxic T-lymphocyte-associated protein 4 (CTLA-4) expressed on activated T cells and blocks the interaction of CTLA-4 with CD80/86 on antigen-presenting cells thereby blocking the negative or inhibitory signal delivered into the T cell through CTLA-4 resulting in re-activation of the antigen-specific T cell leading to, in many patients, eradication of the tumor. A few years later in 2014 the FDA approved Keytruda (Pembrolizumab, Merck) and Opdivo (Nivolumab, Bristol-Myers Squibb) for treatment of advanced melanoma. These monoclonal antibodies bind to PD-1 which is expressed on activated and/or exhausted T cells and block the interaction of PD-1 with PD-L1 expressed on tumors thereby eliminating the inhibitory signal through PD-1 into the T cell resulting in re-activation of the antigen-specific T cell leading to again, in many patients, eradication of the tumor. Since then additional clinical trials have been performed comparing the single monoclonal antibody Yervoy to the combination of the monoclonal antibodies Yervoy and Opdivo in the treatment of advanced melanoma which showed improvement in overall survival and progression-free survival in the patients treated with the combination of antibodies. (Hodi et al., 2016, Lancet Oncol. 17(11): 1558-1568, Hellman et al., 2018, Cancer Cell 33(5): 853-861). However, as many clinical trials have shown a great benefit of treating cancer patients with monoclonal antibodies that are specific for one or more immune checkpoint molecules data has emerged that only those patients with a high mutational burden that generates a novel T cell epitope(s) which is recognized by antigen-specific T cells show a clinical response (Snyder et al., 2014, NEJM 371:2189-2199). Those patients that have a low tumor mutational load mostly do not show an objective clinical response (Snyder et al., 2014, NEJM 371:2189-2199, Hellman et al., 2018, Cancer Cell 33(5): 853-861).

In recent years other groups have developed an alternate approach that does not require the presence of neoepitope presentation by antigen-presenting cells to activate T cells. One example is the development of a bi-specific antibody where the binding domain of an antibody which is specific for a tumor associated antigen, e.g., CD19, is linked to and antibody binding domain specific for CD3 on T cells thus creating a bi-specific T cell engager or BiTe molecule. In 2014, the FDA approved a bi-specific antibody called Blinatumumab for the treatment of Precursor B-Cell Acute Lymphoblastic Leukemia. Blinatumumab links the scFv specific for CD19 expressed on leukemic cells with the scFv specific for CD3 expressed on T cells (Bejnjamin and Stein 2016, Ther Adv Hematol 7(3): 142-146). However, despite an initial response rate of >50% in patients with relapsed or refractory ALL many patients are resistant to Blinatumumab therapy or relapse after successful treatment with Blinatumumab. Evidence is emerging that the resistant to Blinatumumab or who relapse after Blinatumumab treatment is attributable to the expression of immune checkpoint inhibitory molecules expressed on tumor cells, such as PD-L1 that drives an inhibitory signal through PD-1 expressed on activated T cells (Feucht et al., 2016, Oncotarget 7(47): 76902-76919). In a case study of a patient who was resistant to therapy with Blinatumumab, a second round of Blinatumumab therapy was performed but with the addition of a monoclonal antibody, pembrolizumab (Keytruda, Merck), which specifically binds to PD-1 and blocks the interaction of T cell-expressed PD-1 with tumor cell expressed PD-L1, resulted in a dramatic response and reduction of tumor cells in the bone marrow from 45% to less than 5% in this one patient (Feucht et al., 2016, Oncotarget 7(47): 76902-76919). These results show that combining a bi-specific BiTe molecule with one or more monoclonal antibodies can significantly increase clinical activity compared to either agent alone. Despite the promising outcome, the cost leading to the combined therapy must be high due to multiple clinical trials and the difficulty in recruiting representative populations.

Adoptive cell therapy with chimeric antigen receptor T cells (CAR-T) is another promising immunotherapy for treating cancer. The clinical success of CAR-T therapy has revealed durable complete remissions and prolonged survival of patients with CD19-positive treatment-refractory B cell malignancies (Gill & June. 2015. Immunol Rev, 263: 68-89). However, the cost and complexity associated with the manufacture of a personalized and genetically modified CAR-T immunotherapy has restricted their production and use to specialized centers for treating relatively small numbers of patients. Cytokine release syndrome (CRS), also known as cytokine storms, is the most notable adverse effect after the infusion of engineered CAR-T cells (Bonifant et al., 201, Mol Ther Oncolytics. 3:16011). In many cases, the onset and severity of CRS seems to be specialized personal events. Current options of mitigating CRS are mainly focused on rapid response and management care because the option of controlling CRS prior to T cell infusion is limited.

While the efficacy of CAR-T therapy specific for a CD19-positive B cell malignancy is now established, the efficacy of CAR-T therapy against solid tumors has not been unequivocally demonstrated to date. Currently, many clinical trials are in progress to explore a variety of solid tumor-associated antigens (TAA) for CAR-T therapy. Inefficient T cell trafficking into the tumors, an immunosuppressive tumor micro-environment, suboptimal antigen recognition specificity, and lack of control over treatment-related adverse events are currently considered as the main obstacles in solid tumor CAR-T therapy (Li et al., 2018, J Hematol Oncol. 11(1): 22-40). The option of managing the therapeutic effect, as well as any adverse effect before and after the CAR-T cell infusion, is limited.

SUMMARY

The present application provides guidance and navigation control (GNC) proteins with multi-specific antigen binding activities to the surface molecules of a T cell and a tumour cell.

In one embodiment, the guidance and navigation control (GNC) protein, comprising a cytotoxic cell binding moiety and a cancer-targeting moiety. Any cytotoxic cells may be a potential binding target by the disclosed GNC proteins. Examples of the cytotoxic cell include, without limitation, T-cell, NK cell, macrophage cell, and dendritic cell.

In one embodiment, the GNC protein includes a T-cell binding moiety. The T-cell binding moiety has a binding specificity to a T-cell receptor. Examples T-cell receptor include without limitation CD3, CD28, PDL1, PD1, OX40, 4-1BB, GITR, TIGIT, TIM-3, LAG-3, CTLA4, CD40L, VISTA, ICOS, BTLA, Light, CD30, NKp30, CD28H, CD27, CD226, CD96, CD112R, A2AR, CD160, CD244, CECAM1, CD200R, TNFRSF25 (DR3), or a combination thereof.

In one embodiment, the GNC protein includes a NK cell binding moiety. The NK cell binding moiety has a binding specificity to a NK cell receptor. Examples NK cell receptor include, without limitation, receptors for activation of NK cell such as CD16, NKG2D, KIR2DS1, KIR2DS2, KIR2DS4, KIR3DS1, NKG2C, NKG2E, NKG2H; agonist receptors such as NKp30a, NKp30b, NKp46, NKp80, DNAM-1, CD96, CD160, 4-1BB, GITR, CD27, OX-40, CRTAM; and antagonist receptors such as KIR2DL1, KIR2DL2, KIR2DL3, KIR3DL1, KIR3DL2, KIR3DL3, NKG2A, NKp30c, TIGIT, SIGLEC7, SIGLEC9, LILR, LAIR-1, KLRG1, PD-1, CTLA-4, CD161.

In one embodiment, the GNC protein includes a macrophage binding moiety. The macrophage binding moiety has a binding specificity to a macrophage receptor. Examples macrophage receptor include, without limitation, agonist receptor on macrophage such as TLR2, TLR4, CD16, CD64, CD40, CD80, CD86, TREM-1, TREM-2, ILT-1, ILT-6a, ILT-7, ILT-8, EMR2, Dectin-1, CD69; antagonist receptors such as CD32b, SIRPa, LAIR-1, VISTA, TIM-3, CD200R, CD300a, CD300f, SIGLEC1, SIGLEC3, SIGLEC5, SIGLEC7, SIGLEC9, ILT-2, ILT-3, ILT-4, ILT-5, LILRB3, LILRB4, DCIR; and other surface receptors such as CSF-1R, LOX-1, CCR2, FRB, CD163, CR3, DC-SIGN, CD206, SR-A, CD36, MARCO.

In one embodiment, the GNC protein includes a dendritic cell binding moiety. The dendritic cell binding moiety has a binding specificity to a dendritic cell receptor. Examples dendritic cell receptor include, without limitation, agonist receptors on dendritic cell such as TLR, CD16, CD64, CD40, CD80, CD86, HVEM, CD70; antagonist receptors such as VISTA, TIM-3, LAG-3, BTLA; and other surface receptors such as CSF-1R, LOX-1, CCR7, DC-SIGN, GM-CSF-R, IL-4R, IL-10R, CD36, CD206, DCIR, RIG-1, CLEC9A, CXCR4.

The cancer targeting moiety has a binding specificity to a cancer cell receptor. Example cancer cell receptor include without limitation BCMA, CD19, CD20, CD33, CD123, CD22, CD30, ROR1, CEA, HER2, EGFR, EGFRvIII, LMP1, LMP2A, Mesothelin, PSMA, EpCAM, glypican-3, gpA33, GD2, TROP2, or a combination thereof.

In one embodiment, GNC proteins comprise at least one T-cell binding moiety and at least one cancer cell binding moiety, wherein the T-cell binding moiety has a binding specificity to a T-cell receptor comprising CD3, CD28, PDL1, PD1, OX40, 4-1BB, GITR, TIGIT, TIM-3, LAG-3, CTLA4, CD40, VISTA, ICOS, BTLA, Light, CD30, CD27, or a combination thereof, and wherein the cancer cell binding moiety has a binding specificity to a cancer cell receptor.

In one embodiment, the cancer receptor comprises a receptor on a lung cancer cell, a liver cancer cell, a breast cancer cell, a colorectal cancer cell, an anal cancer cell, a pancreatic cancer cell, a gallbladder cancer cell, a bile duct cancer cell, a head and neck cancer cell, a nasopharyngeal cancer cell, a skin cancer cell, a melanoma cell, an ovarian cancer cell, a prostate cancer cell, a urethral cancer cell, a lung cancer cell, a non-small lung cell cancer cell, a small cell lung cancer cell, a brain tumour cell, a glioma cell, a neuroblastoma cell, an esophageal cancer cell, a gastric cancer cell, a liver cancer cell, a kidney cancer cell, a bladder cancer cell, a cervical cancer cell, an endometrial cancer cell, a thyroid cancer cell, an eye cancer cell, a sarcoma cell, a bone cancer cell, a leukemia cell, a myeloma cell, a lymphoma cell, or a combination thereof.

In one embodiment, the GNC protein is capable of activating a T-cell by binding the T-cell binding moiety to a T-cell receptor on the T-cell. In one embodiment, the GNC protein comprises a bi-specific antibody or antibody monomer, a tri-specific antibody or antibody monomer, a tetra-specific antibody or antibody monomer, an antigen-binding fragment thereof, or a combination thereof. In one embodiment, the GNC protein comprises an amino acid sequence having a percentage homology to SEQ ID NO. 49-52, wherein the percentage homology is not less than 70%, 80%, 90%, 95%, 98%, or 99%.

In one embodiment, the GNC protein may have a first moiety and a second moiety. In one embodiment, the first moiety may include a T-cell binding moiety, a NK cell binding moiety, a macrophage binding moiety, or a dendritic cell binding moiety. The second moiety comprises the cancer-targeting moiety.

In one embodiment, the first moiety and the second moiety may have binding specificities toward each other. In these embodiments, the GNC proteins are formed by the binding action between the first moiety and the second moiety. The binding action is a non-covalent bonding. In one embodiment, the GNC protein includes the first moiety bound to the second moiety through a high affinity non-covalent bonding interaction. Examples of high affinity non-covalent bonding interaction include, without limitation, antibody-antigen interaction, biotin-streptavidin interaction, leucine-zipper, and any pair of proteins from a two-hybrid screening assay, non-immunoglobulin protein scaffolds (Hosse et al., 2006, Protein Sci. 15(1): 14-27), or aptamers (Likhin et al., 2013, Acta Naturae. 2013. 5(4): 34-43), or a combination thereof.

In one embodiment, the GNC protein may further include a linker moiety. In one embodiment, the first moiety and the first moiety are joined through a linker moiety to provide the GNC protein. In one embodiment, the linker moiety may covalently link the first and the second moieties together to provide the GNC protein. In one embodiment, the linker moiety may include two complimentary molecules or a stable protein-protein interaction. Examples of complimentary molecules include without limitation the complementary strands of DNA and RNA. Examples of stable protein-protein interaction include, but not limited to, biotin-avidin, leucine-zipper, and any pair of proteins from a two-hybrid screening assay.

In one embodiment, the linker moiety may include the backbone of an immunoglobulin G (IgG), where a GNC proteins may include an immunoglobulin G (IgG) moiety with two heavy chains and two light chains, and at least two scFv moieties being covalently connected to either C or N terminals of the heavy or light chains. The IgG moiety may provide stability to the scFv moiety, and a tri-specific GNC protein may have two moieties for binding the surface molecules on T cells.

In one embodiment, the first moiety comprises an antibody or a fragment thereof, a soluble receptor or a combination thereof. In one embodiment, the second moiety comprises an antibody or a fragment, a soluble receptor or a combination thereof.

The application further provides therapeutic complexes incorporating the GNC protein disclosed herein. In one embodiment, the therapeutic complex includes the GNC protein and a cytotoxic cell. The cytotoxic cell may T cell, NK cell, macrophage, dendritic cell, or a combination thereof. In one embodiment, the T cell may be autologous T cells, allo T cells, or universal donor T cells.

In one embodiment, the therapeutic complex may include the GNC protein and a cancer cell. In one embodiment, the therapeutic complex may include the GNC protein disclosed herein having a T-cell bound to the T-cell binding moiety and a cancer cell bound to the caner-targeting moiety.

The application further provides pharmaceutical compositions. In one embodiment, the pharmaceutical composition includes the therapeutic complex disclosed herein and a pharmaceutically acceptable carrier. In one embodiment, the pharmaceutical composition includes the GNC protein disclosed herein and a pharmaceutically acceptable carrier.

In a further aspect, the application provides methods for making and using the disclosed GNC proteins.

The objectives and advantages of the present application will become apparent from the following detailed description of preferred embodiments thereof in connection with the accompanying drawings.

BRIEF DESCRIPTION OF THE DRAWINGS

The foregoing and other features of this disclosure will become more fully apparent from the following description and appended claims, taken in conjunction with the accompanying drawings. Understanding that these drawings depict only several embodiments arranged in accordance with the disclosure and are, therefore, not to be considered limiting of its scope, the disclosure will be described with additional specificity and detail through use of the accompanying drawings, in which:

FIG. 1 shows example GNC proteins, which are characterized by their composition of multiple antigen binding domains (AgBd) and linkers.

FIG. 2 shows an example format of a tetra-specific GNC antibody as an embodiment.

FIG. 3 shows that an example tetra-specific GNC antibody binds to both a T cell and a tumor cell through multiple AgBds.

FIG. 4 shows the example tetra-specific GNC antibodies binding to human ROR1 transfected CHO cells.

FIG. 5 shows the example tetra-specific GNC antibodies binding to human 41BB transfected CHO cells.

FIG. 6 shows the example tetra-specific GNC antibodies binding to human PD-L1 transfected CHO cells.

FIG. 7 shows the example tetra-specific GNC antibodies with the binding domain 323H7 which is specific for the Ig domain of ROR1 meditated RTCC of the B-ALL cell line Kasumi2 with PBMC as effectors.

FIG. 8 shows the example tetra-specific GNC antibodies with the binding domain 323H7 which is specific for the Ig domain of ROR1 meditated RTCC of the B-ALL cell line Kasumi2 with CD8+, CD45RO+ memory T cells as effectors.

FIG. 9 shows the example tetra-specific GNC antibodies with the binding domain 323H7 which is specific for the Ig domain of ROR1 meditated RTCC of the B-ALL cell line Kasumi2 with CD8+, CD45RA+ naive T cells as effectors.

FIG. 10 shows the example tetra-specific GNC antibodies with the binding domain 338H4 which is specific for the Frizzled domain of ROR1 meditated RTCC of the B-ALL cell line Kasumi2 with PBMC as effectors.

FIG. 11. Tetra-specific antibodies with the binding domain 338H4 which is specific for the Frizzled domain of ROR1 mediated RTCC of the B-ALL cell line Kasumi2 with CD8+, CD45RO+ memory T cells as effectors.

FIG. 12 shows the example tetra-specific GNC antibodies with the binding domain 338H4 which is specific for the Frizzled domain of ROR1 meditated RTCC of the B-ALL cell line Kasumi2 with CD8+, CD45RA+ naive T cells as effectors.

DETAILED DESCRIPTION

In the following detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be utilized, and other changes may be made, without departing from the spirit or scope of the subject matter presented herein. It will be readily understood that the aspects of the present disclosure, as generally described herein, and illustrated in the Figures, can be arranged, substituted, combined, separated, and designed in a wide variety of different configurations, all of which are explicitly contemplated herein.

In one embodiment, the guidance navigation control (GNC) proteins are characterized by their composition of multiple antigen-specific binding domains (AgBDs) and by their ability of directing T cells (or other effector cells) to cancer cells (or other target cells) through the binding of multiple surface molecules on a T cell and a tumor cell (FIG. 1). By this definition, GNC proteins are composed of Moiety 1 for binding at least one surface molecule on a T cell and Moiety 2 for binding at least one surface antigen on a cancer cell (TABLE 1A). In a T cell therapy, the cytotoxic T cells are regulated by T cell proliferation signaling, as well as co-stimulation signaling via either agonist receptors or antagonist receptors on their surface. To regulate these signaling, as well as the interplay between a T cell and a cancer, multiple AgBDs may be necessary for Moiety 1 and Moiety 2, respectively. GNC proteins must have at least one linker to link Moiety 1 and Moiety 2. In a conceptual GNC protein, any linker molecule can be used to link two or more AgBDs together either in vitro or in vivo by using complementary linkers of DNA/RNA or protein-protein interactions, including but not limited to, that of biotin-avidin, leucine-zipper, and any two-hybrid positive protein. However, in the present application all the linkers are either an antibody backbone structure or antibody fragments, so that GNC protein and GNC antibody may have the same meaning, e.g. an example of a tetra-specific GNC antibody structure in FIG. 2. GNC proteins or antibodies are capable of directing the binding of a T cell to a cancer cell in vivo or ex vivo, mediated by multiple AgBDs (FIG. 3). The T cells may be derived from the same patient or different individuals, and the cancer cell may exist in vivo, in vitro, or ex vivo. The examples provided in the present application enable GNC proteins as a prime agent in a T cell therapy, i.e. GNC-T therapy, for activating and controlling cytotoxic T cells ex vivo, prior to adoptive transfer.

TABLE 1A

Composition of functional moieties (Moiety 1 and Moiety 2) and antigen binding domain in example GNC proteins with T cell binding domains

| Moiety 1 | | | Moiety 2 |
|---|---|---|---|
| Activation of T cells | Agonist receptor | Antagonist receptor | Tumor Antigen |
| CD3 | CD28, 41BB, OX40, GITR, CD40L, ICOS, Light, CD27, CD30 | PDL1, PD1, TIGIT, TIM-3, LAG-3, CTLA4, BTLA, VISTA, PDL2 | BCMA, CD19, CD20, CD33, CD123, CD22, CD30, ROR1, CEA, HER2, EGFR, EGFRvIII, LMP1, LMP2A, Mesothelin, PSMA, EpCAM, glypican-3, gpA33, GD2, TROP2 |

In addition to T cells, other cytotoxic cells may also be utilized by the GNC proteins for cancer killing or preventing purposes. TABLE 1B shows the example compositions of functional moieties (Moiety 1 and Moiety 2) and antigen binding domain in GNC proteins with NK cell binding domains. TABLE 1C shows the example compositions of functional moieties (Moiety 1 and Moiety 2) and antigen binding domain in GNC proteins with macrophage binding domains. TABLE 1D shows the example compositions of functional moieties (Moiety 1 and Moiety 2) and antigen binding domain in GNC proteins with dendritic cell binding domains.

TABLE 1B

| Moiety 1 | | | Moiety 2 |
|---|---|---|---|
| Activation of NK cell | Agonist receptor | Antagonist receptor | Tumor Antigen |
| CD16, NKG2D, KIR2DS1, KIR2DS2, KIR2DS4, KIR3DS1, NKG2C, NKG2E, NKG2H | NKp30a, NKp30b, NKp46, NKp80, DNAM-1, CD96, CD160, 4-1BB, GITR, CD27, OX-40, CRTAM | KIR2DL1, KIR2DL2, KIR2DL3, KIR3DL1, KIR3DL2, KIR3DL3, NKG2A, NKp30c, TIGIT, SIGLEC7, SIGLEC9, LILR, LAIR-1, KLRG1, PD-1, CTLA-4, CD161 | BCMA, CD19, CD20, CD33, CD123, CD22, CD30, ROR1, CEA, HER2, EGFR, EGFRvIII, LMP1, LMP2A, Mesothelin, PSMA, EpCAM, glypican-3, gpA33, GD2, TROP2 |

TABLE 1C

| Moiety 1 | | | |
|---|---|---|---|
| Agonist receptor on macrophage | Antagonist receptor on macrophage | Other surface receptors | Moiety 2 Tumor Antigen |
| TLR2, TLR4, CD16, CD64, CD40, CD80, CD86, TREM-1, TREM-2, ILT-1, ILT-6a, ILT-7, ILT-8, EMR2, Dectin-1, CD69 | CD32b, SIRPα, LAIR-1, VISTA, TIM-3, CD200R, CD300a, CD300f, SIGLEC1, SIGLEC3, SIGLEC5, SIGLEC7, SIGLEC9, ILT-2, ILT-3, ILT-4, ILT-5, LILRB3, LILRB4, DCIR | CSF-1R, LOX-1, CCR2, FRβ, CD163, CR3, DC-SIGN, CD206, SR-A, CD36, MARCO | BCMA, CD19, CD20, CD33, CD123, CD22, CD30, ROR1, CEA, HER2, EGFR, EGFRvIII, LMP1, LMP2A, Mesothelin, PSMA, EpCAM, glypican-3, gpA33, GD2, TROP2 |

TABLE 1D

| Moiety 1 | | | |
|---|---|---|---|
| Agonist receptor on DC | Antagonist receptor on DC | Other surface receptors | Moiety 2 Tumor Antigen |
| TLR, CD16, CD64, CD40, CD80, CD86, HVEM, CD70 | VISTA, TIM-3, LAG-3, BTLA | CSF-1R, LOX-1, CCR7, DC-SIGN, GM-CSF-R, IL-4R, IL-10R, CD36, CD206, DCIR, RIG-1, CLEC9A, CXCR4 | BCMA, CD19, CD20, CD33, CD123, CD22, CD30, ROR1, CEA, HER2, EGFR, EGFRvIII, LMP1, LMP2A, Mesothelin, PSMA, EpCAM, glypican-3, gpA33, GD2, TROP2 |

The present application relates to methods of making and using recombinant GNC proteins. Multiple AgBDs can be divided into Moiety 1 and Moiety 2 due to their interface with a cytotoxic cell such as a T cell and a cancer cell, respectively (TABLE 1A). However, the rearrangement of multiple AgBDs may be random and in unequal numbers (TABLE 2). A GNC protein with two AgBDs may simultaneously bind to a surface molecule, such as CD3 on a T cell, and a tumor antigen, such as ROR1 on a tumor cell, for re-directing or guiding the T cell to the tumor cell. The addition of the third AgBD, e.g. specifically bind to 41BB, may help enhance anti-CD3-induced T cell activation because 41BB is a co-stimulation factor and the binding stimulates its agonist activity to activated T cells. The addition of the fourth AgBD to a GNC protein, e.g. specifically bind to PD-L1 on a tumor cell, may block the inhibitory pathway of PD-L1 on tumor cells that is mediated through its binding to PD-1 on the T cells. With these basic principles, GNC proteins may be designed and constructed to acquire multiple AgBDs specifically for binding unequal numbers of T cell antagonists and agonists, not only to re-direct activated T cells to tumor cells but also to control their activity in vivo (TABLE 2). Therefore, the design of GNC proteins may be any multi-specific proteins.

In one embodiment, the GNC protein may be a bi-specific, tri-specific, tetra-specific, penta-specific, hexa-specific, hepta-specific, or octa-specific proteins. In one embodiment, the GNC protein may be a monoclonal antibodies. In one embodiment, the GNC protein may be a bi-specific, tri-specific, tetra-specific, penta-specific, hexa-specific, hepta-specific, or octa-specific antibody monomers. In one embodiment, the GNC protein may be a bi-specific, tri-specific, tetra-specific, penta-specific, hexa-specific, hepta-specific, or octa-specific antibodies. TABLE 3 provides some example GNC proteins and antibodies with the specificity of antibody binding domains.

TABLE 2

Examples of possible combinations of T cell activation, T cell agonist, T cell antagonist, and tumor antigen binding domains in a single GNC protein.

| GNC protein | T cell activation | Tumor antigen | T cell antagonist | T cell agonist | T cell antagonist | T cell antagonist | T cell antagonist | T cell agonist |
|---|---|---|---|---|---|---|---|---|
| Bi-specific | CD3 | ROR1 | | | | | | |
| Tri-specific | CD3 | ROR1 | PD1 | | | | | |
| Tetra-specific | CD3 | ROR1 | PD1 | 41BB | | | | |
| Penta-specific | CD3 | ROR1 | PD1 | 41BB | LAG3 | | | |
| Hexa-specific | CD3 | ROR1 | PD1 | 41BB | LAG3 | TLM3 | | |
| Hepta-specific | CD3 | ROR1 | PD1 | 41BB | LAG3 | TLM3 | TIGIT | |
| Octa-specific | CD3 | ROR1 | PD1 | 41BB | LAG3 | TLM3 | TIGIT | CD28 |

TABLE 3

| Specificity of antibody binding domains used in GNC proteins. | |
|---|---|
| Antibody Name | Specificity |
| 460C3 | 41BB |
| 420H5 | 41BB |
| 466F6 | 41BB |
| PL230C6 | PD-L1 |
| 323H7 | ROR1 IgD Domain |
| 338H4 | ROR1 Frizzled Domain |
| 330F11 | ROR1 Kringle Domain |
| 324C6 | ROR1 Frizzled Domain |
| 4420 | FITC |
| 284A10 | CD3 complex Epsilon chain |
| 480C8 | CD3 complex Epsilon chain |

In one embodiment, the application provides methods of making and using recombinant GNC proteins. GNC proteins are composed of multi-specific antigen binding moieties characterized by two functional groups: Moiety 1 comprises multiple antigen binding domains (AgBD) whose specificities are implicated in T-cell activation, agonist co-stimulation, and/or inhibitory antagonist activity, and Moiety 2 comprises at least one cancer cell binding specificity. GNC proteins may simultaneously bind to a surface molecule, such as CD3 of a T cell, and a tumor antigen, such as ROR1 of a tumor cell, thereby re-directing or guiding the T cell to the tumor cell. An addition of the third binding domain in a GNC protein may help enhance the CD3-induced T cell activation through its direct binding of 41BB, which is a co-stimulation factor exerting agonist activity. Furthermore, an addition of the fourth binding domain in a GNC protein may bind to PD-L1 on the tumor cell to block the inhibitory pathway of PD-L1 on tumor cells that is mediated through its binding to PD-1 on the T cells. In this way, GNC proteins acquire multiple binding capacities to re-direct activated T cells to tumor cells, and multiple binding may help modulate T cell activation through modulating either agonist or antagonist activity or both. Some binding capacities may be similar to that of either the chimeric antigen receptor on a CAR-T cell or a bi-specific antibody, such as the BiTe antibody. While GNC proteins are unique, their ability of guidance and navigation control of the interaction between activated T cells and tumor cells remains to be demonstrated.

In one embodiment, an example GNC protein with 4 different binding domains is disclosed. This GNC protein is a "tetra-specific antibody" since its linkers and backbone comprises antibody fragments. Of the 4 different antigen binding domains, one specifically binds to CD3 on T cells, the second binding domain is specific against a tumor associated antigen, including but not limited to other tumor antigens, such as ROR1, CEA, HER2, EGFR, EGFRvIII, LMP1, LMP2A, Mesothelin, PSMA, EpCAM, glypican-3, gpA33, GD2, TROP2, BCMA, CD19, CD20, CD33, CD123, CD22, CD30, and the third and fourth binding domains are specific against two distinct immune checkpoint modulators, namely, PD-L1, PD-1, OX40, 4-1BB, GITR, TIGIT, TIM-3, LAG-3, CTLA4, CD40, VISTA, ICOS, BTLA, Light, HVEM, CD73, CD39, etc. Because of their definition in function and variety in composition, GNC proteins can be classified as a new class of immune-modulators for treating cancer. TABLE 4 shows the list of the example tetra-specific GNC antibodies.

TABLE 4

List of tetra-specific GNC antibodies.

| Antibody ID | Domain 1 LH-scFv | Humanized Variant | Domain 2 Fab | Humanized Variant | IgG Fc | Domain 3 LH-scFv | Humanized Variant | Domain 4 LH-scFv | Humanized Variant |
|---|---|---|---|---|---|---|---|---|---|
| SI-35E18 | 460C3 | H1L1 | PL230C6 | H3L3 | n2 | 323H7 | H4L1 | 284A10 | H1L1 |
| SI-35E19 | 420H5 | H3L3 | PL230C6 | H3L3 | n2 | 323H7 | H4L1 | 284A10 | H1L1 |
| SI-35E20 | 466F6 | H2L5 | PL230C6 | H3L3 | n2 | 323H7 | H4L1 | 284A10 | H1L1 |
| SI-35E21 | 460C3 | H1L1 | PL230C6 | H3L3 | n2 | 338H4 | H3L4 | 284A10 | H1L1 |
| SI-35E22 | 420H5 | H3L3 | PL230C6 | H3L3 | n2 | 338H4 | H3L4 | 284A10 | H1L1 |
| SI-35E23 | 466F6 | H2L5 | PL230C6 | H3L3 | n2 | 338H4 | H3L4 | 284A10 | H1L1 |
| SI-35E24 | 460C3 | H1L1 | PL230C6 | H3L3 | n2 | 330F11 | H1L1 | 284A10 | H1L1 |
| SI-35E25 | 420H5 | H3L3 | PL230C6 | H3L3 | n2 | 330F11 | H1L1 | 284A10 | H1L1 |
| SI-35E26 | 466F6 | H2L5 | PL230C6 | H3L3 | n2 | 330F11 | H1L1 | 284A10 | H1L1 |
| SI-27E12 | 4420 | ~ | PL230C6 | H3L3 | n2 | 324C6 | H2L1 | 480C8 | H1L1 |
| SI-27E15 | 460C3 | H1L1 | 4420 | ~ | n2 | 324C6 | H2L1 | 480C8 | H1L1 |
| SI-27E13 | 460C3 | H1L1 | PL230C6 | H3L3 | n2 | 4420 | ~ | 480C8 | H1L1 |
| SI-35E2 | 460C3 | H1L1 | PL230C6 | H3L3 | n2 | 324C6 | H2L1 | 4420 | ~ |

In one embodiment, GNC-mediated immunotherapy may include types of antibody therapy and cell therapy. Herein, the advantages may include, but not limited to, the inclusion of an IgG Fc domain may confer the characteristic of a longer half-life in serum compared to a bi-specific BiTe molecule; second, the inclusion of two binding domains specific for immune checkpoint modulators may inhibit the suppressive pathways and engage the co-stimulatory pathways at the same time; third, that cross-linking CD3 on T cells with tumor associated antigens re-directs and guides T cells to kill the tumor cells without the need of removing T cells from the patient and genetically modifying them to be specific for the tumor cells before re-introducing them back into the patient, also known as chimeric antigen receptor T cells (CAR-T) therapy; and fourth, that GNC protein-mediated antibody therapy or T cell therapy does not involve genetic modification of T cells, the latter of which may carry the risk of transforming modified T cells to clonal expansion, i.e. T cell leukemia.

With one or more addition of the binding capacity, the advantage of GNC protein-mediated immunotherapy over conventional immunotherapies include, but not limited to, first, that inclusion of an IgG Fc domain may confer the characteristic of a longer half-life in serum compared to a bi-specific BiTe molecule; second, that inclusion of two binding domains specific for immune checkpoint modulators may inhibit the suppressive pathways and engage the co-stimulatory pathways at the same time; third, that cross-linking CD3 on T cells with tumor associated antigens re-directs and guides T cells to kill the tumor cells without the need of removing T cells from the patient and genetically modifying them to be specific for the tumor cells before re-introducing them back into the patient, also known as chimeric antigen receptor T cells (CAR-T) therapy; and fourth, that GNC protein-mediated antibody therapy or T cell therapy does not involve genetic modification of T cells, the latter of which may carry the risk of transforming modified T cells to clonal expansion, i.e. T cell leukemia.

The present disclosure may be understood more readily by reference to the following detailed description of specific embodiments and examples included herein. Although the present disclosure has been described with reference to specific details of certain embodiments thereof, it is not intended that such details should be regarded as limitations upon the scope of the disclosure.

EXAMPLES

While the following examples are provided by way of illustration only and not by way of limitation. Those of skill in the art will readily recognize a variety of non-critical parameters that could be changed or modified to yield essentially the same or similar results.

Example 1: FACS Analysis of Tetra-Specific Specific Antibody Binding to Human ROR1 Transfected CHO Cells The tetra-specific GNC antibodies listed in TABLEs 3 and 4 were tested for binding to Chinese hamster ovary cells (CHO) cells stably expressing a full-length human ROR1. Antibodies were prepared at 2× final concentration and titrated 1:5 across 3 wells of a 96 well plate in 50 ul of PBS/2% FBS and then 5,000 ROR1-CHO cells in 50 ul PBS/2% FBS were added. This mixture was incubated for 30 minutes on ice, washed once with 200 ul PBS/2% FBS, and then the secondary antibody PE Goat anti-Human IgG Fc at 1:1000 dilution of stock was added, and this mixture was incubated for 30 minutes on ice. Cells were washed 2×200 ul PBS/2% FBS, resuspended in 50 ul PBS/2% FBS and analyzed on a BD LSRFORTESSA and the binding profile is shown in FIG. 4. The tetra-specific antibodies SI-35E18, 19, and 20, with the 323H7 binding domain specific for the Ig domain of ROR1, showed higher binding than the tetra-specific GNC antibodies SI-3521, 22, and 23, with the 338H4 binding domain specific for the frizzled domain of ROR1, and the tetra-specific GNC antibodies SI-3524, 25, and 26, with the 330F11 binding domain specific for the kringle domain of ROR1, did not bind.

Example 2: FACS Analysis of Tetra-Specific GNC Antibody Binding to Human 41BB Transfected CHO Cells The tetra-specific GNC antibodies listed in TABLEs 3 and 4 were tested for binding to Chinese hamster ovary cells (CHO) cells stably expressing a full-length human ROR1. Antibodies were prepared at 2× final concentration and titrated 1:5 across 3 wells of a 96 well plate in 50 ul of PBS/2% FBS and then 5,000 ROR1-CHO cells in 50 ul PBS/2% FBS were added. This mixture was incubated for 30 minutes on ice, washed once with 200 ul PBS/2% FBS, and then the secondary antibody PE Goat anti-Human IgG Fc at 1:1000 dilution of stock was added, and this mixture was incubated for 30 minutes on ice. Cells were washed 2×200 ul PBS/2% FBS, resuspended in 50 ul PBS/2% FBS and analyzed on a BD LSRFORTESSA and the binding profile is shown in FIG. 5. All of the tetra-specific GNC antibodies except for the control SI-27E12 contain a 41BB binding domain, 460C3, 420H5, or 466F6 and bound to 41BB expressing CHO cells with varying intensity.

Example 3: FACS Analysis of Tetra-Specific GNC Antibody Binding to Human PDL1 Transfected CHO Cells The tetra-specific GNC antibodies listed in TABLEs 3 and 4 were tested for binding to Chinese hamster ovary cells (CHO) cells stably expressing full length human ROR1. Antibodies were prepared at 2× final concentration and titrated 1:5 across 3 wells of a 96 well plate in 50 ul of PBS/2% FBS and then 5,000 ROR1-CHO cells in 50 ul PBS/2% FBS were added. This mixture was incubated for 30 minutes on ice, washed once with 200 ul PBS/2% FBS, and then the secondary antibody PE Goat anti-Human IgG Fc at 1:1000 dilution of stock was added, and this mixture was incubated for 30 minutes on ice. Cells were washed 2×200 ul PBS/2% FBS, resuspended in 50 ul PBS/2% FBS and analyzed on a BD LSRFORTESSA and the binding profile is shown in FIG. 6. All of the tetra-specific GNC antibodies except for the control SI-27E15 contain the same PDL1 binding domain, PL230C6, and showed very similar binding intensity to PDL1 expressing CHO cells.

Example 4: Re-Directed T Cell Cytotoxicity (RTCC) Assay with Peripheral Blood Mononuclear Cells as Effectors and B-Acute Lymphoblastic Leukemia (B-ALL) Cell Line Kasumi-2 as Targets The tetra-specific GNC antibodies listed in TABLEs 3 and 4 were tested for RTCC activity against the B-ALL cell line Kasumi 2 using human peripheral blood mononuclear cells (PBMC) as effectors. The Kasumi 2 target cells, $5\times10^6$, were labeled with CFSE (Invitrogen, #C34554) at 0.5 uM in 10 ml of culture media for 20 minutes at 37° C. The cells were washed 3 times with 50 ml of culture media before resuspending in 10 ml then counted again. Antibodies were prepared at 2× final concentration and titrated 1:3 across 10 wells of a 96 well plate in 200 ul of RPMI+10% FBS. Human PBMC were purified by standard ficoll density gradient from a “leukopak” which is an enriched leukapheresis product collected from normal human peripheral blood. In the final destination 96 well plate the target cells, PBMC, and serially titrated antibodies were combined by adding 100 μl of target cells (5,000), 50 ul of PBMC (25,000), and 100 ul of each antibody dilution to each well of the assay. The assay plate was incubated at 37° C. for approximately 72 hours and then the contents of each assay well were harvested and analyzed for the number of CFSE-labeled target cells remaining. As shown on FIG. 7, the tetra-specific GNC antibodies all contain the same PDL1 binding domain PL230C6, the same ROR1 binding domain 323H7, and the same CD3 binding domain 284A10, but have one of the 41BB binding domains 460C3, 420H5, and 466F6 and showed greater RTCC activity compared to the controls except for the control SI-27E12 which does not have a 41BB binding domain but appeared to be similarly potent at the tetra-specific GNC antibodies SI-35E18, 19, and 20.

Example 5: Re-Directed T Cell Cytotoxicity (RTCC) Assay with CD8+, CD45RO+ Memory T Cells as Effectors and B-Acute Lymphoblastic Leukemia (B-ALL) Cell Line Kasumi-2 as Targets The tetra-specific GNC antibodies listed in TABLE 3 and 4 were tested for RTCC activity against the B-ALL cell line Kasumi 2 using human CD8+, CD45RO+ memory T cells as effectors. The Kasumi 2 target cells, $5\times10^6$, were labeled with CFSE (Invitrogen, #C34554) at 0.5 uM in 10 ml of culture media for 20 minutes at 37° C. The cells were washed 3 times with 50 ml of culture media before resuspending in 10 ml then counted again. Antibodies were prepared at 2× final concentration and titrated 1:3 across 10 wells of a 96 well plate in 200 ul of RPMI+10% FBS. Human CD8+, CD45RO+ memory T cells were enriched from PBMC from a normal donor using the EasySep™ Human Memory CD8+ T Cell Enrichment Kit (Stemcell Technologies, #19159) as per the manufacturers protocol. The final cell population was determined to be 98% CD8+, CD45RO+ T cells by FACS analysis. In the final destination 96 well plate the target cells, T cells, and serially titrated antibodies were combined by adding 100 μl of target cells (5,000), 50 ul of CD8+, CD45RO+ memory T cells (25,000), and 100 ul of each antibody dilution to each well of the assay. The assay plate was incubated at 37 C for approximately 72 hours and then the contents of each assay well were harvested and analyzed for the number of CFSE-labeled target cells remaining. As shown on FIG. 8, the tetra-specific antibodies all contain the same PDL1 binding domain PL230C6, the same ROR1 binding domain 323H7, and the same CD3 binding domain 284A10, but have one of the 41BB binding domains 460C3, 420H5, and 466F6 and showed greater RTCC activity compared to the controls that do not contain one of the 41BB, PDL1, ROR1, or CD3 binding domains.

Example 6: Re-Directed T Cell Cytotoxicity (RTCC) Assay with CD8+, CD45RA+ Naive T Cells as Effectors and B-Acute Lymphoblastic Leukemia (B-ALL) Cell Line Kasumi-2 as Targets The tetra-specific-specific antibodies listed in TABLEs 3 and 4 were tested for RTCC activity against the B-ALL cell line Kasumi 2 using human CD8+, CD45RA+ memory T cells as effectors. The Kasumi 2 target cells, 5x10e6, were labeled with CFSE (Invitrogen, #C34554) at 0.5 uM in 10 ml of culture media for 20 minutes at 37 C. The cells were washed 3 times with 50 ml of culture media before resuspending in 10 ml then counted again. Antibodies were prepared at 2× final concentration and titrated 1:3 across 10 wells of a 96 well plate in 200 ul of RPMI+10% FBS. Human CD8+, CD45RA+ memory T cells were enriched from peripheral blood mononuclear cells from a normal donor using the EasySep™ Human Naïve CD8+ T Cell Isolation Kit (Stemcell Technologies, #19258) as per the manufacturers protocol. The final cell population was determined to be 98% CD8+, CD45RA+ T cells by FACS analysis (data not shown). In the final destination 96 well plate the target cells, T cells, and serially titrated antibodies were combined by adding 100 μl of target cells (5,000), 50 ul of CD8+, CD45RO+ T cells (25,000), and 100 ul of each antibody dilution to each well of the assay. The assay plate was incubated at 37 C for approximately 72 hours and then the contents of each assay well were harvested and analyzed for the number of CFSE-labeled target cells remaining. As shown on FIG. 9, the tetra-specific antibodies all contain the same PDL1 binding domain PL230C6, the same ROR1 binding domain 323H7, and the same CD3 binding domain 284A10, but have one of the 41BB binding domains 460C3, 420H5, and 466F6 and showed greater RTCC activity compared to the controls that do not contain one of the 41BB, PDL1, ROR1, or CD3 binding domains.

Example 7: Re-Directed T Cell Cytotoxicity (RTCC) Assay with Peripheral Blood Mononuclear Cells as Effectors and B-Acute Lymphoblastic Leukemia (B-ALL) Cell Line Kasumi-2 as Targets The tetra-specific-specific antibodies listed in TABLEs 3 and 4 were tested for RTCC activity against the B-ALL cell line Kasumi 2 using human peripheral blood mononuclear cells (PBMC) as effectors. The Kasumi 2 target cells, $5\times10^6$, were labeled with CFSE (Invitrogen, #C34554) at 0.5 M in 10 ml of culture media for 20 minutes at 37° C. The cells were washed 3 times with 50 ml of culture media before resuspending in 10 ml then counted again. Antibodies were prepared at 2× final concentration and titrated 1:3 across 10 wells of a 96 well plate in 200 ul of RPMI+10% FBS. Human PBMC were purified by standard ficoll density gradient from a “leukopak” which is an enriched leukapheresis product collected from normal human peripheral blood. In the final destination 96 well plate the target cells, PBMC, and serially titrated antibodies were combined by adding 100 μl of target cells (5,000), 50 ul of PBMC (25,000), and 100 ul of each antibody dilution to each well of the assay. The assay plate was incubated at 37° C. for approximately 72 hours and then the contents of each assay well were harvested and analyzed for the number of CFSE-labeled target cells remaining. As shown on FIG. 10, the tetra-specific GNC antibodies all contain the same PDL1 binding domain PL230C6, the same ROR1 binding domain 338H4, and the same CD3 binding domain 284A10, but have one of the 41BB binding domains 460C3, 420H5, and 466F6 and showed greater RTCC activity compared to the controls except for the control SI-35E36 which does not have a 41BB binding domain but appeared to be similarly potent at the tetra-specific GNC antibodies SI-35E18, 19, and 20.

Example 8: Re-Directed T Cell Cytotoxicity (RTCC) Assay with CD8+, CD45RO+ Memory T Cells as Effectors and B-Acute Lymphoblastic Leukemia (B-ALL) Cell Line Kasumi-2 as Targets The tetra-specific GNC antibodies listed in TABLEs 3 and 4 were tested for RTCC activity against the B-ALL cell line Kasumi 2 using human CD8+, CD45RO+ memory T cells as effectors. The Kasumi 2 target cells, $5\times10^6$, were labeled with CFSE (Invitrogen, #C34554) at 0.5 uM in 10 ml of culture media for 20 minutes at 37° C. The cells were washed 3 times with 50 ml of culture media before resuspending in 10 ml then counted again. Antibodies were prepared at 2× final concentration and titrated 1:3 across 10 wells of a 96 well plate in 200 ul of RPMI+10% FBS. Human CD8+, CD45RO+ memory T cells were enriched from PBMC from a normal donor using the EasySep™ Human Memory CD8+ T Cell Enrichment Kit (Stemcell Technologies, #19159) as per the manufacturers protocol. The final cell population was determined to be 98% CD8+, CD45RO+ T cells by FACS analysis (data not shown). In the final destination 96 well plate the target cells, T cells, and serially titrated antibodies were combined by adding 100 ul of target cells (5,000), 50 ul of CD8+, CD45RO+ memory T cells (25,000), and 100 ul of each antibody dilution to each well of the assay. The assay plate was incubated at 37° C. for approximately 72 hours and then the contents of each assay well were harvested and analyzed for the number of CFSE-labeled target cells remaining. As shown on FIG. 11, the tetra-specific GNC antibodies all contain the same PDL1 binding domain PL230C6, the same ROR1 binding domain 338H4, and the same CD3 binding domain 284A10, but have one of the 41BB binding domains 460C3, 420H5, and 466F6 and showed greater RTCC activity compared to the controls that do not contain one of the 41BB, PDL1, ROR1, or CD3 binding domains.

Example 9: Re-Directed T Cell Cytotoxicity (RTCC) Assay with CD8+, CD45RA+ Naive T Cells as Effectors and B-Acute Lymphoblastic Leukemia (B-ALL) Cell Line Kasumi-2 as Targets The tetra-specific GNC antibodies listed in TABLEs 3 and 4 were tested for RTCC activity against the B-ALL cell line Kasumi 2 using human CD8+, CD45RA+ memory T cells as effectors. The Kasumi 2 target cells, $5\times10^6$, were labeled with CFSE (Invitrogen, #C34554) at 0.5 uM in 10 ml of culture media for 20 minutes at 37° C. The cells were washed 3 times with 50 ml of culture media before resuspending in 10 ml then counted again. Antibodies were prepared at 2× final concentration and titrated 1:3 across 10 wells of a 96 well plate in 200 ul of RPMI+10% FBS. Human CD8+, CD45RA+ memory T cells were enriched from PBMC from a normal donor using the EasySep™ Human Naïve CD8+ T Cell Isolation Kit (Stemcell Technologies, #19258) as per the manufacturers protocol. The final cell population was determined to be 98% CD8+, CD45RA+ T cells by FACS analysis. In the final destination 96 well plate the target cells, T cells, and serially titrated antibodies were combined by adding 100 μl of target cells (5,000), 50 ul of CD8+, CD45RO+ T cells (25,000), and 100 ul of each antibody dilution to each well of the assay. The assay plate was incubated at 37° C. for approximately 72 hours and then the contents of each assay well were harvested and analyzed for the number of CFSE-labeled target cells remaining. As shown on FIG. 12, the tetra-specific GNC antibodies all contain the same PDL1 binding domain PL230C6, the same ROR1 binding domain 338H4, and the same CD3 binding domain 284A10, but have one of the 41BB binding domains 460C3, 420H5, and 466F6 but did not show greater RTCC activity compared to the controls that do not contain one of the 41BB, PDL1, ROR1, or CD3 binding domains. This is in contrast to the tetra-specific GNC antibodies described in Example 6 and shown in FIG. 6 that do show RTCC activity with CD8+, CD45RA+naïve T cells.

The term "antibody" is used in the broadest sense and specifically covers single monoclonal antibodies (including agonist and antagonist antibodies), antibody compositions with polyepitopic specificity, as well as antibody fragments (e.g., Fab, F(ab')2, and Fv), so long as they exhibit the desired biological activity. In some embodiments, the antibody may be monoclonal, polyclonal, chimeric, single chain, bispecific or bi-effective, simianized, human and humanized antibodies as well as active fragments thereof. Examples of active fragments of molecules that bind to known antigens include Fab, F(ab')2, scFv and Fv fragments, including the products of an Fab immunoglobulin expression library and epitope-binding fragments of any of the antibodies and fragments mentioned above. In some embodiments, antibody may include immunoglobulin molecules and immunologically active portions of immunoglobulin molecules, i.e. molecules that contain a binding site that immunospecifically bind an antigen. The immunoglobulin can be of any type (IgG, IgM, IgD, IgE, IgA and IgY) or class (IgG1, IgG2, IgG3, IgG4, IgA1 and IgA2) or subclasses of immunoglobulin molecule. In one embodiment, the antibody may be whole antibodies and any antigen-binding fragment derived from the whole antibodies. A typical antibody refers to heterotetrameric protein comprising typically of two heavy (H) chains and two light (L) chains. Each heavy chain is comprised of a heavy chain variable domain (abbreviated as VH) and a heavy chain constant domain. Each light chain is comprised of a light chain variable domain (abbreviated as VL) and a light chain constant domain. The VH and VL regions can be further subdivided into domains of hypervariable complementarity determining regions (CDR), and more conserved regions called framework regions (FR). Each variable domain (either VH or VL) is typically composed of three CDRs and four FRs, arranged in the following order: FR1, CDR1, FR2, CDR2, FR3, CDR3, FR4 from amino-terminus to carboxy-terminus. Within the variable regions of the light and heavy chains there are binding regions that interacts with the antigen.

The term "monoclonal antibody" as used herein refers to an antibody obtained from a population of substantially homogeneous antibodies, i.e., the individual antibodies comprising the population are identical except for possible naturally occurring mutations that may be present in minor amounts. Monoclonal antibodies are highly specific, being directed against a single antigenic site. Furthermore, in contrast to conventional (polyclonal) antibody preparations which typically include different antibodies directed against different determinants (epitopes), each monoclonal antibody is directed against a single determinant on the antigen. In addition to their specificity, the monoclonal antibodies are advantageous in that they are synthesized by the hybridoma culture, uncontaminated by other immunoglobulins. The modifier "monoclonal" indicates the character of the antibody as being obtained from a substantially homogeneous population of antibodies, and is not to be construed as requiring production of the antibody by any particular method. For example, the monoclonal antibodies to be used in accordance with the present disclosure may be made by the hybridoma method first described by Kohler & Milstein, Nature, 256:495(1975), or may be made by recombinant DNA methods (see, e.g., U.S. Pat. No. 4,816,567).

The monoclonal antibodies may include "chimeric" antibodies (immunoglobulins) in which a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, so long as they exhibit the desired biological activity (U.S. Pat. No. 4,816,567; and Morrison et al., Proc. Natl. Acad. Sci. USA, 81:6851-6855 [1984]).

Monoclonal antibodies can be produced using various methods including mouse hybridoma or phage display (see Siegel. Transfus. Clin. Biol. 9:15-22(2002) for a review) or from molecular cloning of antibodies directly from primary B cells (see Tiller. New Biotechnol. 28:453-7(2011)). In the present disclosure antibodies were created by the immunization of rabbits with both human PD-L1 protein and cells transiently expressing human PD-L1 on the cell surface.

Rabbits are known to create antibodies of high affinity, diversity and specificity (Weber et al. Exp. Mol. Med. 49: e305). B cells from immunized animals were cultured in vitro and screened for the production of anti-PD-L1 antibodies. The antibody variable genes were isolated using recombinant DNA techniques and the resulting antibodies were expressed recombinantly and further screened for desired features such as ability to inhibit the binding of PD-L1 to PD-1, the ability to bind to non-human primate PD-L1 and the ability to enhance human T-cell activation. This general method of antibody discovery is similar to that described in Seeber et al. PLOS One. 9: e86184(2014).

The term "antigen- or epitope-binding portion or fragment" refers to fragments of an antibody that are capable of binding to an antigen (PD-L1 in this case). These fragments may be capable of the antigen-binding function and additional functions of the intact antibody. Examples of binding fragments include, but are not limited to a single-chain Fv fragment (scFv) consisting of the VL and VH domains of a single arm of an antibody connected in a single polypeptide chain by a synthetic linker or a Fab fragment which is a monovalent fragment consisting of the VL, constant light (CL), VH and constant heavy 1 (CH1) domains. Antibody fragments can be even smaller sub-fragments and can consist of domains as small as a single CDR domain, in particular the CDR3 regions from either the VL and/or VH domains (for example see Beiboer et al., J. Mol. Biol. 296:833-49(2000)). Antibody fragments are produced using conventional methods known to those skilled in the art. The antibody fragments are can be screened for utility using the same techniques employed with intact antibodies.

The "antigen- or epitope-binding fragments" can be derived from an antibody of the present disclosure by a number of art-known techniques. For example, purified monoclonal antibodies can be cleaved with an enzyme, such as pepsin, and subjected to HPLC gel filtration. The appropriate fraction containing Fab fragments can then be collected and concentrated by membrane filtration and the like. For further description of general techniques for the isolation of active fragments of antibodies, see for example, Khaw, B. A. et al. J. Nucl. Med. 23:1011-1019(1982); Rousseaux et al. Methods Enzymology, 121:663-69, Academic Press, 1986.

Papain digestion of antibodies produces two identical antigen binding fragments, called "Fab" fragments, each with a single antigen binding site, and a residual "Fc" fragment, whose name reflects its ability to crystallize readily. Pepsin treatment yields an F(ab')2 fragment that has two antigen combining sites and is still capable of cross-linking antigen.

The Fab fragment may contain the constant domain of the light chain and the first constant domain (CH1) of the heavy chain. Fab' fragments differ from Fab fragments by the addition of a few residues at the carboxy terminus of the heavy chain CH1 domain including one or more cysteines from the antibody hinge region. Fab'-SH is the designation herein for Fab' in which the cysteine residue(s) of the constant domains bear a free thiol group. F(ab')2 antibody fragments originally were produced as pairs of Fab' fragments which have hinge cysteines between them. Other, chemical couplings of antibody fragments are also known.

"Fv" is the minimum antibody fragment which contains a complete antigen recognition and binding site. This region consists of a dimer of one heavy and one light chain variable domain in tight, non-covalent association. It is in this configuration that the three CDRs of each variable domain interact to define an antigen binding site on the surface of the VH-VL dimer. Collectively, the six CDRs confer antigen binding specificity to the antibody. However, even a single variable domain (or half of an Fv comprising only three CDRs specific for an antigen) has the ability to recognize and bind antigen, although at a lower affinity than the entire binding site.

The "light chains" of antibodies (immunoglobulins) from any vertebrate species can be assigned to one of two clearly distinct types, called kappa and lambda (A), based on the amino acid sequences of their constant domains.

Depending on the amino acid sequence of the constant domain of their heavy chains, immunoglobulins can be assigned to different classes. There are five major classes of immunoglobulins: IgA, IgD, IgE, IgG and IgM, and several of these may be further divided into subclasses (isotypes), e.g., IgG-1, IgG-2, IgG-3, and IgG-4; IgA-1 and IgA-2. The heavy chain constant domains that correspond to the different classes of immunoglobulins are called a, delta, epsilon, y, and u, respectively. The subunit structures and three-dimensional configurations of different classes of immunoglobulins are well known.

A "humanized antibody" refers to a type of engineered antibody having its CDRs derived from a non-human donor immunoglobulin, the remaining immunoglobulin-derived parts of the molecule being derived from one (or more) human immunoglobulin(s). In addition, framework support residues may be altered to preserve binding affinity. Methods to obtain "humanized antibodies" are well known to those skilled in the art. (see, e.g., Queen et al., Proc. Natl Acad Sci USA, 86:10029-10032(1989), Hodgson et al., Bio/Technology, 9:421(1991)). In one embodiment, the "humanized antibody" may be obtained by genetic engineering approach that enables production of affinity-matured humanlike polyclonal antibodies in large animals such as, for example, rabbits (see, e.g. U.S. Pat. No. 7,129,084).

The terms "polypeptide", "peptide", and "protein", as used herein, are interchangeable and are defined to mean a biomolecule composed of amino acids linked by a peptide bond.

The terms "a", "an" and "the" as used herein are defined to mean "one or more" and include the plural unless the context is inappropriate.

By "isolated" is meant a biological molecule free from at least some of the components with which it naturally occurs. "Isolated," when used to describe the various polypeptides disclosed herein, means a polypeptide that has been identified and separated and/or recovered from a cell or cell culture from which it was expressed. Ordinarily, an isolated polypeptide will be prepared by at least one purification step. An "isolated antibody," refers to an antibody which is substantially free of other antibodies having different antigenic specificities.

"Recombinant" means the antibodies are generated using recombinant nucleic acid techniques in exogeneous host cells.

The term "antigen" refers to an entity or fragment thereof which can induce an immune response in an organism, particularly an animal, more particularly a mammal including a human. The term includes immunogens and regions thereof responsible for antigenicity or antigenic determinants.

Also as used herein, the term "immunogenic" refers to substances which elicit or enhance the production of antibodies, T-cells or other reactive immune cells directed against an immunogenic agent and contribute to an immune response in humans or animals. An immune response occurs when an individual produces sufficient antibodies, T-cells and other reactive immune cells against administered immunogenic compositions of the present disclosure to moderate or alleviate the disorder to be treated.

"Specific binding" or "specifically binds to" or is "specific for" a particular antigen or an epitope means binding that is measurably different from a non-specific interaction. Specific binding can be measured, for example, by determining binding of a molecule compared to binding of a control molecule, which generally is a molecule of similar structure that does not have binding activity. For example, specific binding can be determined by competition with a control molecule that is similar to the target.

Specific binding for a particular antigen or an epitope can be exhibited, for example, by an antibody having a KD for an antigen or epitope of at least about 10-4 M, at least about 10-5 M, at least about 10-6 M, at least about 10-7 M, at least about 10-8 M, at least about 10-9, alternatively at least about 10-10 M, at least about 10-11 M, at least about 10-12 M, or greater, where KD refers to a dissociation rate of a particular antibody-antigen interaction. In some embodiments, an antibody that specifically binds an antigen will have a KD that is 20-, 50-, 100-, 500-, 1000-, 5,000-, 10,000- or more times greater for a control molecule relative to the antigen or epitope.

Also, specific binding for a particular antigen or an epitope can be exhibited, for example, by an antibody having a KA or Ka for an antigen or epitope of at least 20-, 50-, 100-, 500-, 1000-, 5,000-, 10,000- or more times greater for the epitope relative to a control, where KA or Ka refers to an association rate of a particular antibody-antigen interaction.

"Homology" between two sequences is determined by sequence identity. If two sequences which are to be compared with each other differ in length, sequence identity preferably relates to the percentage of the nucleotide residues of the shorter sequence which are identical with the nucleotide residues of the longer sequence. Sequence identity can be determined conventionally with the use of computer programs. The deviations appearing in the comparison between a given sequence and the above-described sequences of the disclosure may be caused for instance by addition, deletion, substitution, insertion or recombination.

While the present disclosure has been described with reference to particular embodiments or examples, it may be understood that the embodiments are illustrative and that the disclosure scope is not so limited. Alternative embodiments of the present disclosure may become apparent to those having ordinary skill in the art to which the present disclosure pertains. Such alternate embodiments are considered to be encompassed within the scope of the present disclosure. Accordingly, the scope of the present disclosure is defined by the appended claims and is supported by the foregoing description. All references cited or referred to in this disclosure are hereby incorporated by reference in their entireties.

Guidance and Navigation Control Proteins and Method of Making and Using Thereof

SEQUENCE LIST

| SEQ ID | Description |
|---|---|
| 1 | anti-CD3 284A10 VHv1 nt |
| 2 | anti-CD3 284A10 VHv1 aa |
| 3 | anti-CD3 284A10 VLv1 nt |
| 4 | anti-CD3 284A10 VLv1 aa |
| 5 | anti-CD3 480C8 VHv1 nt |
| 6 | anti-CD3 480C8 VHv1 aa |
| 7 | anti-CD3 480C8 VLv1 nt |
| 8 | anti-CD3 480C8 VLv1 aa |
| 9 | anti-PD-L1 PL230C6 VHv3 nt |
| 10 | anti-PD-L1 PL230C6 VHv3 aa |
| 11 | anti-PD-L1 PL230C6 VLv2 nt |
| 12 | anti-PD-L1 PL230C6 VLv2 aa |
| 13 | anti-4-1BB 420H5 VHv3 nt |
| 14 | anti-4-1BB 420H5 VHv3 aa |
| 15 | anti-4-1BB 420H5 VLv3 nt |
| 16 | anti-4-1BB 420H5 VHLv3 aa |
| 17 | anti-4-1BB 466F6 VHv2 nt |
| 18 | anti-4-1BB 466F6 VHv2 aa |
| 19 | anti-4-1BB 466F6 VLv5 nt |
| 20 | anti-4-1BB 466F6 VLv5 aa |

-continued

| SEQUENCE LIST | |
|---|---|
| SEQ ID | Description |
| 21 | anti-4-1BB 460C3 VHv1 nt |
| 22 | anti-4-1BB 460C3 VHv1 aa |
| 23 | anti-4-1BB 460C3 VLv1 nt |
| 24 | anti-4-1BB 460C3 VLv1 aa |
| 25 | anti-ROR1 324C6 VHv2 nt |
| 26 | anti-ROR1 324C6 VHv2 aa |
| 27 | anti-ROR1 324C6 VLv1 nt |
| 28 | anti-ROR1 324C6 VLv1 aa |
| 29 | anti-ROR1 323H7 VHv4 nt |
| 30 | anti-ROR1 323H7 VHv4 aa |
| 31 | anti-ROR1 323H7 VLv1 nt |
| 32 | anti-ROR1 323H7 VLv1 aa |
| 33 | anti-ROR1 338H4 VHv3 nt |
| 34 | anti-ROR1 338H4 VHv3 aa |
| 35 | anti-ROR1 338H4 VLv4 nt |
| 36 | anti-ROR1 338H4 VLv4 aa |
| 37 | anti-ROR1 330F11 VHv1 nt |
| 38 | anti-ROR1 330F11 VHv1 aa |
| 39 | anti-ROR1 330F11 VLv1 nt |
| 40 | anti-ROR1 330F11 VLv1 aa |
| 41 | anti-FITC 4-4-20 VH nt |
| 42 | anti-FITC 4-4-20 VH aa |
| 43 | anti-FITC 4-4-20 VL nt |
| 44 | anti-FITC 4-4-20 VL aa |
| 45 | human IgG1 null2 (G1m-fa with ADCC/CDC null mutations) nt |
| 46 | human IgG1 null2 (G1m-fa with ADCC/CDC null mutations) aa |
| 47 | human Ig Kappa nt |
| 48 | human Ig Kappa aa |
| 49 | SI-35E18 (460C3-L1H1-scFv × PL230C6-Fab × 323H7-H4L1-scFv × 284A10-H1L1-scFv) heavy chain nt |
| 50 | SI-35E18 (460C3-L1H1-scFv × PL230C6-Fab × 323H7-H4L1-scFv × 284A10-H1L1-scFv) heavy chain aa |
| 51 | SI-35E18 (460C3-L1H1-scFv × PL230C6-Fab × 323H7-H4L1-scFv × 284A10-H1L1-scFv) light chain nt |
| 52 | SI-35E18 (460C3-L1H1-scFv × PL230C6-Fab × 323H7-H4L1-scFv × 284A10-H1L1-scFv) light chain aa |

>SEQ ID 01 anti-CD3 284A10 VHv1 nt
GAGGTGCAGCTGGTGGAGTCTGGGGGAGGCTTGGTCCAGCCTGGGGGGTCCCTGAGACTCTCCTGTGCAGCCTC
TGGATTCACCATCAGTACCAATGCAATGAGCTGGGTCCGCCAGGCTCCAGGGAAGGGGCTGGAGTGGATCGGAG
TCATTACTGGTCGTGATATCACATACTACGCGAGCTGGGCGAAAGGCAGATTCACCATCTCCAGAGACAATTCCAA
GAACACGCTGTATCTTCAAATGAACAGCCTGAGAGCCGAGGACACGGCTGTGTATTACTGTGCGCGCGACGGTGG
ATCATCTGCTATTACTAGTAACAACATTTGGGGCCAAGGAACTCTGGTCACCGTTTCTTCA >SEQ ID 02 anti-CD3 284A10 VHv1 aa
EVQLVESGGGLVQPGGSLRLSCAASGFTISTNAMSWVRQAPGKGLEWIGVITGRDITYYASWAKGRFTISRDNSKNTLY -continued

SEQUENCE LIST

SEQ ID Description

LQMNSLRAEDTAVYYCARDGGSSAITSNNIWGQGTLVTVSS

>SEQ ID 03 anti-CD3 284A10 VLv1 nt
GACGTCGTGATGACCCAGTCTCCTTCCACCCTGTCTGCATCTGTAGGAGACAGAGTCACCATCAATTGCCAAGCCA
GTGAGAGCATTAGCAGTTGGTTAGCCTGGTATCAGCAGAAACCAGGGAAAGCCCCTAAGCTCCTGATCTATGAAG
CATCCAAACTGGCATCTGGGGTCCCATCAAGGTTCAGCGGCAGTGGATCTGGGACAGAGTTCACTCTCACCATCA
GCAGCCTGCAGCCTGATGATTTTGCAACTTATTACTGCCAAGGCTATTTTTATTTTATTAGTCGTACTTATGTAAATT
CTTTCGGCGGAGGGACCAAGGTGGAGATCAAA >SEQ ID 04 anti-CD3 284A10 VLv1 aa
DVVMTQSPSTLSASVGDRVTINCQASESISSWLAWYQQKPGKAPKLLIYEASKLASGVPSRFSGSGSGTEFTLTISSLQPD
DFATYYCQGYFYFISRTYVNSFGGGTKVEIK >SEQ ID 05 anti-CD3 480C8 VHv1 nt
GAGGTGCAGCTGGTGGAGTCTGGGGGAGGCTTGGTCCAGCCTGGGGGGTCCCTGAGACTCTCCTGTGCAGCCTC
TGGAATCGACCTCAGTAGCAATGCAATGAGCTGGGTCCGCCAGGCTCCAGGGAAGGGGCTGGAGTGGATCGGAG
TCATTACTGGTCGTGATATCACATACTACGCGAGCTGGGCGAAAGGCAGATTCACCATCTCCAGAGACAATTCCAA
GAACACGCTGTATCTTCAAATGAACAGCCTGAGAGCCGAGGACACGGCTGTGTATTACTGTGCGCGCGACGGTGG
ATCATCTGCTATTAATAGTAAGAACATTTGGGGCCAAGGAACTCTGGTCACCGTTTCTTCA >SEQ ID 06 anti-CD3 480C8 VHv1 aa
EVQLVESGGGLVQPGGSLRLSCAASGIDLSSNAMSWVRQAPGKGLEWIGVITGRDITYYASWAKGRFTISRDNSKNTLY
LQMNSLRAEDTAVYYCARDGGSSAINSKNIWGQGTLVTVSS >SEQ ID 07 anti-CD3 480C8 VLv1 nt
GACATCCAGATGACCCAGTCTCCTTCCACCCTGTCTGCATCTGTAGGAGACAGAGTCACCATCACTTGCCAAGCCA
GTGAGAGCATTAGCAGTTGGTTAGCCTGGTATCAGCAGAAACCAGGGAAAGCCCCTAAGCTCCTGATCTATGAAG
CATCCAAACTGGCATCTGGGGTCCCATCAAGGTTCAGCGGCAGTGGATCTGGGACAGAGTTCACTCTCACCATCA
GCAGCCTGCAGCCTGATGATTTTGCAACTTATTACTGCCAAGGCTATTTTTATTTTATTAGTCGTACTTATGTAAATG
CTTTCGGCGGAGGGACCAAGGTGGAGATCAAA >SEQ ID 08 anti-CD3 480C8 VLv1 aa
DIQMTQSPSTLSASVGDRVTITCQASESISSWLAWYQQKPGKAPKLLIYEASKLASGVPSRFSGSGSGTEFTLTISSLQPD
DFATYYCQGYFYFISRTYVNAFGGGTKVEIK >SEQ ID 09 anti-PD-L1 PL230C6 VHv3 nt
CAGTCGGTGGAGGAGTCTGGGGGAGGCTTGGTCCAGCCTGGGGGGTCCCTGAGACTCTCCTGTACAGCCTCTGG
AATCGACCTTAATACCTACGACATGATCTGGGTCCGCCAGGCTCCAGGCAAGGGGCTAGAGTGGGTTGGAATCAT
TACTTATAGTGGTAGTAGATACTACGCGAACTGGGCGAAAGGCCGATTCACCATCTCCAAAGACAATACCAAGAA
CACGGTGTATCTGCAAATGAACAGCCTGAGAGCTGAGGACACGGCTGTGTATTACTGTGCCAGAGATTATATGAG
TGGTTCCCACTTGTGGGGCCAGGGAACCCTGGTCACCGTCTCTAGT >SEQ ID 10 anti-PD-L1 PL230C6 VHv3 aa
QSVEESGGGLVQPGGSLRLSCTASGIDLNTYDMIWVRQAPGKGLEWVGIITYSGSRYYANWAKGRFTISKDNTKNTVY
LQMNSLRAEDTAVYYCARDYMSGSHLWGQGTLVTVSS >SEQ ID 11 anti-PD-L1 PL230C6 VLv2 nt
GCCTATGATATGACCCAGTCTCCATCTTCCGTGTCTGCATCTGTAGGAGACAGAGTCACCATCAAGTGTCAGGCCA
GTGAGGACATTTATAGCTTCTTGGCCTGGTATCAGCAGAAACCAGGGAAAGCCCCTAAGCTCCTGATCCATTCTGC
ATCCTCTCTGGCATCTGGGGTCCCATCAAGGTTCAGCGGCAGTGGATCTGGGACAGATTTCACTCTCACCATCAGC
AGCCTGCAGCCTGAAGATTTTGCAACTTACTATTGTCAACAGGGTTATGGTAAAAATAATGTTGATAATGCTTTCG
GCGGAGGGACCAAGGTGGAGATCAAA >SEQ ID 12 anti-PD-L1 PL230C6 VLv2 aa
AYDMTQSPSSVSASVGDRVTIKCQASEDIYSFLAWYQQKPGKAPKLLIHSASSLASGVPSRFSGSGSGTDFTLTISSLQPE
DFATYYCQQGYGKNNVDNAFGGGTKVEIK >SEQ ID 13 anti-4-1BB 420H5 VHv3 nt
CAGTCGCTGGTGGAGTCTGGGGGAGGCTTGGTACAGCCTGGGGGGTCCCTGAGACTCTCCTGTGCAGCCTCTGG
ATTCTCCTTCAGTAGCAACTACTGGATATGCTGGGTCCGCCAGGCTCCAGGGAAGGGGCTGGAGTGGATCGCATG
CATTTATGTTGGTAGTAGTGGTGACACTTACTACGCGAGCTCCGCGAAAGGCCGGTTCACCATCTCCAGAGACAAT
TCCAAGAACACGCTGTATCTGCAAATGAACAGCCTGAGAGCCGAGGACACGGCCGTATATTACTGTGCGAGAGAT
AGTAGTAGTTATTATATGTTTAACTTGTGGGGCCAGGGAACCCTGGTCACCGTCTCGAGC >SEQ ID 14 anti-4-1BB 420H5 VHv3 aa
QSLVESGGGLVQPGGSLRLSCAASGFSFSSNYWICWVRQAPGKGLEWIACIYVGSSGDTYYASSAKGRFTISRDNSKNT
LYLQMNSLRAEDTAVYYCARDSSSYYMFNLWGQGTLVTVSS >SEQ ID 15 anti-4-1BB 420H5 VLv3 nt
GCCCTTGTGATGACCCAGTCTCCTTCCACCCTGTCTGCATCTGTAGGAGACAGAGTCACCATCAATTGCCAGGCCA
GTGAGGACATTGATACCTATTTAGCCTGGTATCAGCAGAAACCAGGGAAAGCCCCTAAGCTCCTGATCTTTTATGC
ATCCGATCTGGCATCTGGGGTCCCATCAAGGTTCAGCGGCAGTGGATCTGGGACAGAATTCACTCTCACCATCAGC
AGCCTGCAGCCTGATGATTTTGCAACTTATTACTGCCAAGGCGGTTACTATACTAGTAGTGCTGATACGAGGGGTG
CTTTCGGCGGAGGGACCAAGGTGGAGATCAAA -continued

| SEQUENCE LIST |
|---|
| SEQ ID Description |

>SEQ ID 16 anti-4-1BB 420H5 VLv3 aa
ALVMTQSPSTLSASVGDRVTINCQASEDIDTYLAWYQQKPGKAPKLLIFYASDLASGVPSRFSGSGSGTEFTLTISSLQPD
DFATYYCQGGYYTSSADTRGAFGGGTKVEIK >SEQ ID 17 anti-4-1BB 466F6 VHv2 nt
CGGTCGCTGGTGGAGTCTGGGGGAGGCTTGGTCCAGCCTGGGGGGTCCCTGAGACTCTCCTGTACAGCCTCTGGA
TTCACCATCAGTAGCTACCACATGCAGTGGGTCCGCCAGGCTCCAGGGAAGGGGCTGGAGTACATCGGAACCATT
AGTAGTGGTGGTAATGTATACTACGCGAGCTCCGCGAGAGGCAGATTCACCATCTCCAGACCCTCGTCCAAGAAC
ACGGTGGATCTTCAAATGAACAGCCTGAGAGCCGAGGACACGGCTGTGTATTACTGTGCGAGAGACTCTGGTTAT
AGTGATCCTATGTGGGGCCAGGGAACCCTGGTCACCGTCTCGAGC >SEQ ID 18 anti-4-1BB 466F6 VHv2 aa
RSLVESGGGLVQPGGSLRLSCTASGFTISSYHMQWVRQAPGKGLEYIGTISSGGNVYYASSARGRFTISRPSSKNTVDLQ
MNSLRAEDTAVYYCARDSGYSDPMWGQGTLVTVSS >SEQ ID 19 anti-4-1BB 466F6 VLv5 nt
GACGTTGTGATGACCCAGTCTCCATCTTCCGTGTCTGCATCTGTAGGAGACAGAGTCACCATCACCTGTCAGGCCA
GTCAGAACATTAGGACTTACTTATCCTGGTATCAGCAGAAACCAGGGAAAGCCCCTAAGCTCCTGATCTATGCTGC
AGCCAATCTGGCATCTGGGGTCCCATCAAGGTTCAGCGGCAGTGGATCTGGGACAGATTTCACTCTCACCATCAGC
GACCTGGAGCCTGGCGATGCTGCAACTTACTATTGTCAGTCTACCTATCTTGGTACTGATTATGTTGGCGGTGCTTT
CGGCGGAGGGACCAAGGTGGAGATCAAA >SEQ ID 20 anti-4-1BB 466F6 VLv5 aa
DVVMTQSPSSVSASVGDRVTITCQASQNIRTYLSWYQQKPGKAPKLLIYAAANLASGVPSRFSGSGSGTDFTLTISDLEP
GDAATYYCQSTYLGTDYVGGAFGGGTKVEIK >SEQ ID 21 anti-4-1BB 460C3 VHv1 nt
GAGGTGCAGCTGTTGGAGTCTGGGGGAGGCTTGGTACAGCCTGGGGGGTCCCTGAGACTCTCCTGTGCAGCCTCT
GGAATCGACTTCAGTAGGAGATACTACATGTGCTGGGTCCGCCAGGCTCCAGGGAAGGGGCTGGAGTGGATCGC
ATGCATATATACTGGTAGCCGCGATACTCCTCACTACGCGAGCTCCGCGAAAGGCCGGTTCACCATCTCCAGAGAC
AATTCCAAGAACACGCTGTATCTGCAAATGAACAGCCTGAGAGCCGAGGACACGGCCGTATATTACTGTGCGAGA
GAAGGTAGCCTGTGGGGCCAGGGAACCCTGGTCACCGTCTCGAGC >SEQ ID 22 anti-4-1BB 460C3 VHv1 aa
EVQLLESGGGLVQPGGSLRLSCAASGIDFSRRYYMCWVRQAPGKGLEWIACIYTGSRDTPHYASSAKGRFTISRDNSKN
TLYLQMNSLRAEDTAVYYCAREGSLWGQGTLVTVSS >SEQ ID 23 anti-4-1BB 460C3 VLv1 nt
GACATCCAGATGACCCAGTCTCCTTCCACCCTGTCTGCATCTGTAGGAGACAGAGTCACCATCACTTGCCAGTCCA
GTCAGAGTGTTTATAGTAACTGGTTCTCCTGGTATCAGCAGAAACCAGGGAAAGCCCCTAAGCTCCTGATCTATTC
TGCATCCACTCTGGCATCTGGGGTCCCATCAAGGTTCAGCGGCAGTGGATCTGGGACAGAATTCACTCTCACCATC
AGCAGCCTGCAGCCTGATGATTTTGCAACTTATTACTGCGCAGGCGGTTACAATACTGTTATTGATACTTTTGCTTT
CGGCGGAGGGACCAAGGTGGAGATCAAA >SEQ ID 24 anti-4-1BB 460C3 VLv1 aa
DIQMTQSPSTLSASVGDRVTITCQSSQSVYSNWFSWYQQKPGKAPKLLIYSASTLASGVPSRFSGSGSGTEFTLTISSLQP
DDFATYYCAGGYNTVIDTFAFGGGTKVEIK >SEQ ID 25 anti-ROR1 324C6 VHv2 nt
CAGTCGCTGGTGGAGTCTGGGGGAGGCTTGGTCCAGCCTGGGGGGTCCCTGAGACTCTCCTGTACTGCCTCTGGA
TTCTCCCTCAGTAGGTACTACATGACCTGGGTCCGCCAGGCTCCAGGGAAGGGGCTGGAGTGGATCGGAACCATT
TATACTAGTGGTAGTACATGGTACGCGAGCTGGACAAAAGGCAGATTCACCATCTCCAAAGACAATACCAAGAAC
ACGGTGGATCTTCAAATGAACAGCCTGAGAGCCGAGGACACGGCTGTGTATTACTGTGCGAGATCCTATTATGGC
GGTGATAAGACTGGTTTAGGCATCTGGGGCCAGGGAACTCTGGTTACCGTCTCTTCA >SEQ ID 26 anti-ROR1 324C6 VHv2 nt
QSLVESGGGLVQPGGSLRLSCTASGFSLSRYYMTWVRQAPGKGLEWIGTIYTSGSTWYASWTKGRFTISKDNTKNTVD
LQMNSLRAEDTAVYYCARSYYGGDKTGLGIWGQGTLVTVSS >SEQ ID 27 anti-ROR1 324C6 VLv1 nt
GACATCCAGATGACCCAGTCTCCTTCCACCCTGTCTGCATCTGTAGGAGACAGAGTCACCATCACTTGCCAGGCCA
GTCAGAGCATTGATAGTTGGTTATCCTGGTATCAGCAGAAACCAGGGAAAGCCCCTAAGCTCCTGATCTATCAGGC
ATCCACTCTGGCATCTGGGGTCCCATCAAGGTTCAGCGGCAGTGGATCTGGGACAGAGTTCACTCTCACCATCAGC
AGCCTGCAGCCTGATGATTTTGCAACTTATTACTGCCAATCTGCTTATGGTGTTAGTGGTACTAGTAGTTATTTATA
TACTTTCGGCGGAGGGACCAAGGTGGAGATCAAA >SEQ ID 28 anti-ROR1 324C6 VLv1 aa
DIQMTQSPSTLSASVGDRVTITCQASQSIDSWLSWYQQKPGKAPKLLIYQASTLASGVPSRFSGSGSGTEFTLTISSLQPD
DFATYYCQSAYGVSGTSSYLYTFGGGTKVEIK >SEQ ID 29 anti-ROR1 323H7 VHv4 nt
GAGGTGCAGCTGTTGGAGTCTGGGGGAGGCTTGGTACAGCCTGGGGGGTCCCTGAGACTCTCCTGTGCAGCCTCT
GGATTCACCATCAGTCGCTACCACATGACTTGGGTCCGCCAGGCTCCAGGGAAGGGGCTGGAGTGGATCGGACAT -continued

SEQUENCE LIST

SEQ ID Description

ATTTATGTTAATAATGATGACACAGACTACGCGAGCTCCGCGAAAGGCCGGTTCACCATCTCCAGAGACAATTCCA
AGAACACGCTGTATCTGCAAATGAACAGCCTGAGAGCCGAGGACACGGCCACCTATTTCTGTGCGAGATTGGATG
TTGGTGGTGGTGGTGCTTATATTGGGGACATCTGGGGCCAGGGAACTCTGGTTACCGTCTCTTCA

>SEQ ID 30 anti-ROR1 323H7 VHv4 aa
EVQLLESGGGLVQPGGSLRLSCAASGFTISRYHMTWVRQAPGKGLEWIGHIYVNNDDTDYASSAKGRFTISRDNSKNT
LYLQMNSLRAEDTATYFCARLDVGGGGAYIGDIWGQGTLVTVSS >SEQ ID 31 anti-ROR1 323H7 VLv1 nt
GACATCCAGATGACCCAGTCTCCATCCTCCCTGTCTGCATCTGTAGGAGACAGAGTCACCATCACTTGCCAGTCCA
GTCAGAGTGTTTATAACAACAACGACTTAGCCTGGTATCAGCAGAAACCAGGGAAAGTTCCTAAGCTCCTGATCTA
TTATGCTTCCACTCTGGCATCTGGGGTCCCATCTCGGTTCAGTGGCAGTGGATCTGGGACAGATTTCACTCTCACCA
TCAGCAGCCTGCAGCCTGAAGATGTTGCAACTTATTACTGTGCAGGCGGTTATGATACGGATGGTCTTGATACGTT
TGCTTTCGGCGGAGGGACCAAGGTGGAGATCAAA >SEQ ID 32 anti-ROR1 323H7 VLv1 aa
DIQMTQSPSSLSASVGDRVTITCQSSQSVYNNNDLAWYQQKPGKVPKLLIYYASTLASGVPSRFSGSGSGTDFTLTISSL
QPEDVATYYCAGGYDTDGLDTFAFGGGTKVEIK >SEQ ID 33 anti-ROR1 338H4 VHv3 nt
GAGGTGCAGCTGGTGGAGTCTGGGGGAGGCTTGGTCCAGCCTGGGGGGTCCCTGAGACTCTCCTGTACTGCCTCT
GGATTCTCCCTCAGTAGCTATGCAATGAGCTGGGTCCGCCAGGCTCCAGGGAGGGGGCTGGAGTGGATCGGAAT
CATTTATGCTAGTGGTAGCACATACTACGCGAGCTCGGCGAAAGGCAGATTCACCATCTCCAAAGACAATACCAAG
AACACGGTGGATCTTCAAATGAACAGCCTGAGAGCCGAGGACACGGCTGTGTATTACTGTGCGAGAATTTATGAC
GGCATGGACCTCTGGGGCCAGGGAACTCTGGTTACCGTCTCTTCA >SEQ ID 34 anti-ROR1 338H4 VHv3 aa
EVQLVESGGGLVQPGGSLRLSCTASGFSLSSYAMSWVRQAPGRGLEWIGIIYASGSTYYASSAKGRFTISKDNTKNTVDL
QMNSLRAEDTAVYYCARIYDGMDLWGQGTLVTVSS >SEQ ID 35 anti-ROR1 338H4 VLv4 nt
GACATCCAGATGACCCAGTCTCCATCCTCCCTGTCTGCATCTGTAGGAGACAGAGTCACCATCAATTGCCAGGCCA
GTCAGAACATTTACAGCTACTTATCCTGGTATCAGCAGAAACCAGGGAAAGTTCCTAAGCGCCTGATCTATCTGGC
ATCTACTCTGGCATCTGGGGTCCCATCTCGGTTCAGTGGCAGTGGATCTGGGACAGATTACACTCTCACCATCAGC
AGCCTGCAGCCTGAAGATGTTGCAACTTATTACTGTCAAAGCAATTATAACGGTAATTATGGTTTCGGCGGAGGGA
CCAAGGTGGAGATCAAA >SEQ ID 36 anti-ROR1 338H4 VLv4 aa
DIQMTQSPSSLSASVGDRVTINCQASQNIYSYLSWYQQKPGKVPKRLIYLASTLASGVPSRFSGSGSGTDYTLTISSLQPE
DVATYYCQSNYNGNYGFGGGTKVEIK >SEQ ID 37 anti-ROR1 330F11 VHv1 nt
GAGGTGCAGCTGGTGGAGTCTGGGGGAGGCTTGGTCCAGCCTGGGGGGTCCCTGAGACTCTCCTGTGCAGCCTC
TGGATTCTCCCTCAATAACTACTGGATGAGCTGGGTCCGCCAGGCTCCAGGGAAGGGGCTGGAGTGGATCGGAA
CCATTAGTAGTGGTGCGTATACATGGTTCGCCACCTGGGCGACAGGCAGATTCACCATCTCCAGAGACAATTCCAA
GAACACGCTGTATCTTCAAATGAACAGCCTGAGAGCCGAGGACACGGCTGTGTATTACTGTGCGAGATATTCTTCT
ACTACTGATTGGACCTACTTTAACATCTGGGGCCAGGGAACTCTGGTTACCGTCTCTTCA >SEQ ID 38 anti-ROR1 330F11 VHv1 aa
EVQLVESGGGLVQPGGSLRLSCAASGFSLNNYWMSWVRQAPGKGLEWIGTISSGAYTWFATWATGRFTISRDNSKN
TLYLQMNSLRAEDTAVYYCARYSSTTDWTYFNIWGQGTLVTVSS >SEQ ID 39 anti-ROR1 330F11 VLv1 nt
GACATCCAGATGACCCAGTCTCCTTCCACCCTGTCTGCATCTGTAGGAGACAGAGTCACCATCACTTGCCAGGCCA
GTCAGAGCATTAATAACTACTTAGCCTGGTATCAGCAGAAACCAGGGAAAGCCCCTAAGCTCCTGATCTATAGGGC
ATCCACTCTGGAATCTGGGGTCCCATCAAGGTTCAGCGGCAGTGGATCTGGGACAGAATTCACTCTCACCATCAGC
AGCCTGCAGCCTGATGATTTTGCAACTTATTACTGCCAAAGCTATAATGGTGTTGGTAGGACTGCTTTCGGCGGAG
GGACCAAGGTGGAGATCAAA >SEQ ID 40 anti-ROR1 330F11 VLv1 aa
DIQMTQSPSTLSASVGDRVTITCQASQSINNYLAWYQQKPGKAPKLLIYRASTLESGVPSRFSGSGSGTEFTLTISSLQPD
DFATYYCQSYNGVGRTAFGGGTKVEIK >SEQ ID 41 anti-FITC 4-4-20 VH nt
GAGGTGAAGCTGGATGAGACTGGAGGAGGCTTGGTGCAACCTGGGAGGCCCATGAAACTCTCCTGTGTTGCCTCT
GGATTCACTTTTAGTGACTACTGGATGAACTGGGTCCGCCAGTCTCCAGAGAAAGGACTGGAGTGGGTAGCACAA
ATTAGAAACAAACCTTATAATTATGAAACATATTATTCAGATTCTGTGAAAGGCAGATTCACCATCTCAAGAGATG
ATTCCAAAAGTAGTGTCTACCTGCAAATGAACAACTTAAGAGTTGAAGACATGGGTATCTATTACTGTACGGGTTC
TTACTATGGTATGGACTACTGGGGTCAAGGAACCTCAGTCACCGTCTCCTCA >SEQ ID 42 anti-FITC 4-4-20 VH aa
EVKLDETGGGLVQPGRPMKLSCVASGFTFSDYWMNWVRQSPEKGLEWVAQIRNKPYNYETYYSDSVKGRFTISRDDS
KSSVYLQMNNLRVEDMGIYYCTGSYYGMDYWGQGTSVTVSS -continued

| SEQUENCE LIST |
| --- |
| SEQ ID Description |

>SEQ ID 43 anti-FITC 4-4-20 VL nt
GATGTCGTGATGACCCAAACTCCACTCTCCCTGCCTGTCAGTCTTGGAGATCAAGCCTCCATCTCTTGCAGATCTAG
TCAGAGCCTTGTACACAGTAATGGAAACACCTATTTACGTTGGTACCTGCAGAAGCCAGGCCAGTCTCCAAAGGTC
CTGATCTACAAAGTTTCCAACCGATTTTCTGGGGTCCCAGACAGGTTCAGTGGCAGTGGATCAGGGACAGATTTCA
CACTCAAGATCAGCAGAGTGGAGGCTGAGGATCTGGGAGTTTATTTCTGCTCTCAAAGTACACATGTTCCGTGGAC
GTTCGGTGGAGGCACCAAGCTGGAAATCAAA >SEQ ID 44 anti-FITC 4-4-20 VL aa
DVVMTQTPLSLPVSLGDQASISCRSSQSLVHSNGNTYLRWYLQKPGQSPKVLIYKVSNRFSGVPDRFSGSGSGTDFTLKI
SRVEAEDLGVYFCSQSTHVPWTFGGGTKLEIK >SEQ ID 45 human IgG1 null (G1m-fa with ADCC/CDC null mutations) nt
GCTAGCACCAAGGGCCCATCGGTCTTCCCCCTGGCACCCTCCTCCAAGAGCACCTCTGGGGGCACAGCGGCCCTG
GGCTGCCTGGTCAAGGACTACTTCCCCGAACCGGTGACGGTGTCGTGGAACTCAGGCGCCCTGACCAGCGGCGTG
CACACCTTCCCGGCTGTCCTACAGTCCTCAGGACTCTACTCCCTCAGCAGCGTGGTGACCGTGCCCTCCAGCAGCTT
GGGCACCCAGACCTACATCTGCAACGTGAATCACAAGCCCAGCAACACCAAGGTGGACAAGAGAGTTGAGCCCA
AATCTTGTGACAAAACTCACACATGCCCACCGTGCCCAGCACCTGAAGCCGCGGGGGCACCGTCAGTCTTCCTCTT
CCCCCCAAAACCCAAGGACACCCTCATGATCTCCCGGACCCCTGAGGTCACATGCGTGGTGGTGGACGTGAGCCA
CGAAGACCCTGAGGTCAAGTTCAACTGGTACGTGGACGGCGTGGAGGTGCATAATGCCAAGACAAAGCCGCGGG
AGGAGCAGTACAACAGCACGTACCGTGTGGTCAGCGTCCTCACCGTCCTGCACCAGGACTGGCTGAATGGCAAGG
AGTACAAGTGCGCGGTCTCCAACAAAGCCCTCCCAGCCCCCATCGAGAAAACCATCTCCAAAGCCAAAGGGCAGC
CCCGAGAACCACAGGTGTACACCCTGCCCCCATCCCGGGATGAGCTGACCAAGAACCAGGTCAGCCTGACCTGCC
TGGTCAAAGGCTTCTATCCCAGCGACATCGCCGTGGAGTGGGAGAGCAATGGGCAGCCGGAGAACAACTACAAG
ACCACGCCTCCCGTGCTGGACTCCGACGGCTCCTTCTTCCTCTATAGCAAGCTCACCGTGGACAAGAGCAGGTGGC
AGCAGGGGAACGTCTTCTCATGCTCCGTGATGCATGAGGCTCTGCACAACCACTACACGCAGAAGAGCCTCTCCCT
GTCTCCGGGT >SEQ ID 46 human IgG1 null (G1m-fa with ADCC/CDC null mutations) aa
ASTKGPSVFPLAPSSKSTSGGTAALGCLVKDYFPEPVTVSWNSGALTSGVHTFPAVLQSSGLYSLSSVVTVPSSSLGTQTY
ICNVNHKPSNTKVDKRVEPKSCDKTHTCPPCPAPEAAGAPSVFLFPPKPKDTLMISRTPEVTCVVVDVSHEDPEVKFNW
YVDGVEVHNAKTKPREEQYNSTYRVVSVLTVLHQDWLNGKEYKCAVSNKALPAPIEKTISKAKGQPREPQVYTLPPSRD
ELTKNQVSLTCLVKGFYPSDIAVEWESNGQPENNYKTTPPVLDSDGSFFLYSKLTVDKSRWQQGNVFSCSVMHEALHN
HYTQKSLSLSPG >SEQ ID 47 human Ig Kappa nt
CGTACGGTGGCTGCACCATCTGTCTTCATCTTCCCGCCATCTGATGAGCAGTTGAAATCTGGAACTGCCTCTGTTGT
GTGCCTGCTGAATAACTTCTATCCCAGAGAGGCCAAAGTACAGTGGAAGGTGGATAACGCCCTCCAATCGGGTAA
CTCCCAGGAGAGTGTCACAGAGCAGGACAGCAAGGACAGCACCTACAGCCTCAGCAGCACCCTGACGCTGAGCA
AAGCAGACTACGAGAAACACAAAGTCTACGCCTGCGAAGTCACCCATCAGGGCCTGAGCTCGCCCGTCACAAAGA
GCTTCAACAGGGGAGAGTGT >SEQ ID 48 human Ig Kappa aa
RTVAAPSVFIFPPSDEQLKSGTASVVCLLNNFYPREAKVQWKVDNALQSGNSQESVTEQDSKDSTYSLSSTLTLSKADYE
KHKVYACEVTHQGLSSPVTKSFNRGEC >SEQ ID 49 SI-35E18 (460C3-L1H1-scFv × PL230C6-Fab × 323H7-H4L1-scFv × 284A10-H1L1-scFv) heavy chain nt
GACATCCAGATGACCCAGTCTCCTTCCACCCTGTCTGCATCTGTAGGAGACAGAGTCACCATCACTTGCCAGTCCA
GTCAGAGTGTTTATAGTAACTGGTTCTCCTGGTATCAGCAGAAACCAGGGAAAGCCCCTAAGCTCCTGATCTATTC
TGCATCCACTCTGGCATCTGGGGTCCCATCAAGGTTCAGCGGCAGTGGATCTGGGACAGAATTCACTCTCACCATC
AGCAGCCTGCAGCCTGATGATTTTGCAACTTATTACTGCGCAGGCGGTTACAATACTGTTATTGATACTTTTGCTTT
CGGCGGAGGGACCAAGGTGGAGATCAAAGGCGGTGGCGGTAGTGGGGGAGGCGGTTCTGGCGGCGGAGGGTC
CGGCGGTGGAGGATCAGAGGTGCAGCTGTTGGAGTCTGGGGGAGGCTTGGTACAGCCTGGGGGGTCCCTGAGA
CTCTCCTGTGCAGCCTCTGGAATCGACTTCAGTAGGAGATACTACATGTGCTGGGTCCGCCAGGCTCCAGGGAAG
GGGCTGGAGTGGATCGCATGCATATATACTGGTAGCCGCGATACTCCTCACTACGCGAGCTCCGCGAAAGGCCGG
TTCACCATCTCCAGAGACAATTCCAAGAACACGCTGTATCTGCAAATGAACAGCCTGAGAGCCGAGGACACGGCC
GTATATTACTGTGCGAGAGAAGGTAGCCTGTGGGGCCAGGGAACCCTGGTCACCGTCTCGAGCGGCGGTGGAGG
GTCCGGCGGTGGTGGATCCCAGTCGGTGGAGGAGTCTGGGGGAGGCTTGGTCCAGCCTGGGGGGTCCCTGAGA
CTCTCCTGTACAGCCTCTGGAATCGACCTTAATACCTACGACATGATCTGGGTCCGCCAGGCTCCAGGCAAGGGGC
TAGAGTGGGTTGGAATCATTACTTATAGTGGTAGTAGATACTACGCGAACTGGGCGAAAGGCCGATTCACCATCT
CCAAAGACAATACCAAGAACACGGTGTATCTGCAAATGAACAGCCTGAGAGCTGAGGACACGGCTGTGTATTACT
GTGCCAGAGATTATATGAGTGGTTCCCACTTGTGGGGCCAGGGAACCCTGGTCACCGTCTCTAGTGCTAGCACCA
AGGGCCCATCGGTCTTCCCCCTGGCACCCTCCTCCAAGAGCACCTCTGGGGGCACAGCGGCCCTGGGCTGCCTGG
TCAAGGACTACTTCCCCGAACCGGTGACGGTGTCGTGGAACTCAGGCGCCCTGACCAGCGGCGTGCACACCTTCC
CGGCTGTCCTACAGTCCTCAGGACTCTACTCCCTCAGCAGCGTGGTGACCGTGCCCTCCAGCAGCTTGGGCACCCA
GACCTACATCTGCAACGTGAATCACAAGCCCAGCAACACCAAGGTGGACAAGAGAGTTGAGCCCAAATCTTGTGA
CAAAACTCACACATGCCCACCGTGCCCAGCACCTGAAGCCGCGGGGGCACCGTCAGTCTTCCTCTTCCCCCCAAAA
CCCAAGGACACCCTCATGATCTCCCGGACCCCTGAGGTCACATGCGTGGTGGTGGACGTGAGCCACGAAGACCCT
GAGGTCAAGTTCAACTGGTACGTGGACGGCGTGGAGGTGCATAATGCCAAGACAAAGCCGCGGGAGGAGCAGT
ACAACAGCACGTACCGTGTGGTCAGCGTCCTCACCGTCCTGCACCAGGACTGGCTGAATGGCAAGGAGTACAAGT
GCGCGGTCTCCAACAAAGCCCTCCCAGCCCCCATCGAGAAAACCATCTCCAAAGCCAAAGGGCAGCCCCGAGAAC
CACAGGTGTATACCCTGCCCCCATCCCGGGATGAGCTGACCAAGAACCAGGTCAGCCTGACCTGCCTGGTCAAAG
GCTTCTATCCCAGCGACATCGCCGTGGAGTGGGAGAGCAATGGGCAGCCGGAGAACAACTACAAGACCACGCCT
CCCGTGCTGGACTCCGACGGCTCCTTCTTCCTCTATAGCAAGCTCACCGTGGACAAGAGCAGGTGGCAGCAGGGG -continued

SEQUENCE LIST

SEQ ID Description

AACGTCTTCTCATGCTCCGTGATGCATGAGGCTCTGCACAACCACTACACGCAGAAGAGCCTCTCCCTGTCTCCGG
GTGGCGGTGGAGGGTCCGGCGGTGGTGGATCCGAGGTGCAGCTGTTGGAGTCTGGGGGAGGCTTGGTACAGCC
TGGGGGGTCCCTGAGACTCTCCTGTGCAGCCTCTGGATTCACCATCAGTCGCTACCACATGACTTGGGTCCGCCAG
GCTCCAGGGAAGGGGCTGGAGTGGATCGGACATATTTATGTTAATAATGATGACACAGACTACGCGAGCTCCGCG
AAAGGCCGGTTCACCATCTCCAGAGACAATTCCAAGAACACGCTGTATCTGCAAATGAACAGCCTGAGAGCCGAG
GACACGGCCACCTATTTCTGTGCGAGATTGGATGTTGGTGGTGGTGGTGCTTATATTGGGGACATCTGGGGCCAG
GGAACTCTGGTTACCGTCTCTTCAGGCGGTGGCGGTAGTGGGGGAGGCGGTTCTGGCGGCGGAGGGTCCGGCG
GTGGAGGATCAGACATCCAGATGACCCAGTCTCCATCCTCCCTGTCTGCATCTGTAGGAGACAGAGTCACCATCAC
TTGCCAGTCCAGTCAGAGTGTTTATAACAACAACGACTTAGCCTGGTATCAGCAGAAACCAGGGAAAGTTCCTAAG
CTCCTGATCTATTATGCTTCCACTCTGGCATCTGGGGTCCCATCTCGGTTCAGTGGCAGTGGATCTGGGACAGATTT
CACTCTCACCATCAGCAGCCTGCAGCCTGAAGATGTTGCAACTTATTACTGTGCAGGCGGTTATGATACGGATGGT
CTTGATACGTTTGCTTTCGGCGGAGGGACCAAGGTGGAGATCAAAGGCGGTGGAGGGTCCGGCGGTGGTGGATC
CGAGGTGCAGCTGGTGGAGTCTGGGGGAGGCTTGGTCCAGCCTGGGGGGTCCCTGAGACTCTCCTGTGCAGCCT
CTGGATTCACCATCAGTACCAATGCAATGAGCTGGGTCCGCCAGGCTCCAGGGAAGGGGCTGGAGTGGATCGGA
GTCATTACTGGTCGTGATATCACATACTACGCGAGCTGGGCGAAAGGCAGATTCACCATCTCCAGAGACAATTCCA
AGAACACGCTGTATCTTCAAATGAACAGCCTGAGAGCCGAGGACACGGCTGTGTATTACTGTGCGCGCGACGGTG
GATCATCTGCTATTACTAGTAACAACATTTGGGGCCAAGGAACTCTGGTCACCGTTTCTTCAGGCGGTGGCGGTAG
TGGGGGAGGCGGTTCTGGCGGCGGAGGGTCCGGCGGTGGAGGATCAGACGTCGTGATGACCCAGTCTCCTTCCA
CCCTGTCTGCATCTGTAGGAGACAGAGTCACCATCAATTGCCAAGCCAGTGAGAGCATTAGCAGTTGGTTAGCCTG
GTATCAGCAGAAACCAGGGAAAGCCCCTAAGCTCCTGATCTATGAAGCATCCAAACTGGCATCTGGGGTCCCATC
AAGGTTCAGCGGCAGTGGATCTGGGACAGAGTTCACTCTCACCATCAGCAGCCTGCAGCCTGATGATTTTGCAACT
TATTACTGCCAAGGCTATTTTTATTTTATTAGTCGTACTTATGTAAATTCTTTCGGCGGAGGGACCAAGGTGGAGAT
CAAA

>SEQ ID 50 SI-35E18 (460C3-L1H1-scFv × PL230C6-Fab × 323H7-H4L1-scFv × 284A10-H1L1-scFv) heavy chain aa
DIQMTQSPSTLSASVGDRVTITCQSSQSVYSNWFSWYQQKPGKAPKLLIYSASTLASGVPSRFSGSGSGTEFTLTISSLQP
DDFATYYCAGGYNTVIDTFAFGGGTKVEIKGGGGSGGGGSGGGGSGGGGSEVQLLESGGGLVQPGGSLRLSCAASGI
DFSRRYYMCWVRQAPGKGLEWIACIYTGSRDTPHYASSAKGRFTISRDNSKNTLYLQMNSLRAEDTAVYYCAREGSLW
GQGTLVTVSSGGGGSGGGGSQSVEESGGGLVQPGGSLRLSCTASGIDLNTYDMIWVRQAPGKGLEWVGIITYSGSRYY
ANWAKGRFTISKDNTKNTVYLQMNSLRAEDTAVYYCARDYMSGSHLWGQGTLVTVSSASTKGPSVFPLAPSSKSTSG
GTAALGCLVKDYFPEPVTVSWNSGALTSGVHTFPAVLQSSGLYSLSSVVTVPSSSLGTQTYICNVNHKPSNTKVDKRVEP
KSCDKTHTCPPCPAPEAAGAPSVFLFPPKPKDTLMISRTPEVTCVVVDVSHEDPEVKFNWYVDGVEVHNAKTKPREEQ
YNSTYRVVSVLTVLHQDWLNGKEYKCAVSNKALPAPIEKTISKAKGQPREPQVYTLPPSRDELTKNQVSLTCLVKGFYPS
DIAVEWESNGQPENNYKTTPPVLDSDGSFFLYSKLTVDKSRWQQGNVFSCSVMHEALHNHYTQKSLSLSPGGGGGSG
GGGSEVQLLESGGGLVQPGGSLRLSCAASGFTISRYHMTWVRQAPGKGLEWIGHIYVNNDDTDYASSAKGRFTISRDN
SKNTLYLQMNSLRAEDTATYFCARLDVGGGGAYIGDIWGQGTLVTVSSGGGGSGGGGSGGGGSGGGGSDIQMTQS
PSSLSASVGDRVTITCQSSQSVYNNNDLAWYQQKPGKVPKLLIYYASTLASGVPSRFSGSGSGTDFTLTISSLQPEDVATY
YCAGGYDTDGLDTFAFGGGTKVEIKGGGGSGGGGSEVQLVESGGGLVQPGGSLRLSCAASGFTISTNAMSWVRQAP
GKGLEWIGVITGRDITYYASWAKGRFTISRDNSKNTLYLQMNSLRAEDTAVYYCARDGGSSAITSNNIWGQGTLVTVSS
GGGGSGGGGSGGGGSGGGGSDVVMTQSPSTLSASVGDRVTINCQASESISSWLAWYQQKPGKAPKLLIYEASKLASG
VPSRFSGSGSGTEFTLTISSLQPDDFATYYCQGYFYFISRTYVNSFGGGTKVEIK >SEQ ID 51 SI-35E18 (460C3-L1H1-scFv × PL230C6-Fab × 323H7-H4L1-scFv × 284A10-H1L1-scFv) light chain nt
GCCTATGATATGACCCAGTCTCCATCTTCCGTGTCTGCATCTGTAGGAGACAGAGTCACCATCAAGTGTCAGGCCA
GTGAGGACATTTATAGCTTCTTGGCCTGGTATCAGCAGAAACCAGGGAAAGCCCCTAAGCTCCTGATCCATTCTGC
ATCCTCTCTGGCATCTGGGGTCCCATCAAGGTTCAGCGGCAGTGGATCTGGGACAGATTTCACTCTCACCATCAGC
AGCCTGCAGCCTGAAGATTTTGCAACTTACTATTGTCAACAGGGTTATGGTAAAAATAATGTTGATAATGCTTTCG
GCGGAGGGACCAAGGTGGAGATCAAACGTACGGTGGCTGCACCATCTGTCTTCATCTTCCCGCCATCTGATGAGC
AGTTGAAATCTGGAACTGCCTCTGTTGTGTGCCTGCTGAATAACTTCTATCCCAGAGAGGCCAAAGTACAGTGGAA
GGTGGATAACGCCCTCCAATCGGGTAACTCCCAGGAGAGTGTCACAGAGCAGGACAGCAAGGACAGCACCTACA
GCCTCAGCAGCACCCTGACGCTGAGCAAAGCAGACTACGAGAAACACAAAGTCTACGCCTGCGAAGTCACCCATC
AGGGCCTGAGCTCGCCCGTCACAAAGAGCTTCAACAGGGGAGAGTGT >SEQ ID 52 SI-35E18 (460C3-L1H1-scFv × PL230C6-Fab × 323H7-H4L1-scFv × 284A10-H1L1-scFv) light chain aa
AYDMTQSPSSVSASVGDRVTIKCQASEDIYSFLAWYQQKPGKAPKLLIHSASSLASGVPSRFSGSGSGTDFTLTISSLQPE
DFATYYCQQGYGKNNVDNAFGGGTKVEIKRTVAAPSVFIFPPSDEQLKSGTASVVCLLNNFYPREAKVQWKVDNALQS
GNSQESVTEQDSKDSTYSLSSTLTLSKADYEKHKVYACEVTHQGLSSPVTKSFNRGEC CDR's underlined in amino acid sequences >SEQ ID 53 CDR-HC1 from SEQ ID 22
RRYYMC >SEQ ID 54 CDR-HC2 from SEQ ID 22
CIYTGSRDTPHYASSAKG >SEQ ID 55 CDR-HC3 from SEQ ID 22
EGSL -continued >SEQ ID 56 CDR-LC1 from SEQ ID 24
QSSQSVYSNWFS >SEQ ID 57 CDR-LC2 from SEQ ID 24
SASTLAS >SEQ ID 58 CDR-LC3 from SEQ ID 24
AGGYNTVIDTFA -continued >SEQ ID 59 CDR-HC1 from SEQ ID 10
TYDMI >SEQ ID 60 CDR-HC2 from SEQ ID 10
IITYSGSRYYANWAKG >SEQ ID 61 CDR-HC3 from SEQ ID 10
DYMSGSHL >SEQ ID 62 CDR-LC1 from SEQ ID 12
QASEDIYSFLA >SEQ ID 63 CDR-LC2 from SEQ ID 12
SASSLAS >SEQ ID 64 CDR-LC3 from SEQ ID 12
QQGYGKNNVDNA >SEQ ID 65 CDR-HC1 from SEQ ID 30
RYHMT >SEQ ID 66 CDR-HC2 from SEQ ID 30
HIYVNNDDTDYASSAKG >SEQ ID 67 CDR-HC3 from SEQ ID 30
LDVGGGGAYIGDI -continued >SEQ ID 68 CDR-LC1 from SEQ ID 32
QSSQSVYNNNDLA >SEQ ID 69 CDR-LC2 from SEQ ID 32
YASTLAS >SEQ ID 70 CDR-LC3 from SEQ ID 32
AGGYDTDGLDTFA >SEQ ID 71 CDR-HC1 from SEQ ID 2
TNAMS >SEQ ID 72 CDR-HC2 from SEQ ID 2
VITGRDITYYASWAKG >SEQ ID 73 CDR-HC3 from SEQ ID 2
DGGSSAITSNNI >SEQ ID 74 CDR-LC1 from SEQ ID 4
QASESISSWLA >SEQ ID 75 CDR-LC2 from SEQ ID 4
EASKLAS >SEQ ID 76 CDR-LC3 from SEQ ID 4
QGYFYFISRTYVNS

What we claim is:

1. A guidance and navigation control (GNC) protein, comprising a cytotoxic cell binding moiety and a cancer-targeting moiety, wherein the cytotoxic cell binding moiety has a binding specificity to a T-cell receptor, a NK cell receptor, a macrophage receptor, a dendritic cell receptor, or a combination thereof, and wherein the cancer-targeting moiety has a binding specificity to a cancer cell receptor, wherein the GNC protein comprises the amino acid sequences of SEQ ID NO: 50 and SEQ ID NO: 52.

2. The GNC protein of claim 1, wherein the T-cell receptor comprises CD3.

3. The GNC protein of claim 1, wherein the NK cell receptor comprises 4-1BB.

4. The GNC protein of claim 1, wherein the macrophage receptor comprises PD-L1.

5. The GNC protein of claim 1, wherein the dendritic cell receptor comprises PDL1 or 4-1BB.

6. The GNC protein of claim 1, wherein the cancer cell receptor is a receptor on a lung cancer cell, a liver cancer cell, a breast cancer cell, a colorectal cancer cell, an anal cancer cell, a pancreatic cancer cell, a gallbladder cancer cell, a bile duct cancer cell, a head and neck cancer cell, a nasopharyngeal cancer cell, a skin cancer cell, a melanoma cell, an ovarian cancer cell, a prostate cancer cell, a urethral cancer cell, a lung cancer cell, a non-small cell lung cancer cell, a small cell lung cancer cell, a brain tumour cell, a glioma cell, a neuroblastoma cell, an esophageal cancer cell, a gastric cancer cell, a liver cancer cell, a kidney cancer cell, a bladder cancer cell, a cervical cancer cell, an endometrial cancer cell, a thyroid cancer cell, an eye cancer cell, a sarcoma cell, a bone cancer cell, a leukemia cell, a myeloma cell, a lymphoma cell, or a combination thereof.

7. The GNC protein of claim 1, wherein the cancer cell receptor comprises ROR1.

8. The GNC protein of claim 1, wherein the GNC protein is capable of activating a T-cell by binding the cytotoxic cell binding moiety to the T-cell receptor.

9. The GNC protein of claim 1, comprising a tetra-specific antibody or antibody monomer.

10. A therapeutic complex, comprising the GNC protein of claim 1 and a cytotoxic cell, wherein the cytotoxic cell comprises a T cell, a NK cell, a macrophage, a dendritic cell, or a combination thereof.

11. A therapeutic complex, comprising the GNC protein of claim 1 and a cancer cell.

12. A therapeutic complex, comprising the GNC protein of claim 1, a T-cell bound to the T-cell binding moiety and a cancer cell bound to the cancer-targeting moiety.

13. A pharmaceutical composition, comprising the therapeutic complex of claim 10 and a pharmaceutically acceptable carrier.

* * * * *

SEQUENCE LISTING

<160> NUMBER OF SEQ ID NOS: 52

<210> SEQ ID NO 1
<211> LENGTH: 360
<212> TYPE: DNA
<213> ORGANISM: Artificial Sequence
<220> FEATURE:
<223> OTHER INFORMATION: Synthesized

<400> SEQUENCE: 1
gaggtgcagc tggtggagtc tgggggaggc ttggtccagc ctgggggtc cctgagactc 60 tcctgtgcag cctctggatt caccatcagt accaatgcaa tgagctgggt ccgccaggct 120
ccagggaagg ggctggagtg gatcggagtc attactggtc gtgatatcac atactacgcg 180
agctgggcga aaggcagatt caccatctcc agagacaatt ccaagaacac gctgtatctt 240
caaatgaaca gcctgagagc cgaggacacg gctgtgtatt actgtgcgcg cgacggtgga 300
tcatctgcta ttactagtaa caacatttgg ggccaaggaa ctctggtcac cgtttcttca 360

<210> SEQ ID NO 2
<211> LENGTH: 120
<212> TYPE: PRT
<213> ORGANISM: Artificial Sequence
<220> FEATURE:
<223> OTHER INFORMATION: Synthesized

<400> SEQUENCE: 2

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Ile Ser Thr Asn
            20                  25                  30

Ala Met Ser Trp Val Arg Gln Ala Pro Gly Lys Gly Leu Glu Trp Ile
        35                  40                  45

Gly Val Ile Thr Gly Arg Asp Ile Thr Tyr Tyr Ala Ser Trp Ala Lys
    50                  55                  60

Gly Arg Phe Thr Ile Ser Arg Asp Asn Ser Lys Asn Thr Leu Tyr Leu
65                  70                  75                  80
```

Gln Met Asn Ser Leu Arg Ala Glu Asp Thr Ala Val Tyr Tyr Cys Ala
85 90 95

Arg Asp Gly Gly Ser Ser Ala Ile Thr Ser Asn Asn Ile Trp Gly Gln
100 105 110

Gly Thr Leu Val Thr Val Ser Ser
115 120

<210> SEQ ID NO 3
<211> LENGTH: 336
<212> TYPE: DNA
<213> ORGANISM: Artificial Sequence
<220> FEATURE:
<223> OTHER INFORMATION: Synthesized

<400> SEQUENCE: 3
gacgtcgtga tgacccagtc tccttccacc ctgtctgcat ctgtaggaga cagagtcacc 60
atcaattgcc aagccagtga gagcattagc agttggttag cctggtatca gcagaaacca 120
gggaaagccc ctaagctcct gatctatgaa gcatccaaac tggcatctgg ggtcccatca 180
aggttcagcg gcagtggatc tgggacagag ttcactctca ccatcagcag cctgcagcct 240
gatgattttg caacttatta ctgccaaggc tatttttatt ttattagtcg tacttatgta 300
aattctttcg gcggagggac caaggtggag atcaaa 336

<210> SEQ ID NO 4
<211> LENGTH: 112
<212> TYPE: PRT
<213> ORGANISM: Artificial Sequence
<220> FEATURE:
<223> OTHER INFORMATION: Synthesized

<400> SEQUENCE: 4

Asp Val Val Met Thr Gln Ser Pro Ser Thr Leu Ser Ala Ser Val Gly
1 5 10 15

Asp Arg Val Thr Ile Asn Cys Gln Ala Ser Glu Ser Ile Ser Ser Trp
20 25 30

Leu Ala Trp Tyr Gln Gln Lys Pro Gly Lys Ala Pro Lys Leu Leu Ile
35 40 45

Tyr Glu Ala Ser Lys Leu Ala Ser Gly Val Pro Ser Arg Phe Ser Gly
50 55 60

Ser Gly Ser Gly Thr Glu Phe Thr Leu Thr Ile Ser Ser Leu Gln Pro
65 70 75 80

Asp Asp Phe Ala Thr Tyr Tyr Cys Gln Gly Tyr Phe Tyr Phe Ile Ser
85 90 95

Arg Thr Tyr Val Asn Ser Phe Gly Gly Gly Thr Lys Val Glu Ile Lys
100 105 110

<210> SEQ ID NO 5
<211> LENGTH: 360
<212> TYPE: DNA
<213> ORGANISM: Artificial Sequence
<220> FEATURE:
<223> OTHER INFORMATION: Synthesized

<400> SEQUENCE: 5
gaggtgcagc tggtggagtc tgggggaggc ttggtccagc ctgggggggtc cctgagactc 60 tcctgtgcag cctctggaat cgacctcagt agcaatgcaa tgagctgggt ccgccaggct 120
ccagggaagg ggctggagtg gatcggagtc attactggtc gtgatatcac atactacgcg 180

```
agctgggcga aaggcagatt caccatctcc agagacaatt ccaagaacac gctgtatctt    240

caaatgaaca gcctgagagc cgaggacacg gctgtgtatt actgtgcgcg cgacggtgga    300

tcatctgcta ttaatagtaa gaacatttgg ggccaaggaa ctctggtcac cgtttcttca    360


<210> SEQ ID NO 6
<211> LENGTH: 120
<212> TYPE: PRT
<213> ORGANISM: Artificial Sequence
<220> FEATURE:
<223> OTHER INFORMATION: Synthesized

<400> SEQUENCE: 6

Glu Val Gln Leu Val Glu Ser Gly Gly Gly Leu Val Gln Pro Gly Gly
1               5                   10                  15

Ser Leu Arg Leu Ser Cys Ala Ala Ser Gly Ile Asp Leu Ser Ser Asn
            20                  25                  30

Ala Met Ser Trp Val Arg Gln Ala Pro Gly Lys Gly Leu Glu Trp Ile
        35                  40                  45

Gly Val Ile Thr Gly Arg Asp Ile Thr Tyr Tyr Ala Ser Trp Ala Lys
    50                  55                  60

Gly Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Tyr Cys Ala
                85                  90                  95

Arg Asp Gly Gly Ser Ser Ala Ile Asn Ser Lys Asn Ile Trp Gly Gln
            100                 105                 110

Gly Thr Leu Val Thr Val Ser Ser
        115                 120


<210> SEQ ID NO 7
<211> LENGTH: 336
<212> TYPE: DNA
<213> ORGANISM: Artificial Sequence
<220> FEATURE:
<223> OTHER INFORMATION: Synthesized

<400> SEQUENCE: 7

gacatccaga tgacccagtc tccttccacc ctgtctgcat ctgtaggaga cagagtcacc     60

atcacttgcc aagccagtga gagcattagc agttggttag cctggtatca gcagaaacca    120

gggaaagccc ctaagctcct gatctatgaa gcatccaaac tggcatctgg ggtcccatca    180

aggttcagcg gcagtggatc tgggacagag ttcactctca ccatcagcag cctgcagcct    240

gatgattttg caacttatta ctgccaaggc tatttttatt ttattagtcg tacttatgta    300

aatgctttcg gcggagggac caaggtggag atcaaa                              336


<210> SEQ ID NO 8
<211> LENGTH: 112
<212> TYPE: PRT
<213> ORGANISM: Artificial Sequence
<220> FEATURE:
<223> OTHER INFORMATION: Synthesized

<400> SEQUENCE: 8

Asp Ile Gln Met Thr Gln Ser Pro Ser Thr Leu Ser Ala Ser Val Gly
1               5                   10                  15

Asp Arg Val Thr Ile Thr Cys Gln Ala Ser Glu Ser Ile Ser Ser Trp
            20                  25                  30

Leu Ala Trp Tyr Gln Gln Lys Pro Gly Lys Ala Pro Lys Leu Leu Ile
```

```
        35                  40                  45

Tyr Glu Ala Ser Lys Leu Ala Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Asp Asp Phe Ala Thr Tyr Tyr Cys Gln Gly Tyr Phe Tyr Phe Ile Ser
                85                  90                  95

Arg Thr Tyr Val Asn Ala Phe Gly Gly Gly Thr Lys Val Glu Ile Lys
            100                 105                 110


<210> SEQ ID NO 9
<211> LENGTH: 345
<212> TYPE: DNA
<213> ORGANISM: Artificial Sequence
<220> FEATURE:
<223> OTHER INFORMATION: Synthesized

<400> SEQUENCE: 9

cagtcggtgg aggagtctgg gggaggcttg gtccagcctg gggggtccct gagactctcc     60

tgtacagcct ctggaatcga ccttaatacc tacgacatga tctgggtccg ccaggctcca    120

ggcaaggggc tagagtgggt tggaatcatt acttatagtg gtagtagata ctacgcgaac    180

tgggcgaaag gccgattcac catctccaaa gacaatacca agaacacggt gtatctgcaa    240

atgaacagcc tgagagctga ggacacggct gtgtattact gtgccagaga ttatatgagt    300

ggttcccact tgtggggcca gggaaccctg gtcaccgtct ctagt                    345


<210> SEQ ID NO 10
<211> LENGTH: 115
<212> TYPE: PRT
<213> ORGANISM: Artificial Sequence
<220> FEATURE:
<223> OTHER INFORMATION: Synthesized

<400> SEQUENCE: 10

Gln Ser Val Glu Glu Ser Gly Gly Gly Leu Val Gln Pro Gly Gly Ser
1               5                   10                  15

Leu Arg Leu Ser Cys Thr Ala Ser Gly Ile Asp Leu Asn Thr Tyr Asp
            20                  25                  30

Met Ile Trp Val Arg Gln Ala Pro Gly Lys Gly Leu Glu Trp Val Gly
        35                  40                  45

Ile Ile Thr Tyr Ser Gly Ser Arg Tyr Tyr Ala Asn Trp Ala Lys Gly
    50                  55                  60

Arg Phe Thr Ile Ser Lys Asp Asn Thr Lys Asn Thr Val Tyr Leu Gln
65                  70                  75                  80

Met Asn Ser Leu Arg Ala Glu Asp Thr Ala Val Tyr Tyr Cys Ala Arg
                85                  90                  95

Asp Tyr Met Ser Gly Ser His Leu Trp Gly Gln Gly Thr Leu Val Thr
            100                 105                 110

Val Ser Ser
        115


<210> SEQ ID NO 11
<211> LENGTH: 330
<212> TYPE: DNA
<213> ORGANISM: Artificial Sequence
<220> FEATURE:
<223> OTHER INFORMATION: Synthesized

<400> SEQUENCE: 11
```

```
gcctatgata tgacccagtc tccatcttcc gtgtctgcat ctgtaggaga cagagtcacc     60

atcaagtgtc aggccagtga ggacatttat agcttcttgg cctggtatca gcagaaacca    120

gggaaagccc ctaagctcct gatccattct gcatcctctc tggcatctgg ggtcccatca    180

aggttcagcg gcagtggatc tgggacagat ttcactctca ccatcagcag cctgcagcct    240

gaagattttg caacttacta ttgtcaacag ggttatggta aaaataatgt tgataatgct    300

ttcggcggag ggaccaaggt ggagatcaaa                                     330


<210> SEQ ID NO 12
<211> LENGTH: 110
<212> TYPE: PRT
<213> ORGANISM: Artificial Sequence
<220> FEATURE:
<223> OTHER INFORMATION: Synthesized

<400> SEQUENCE: 12

Ala Tyr Asp Met Thr Gln Ser Pro Ser Ser Val Ser Ala Ser Val Gly
1               5                   10                  15

Asp Arg Val Thr Ile Lys Cys Gln Ala Ser Glu Asp Ile Tyr Ser Phe
            20                  25                  30

Leu Ala Trp Tyr Gln Gln Lys Pro Gly Lys Ala Pro Lys Leu Leu Ile
        35                  40                  45

His Ser Ala Ser Ser Leu Ala Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Gly Tyr Gly Lys Asn Asn
                85                  90                  95

Val Asp Asn Ala Phe Gly Gly Gly Thr Lys Val Glu Ile Lys
            100                 105                 110


<210> SEQ ID NO 13
<211> LENGTH: 360
<212> TYPE: DNA
<213> ORGANISM: Artificial Sequence
<220> FEATURE:
<223> OTHER INFORMATION: Synthesized

<400> SEQUENCE: 13

cagtcgctgg tggagtctgg gggaggcttg gtacagcctg gggggtccct gagactctcc     60

tgtgcagcct ctggattctc cttcagtagc aactactgga tatgctgggt ccgccaggct    120

ccagggaagg ggctggagtg gatcgcatgc atttatgttg gtagtagtgg tgacacttac    180

tacgcgagct ccgcgaaagg ccggttcacc atctccagag acaattccaa gaacacgctg    240

tatctgcaaa tgaacagcct gagagccgag gacacggccg tatattactg tgcgagagat    300

agtagtagtt attatatgtt taacttgtgg ggccagggaa ccctggtcac cgtctcgagc    360


<210> SEQ ID NO 14
<211> LENGTH: 120
<212> TYPE: PRT
<213> ORGANISM: Artificial Sequence
<220> FEATURE:
<223> OTHER INFORMATION: Synthesized

<400> SEQUENCE: 14

Gln Ser Leu Val Glu Ser Gly Gly Gly Leu Val Gln Pro Gly Gly Ser
1               5                   10                  15
```

```
Leu Arg Leu Ser Cys Ala Ala Ser Gly Phe Ser Phe Ser Ser Asn Tyr
            20                  25                  30

Trp Ile Cys Trp Val Arg Gln Ala Pro Gly Lys Gly Leu Glu Trp Ile
        35                  40                  45

Ala Cys Ile Tyr Val Gly Ser Ser Gly Asp Thr Tyr Tyr Ala Ser Ser
    50                  55                  60

Ala Lys Gly Arg Phe Thr Ile Ser Arg Asp Asn Ser Lys Asn Thr Leu
65                  70                  75                  80

Tyr Leu Gln Met Asn Ser Leu Arg Ala Glu Asp Thr Ala Val Tyr Tyr
                85                  90                  95

Cys Ala Arg Asp Ser Ser Ser Tyr Tyr Met Phe Asn Leu Trp Gly Gln
            100                 105                 110

Gly Thr Leu Val Thr Val Ser Ser
        115                 120


<210> SEQ ID NO 15
<211> LENGTH: 336
<212> TYPE: DNA
<213> ORGANISM: Artificial Sequence
<220> FEATURE:
<223> OTHER INFORMATION: Synthesized

<400> SEQUENCE: 15

gcccttgtga tgacccagtc tccttccacc ctgtctgcat ctgtaggaga cagagtcacc     60

atcaattgcc aggccagtga ggacattgat acctatttag cctggtatca gcagaaacca    120

gggaaagccc ctaagctcct gatcttttat gcatccgatc tggcatctgg ggtcccatca    180

aggttcagcg gcagtggatc tgggacagaa ttcactctca ccatcagcag cctgcagcct    240

gatgattttg caacttatta ctgccaaggc ggttactata ctagtagtgc tgatacgagg    300

ggtgctttcg gcggagggac caaggtggag atcaaa                              336


<210> SEQ ID NO 16
<211> LENGTH: 112
<212> TYPE: PRT
<213> ORGANISM: Artificial Sequence
<220> FEATURE:
<223> OTHER INFORMATION: Synthesized

<400> SEQUENCE: 16

Ala Leu Val Met Thr Gln Ser Pro Ser Thr Leu Ser Ala Ser Val Gly
1               5                   10                  15

Asp Arg Val Thr Ile Asn Cys Gln Ala Ser Glu Asp Ile Asp Thr Tyr
            20                  25                  30

Leu Ala Trp Tyr Gln Gln Lys Pro Gly Lys Ala Pro Lys Leu Leu Ile
        35                  40                  45

Phe Tyr Ala Ser Asp Leu Ala Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Asp Asp Phe Ala Thr Tyr Tyr Cys Gln Gly Gly Tyr Tyr Thr Ser Ser
                85                  90                  95

Ala Asp Thr Arg Gly Ala Phe Gly Gly Gly Thr Lys Val Glu Ile Lys
            100                 105                 110


<210> SEQ ID NO 17
<211> LENGTH: 345
<212> TYPE: DNA
<213> ORGANISM: Artificial Sequence
```

<220> FEATURE:
<223> OTHER INFORMATION: Synthesized

<400> SEQUENCE: 17

```
cggtcgctgg tggagtctgg gggaggcttg gtccagcctg gggggtccct gagactctcc      60

tgtacagcct ctggattcac catcagtagc taccacatgc agtgggtccg ccaggctcca     120

gggaaggggc tggagtacat cggaaccatt agtagtggtg gtaatgtata ctacgcgagc     180

tccgcgagag gcagattcac catctccaga ccctcgtcca agaacacggt ggatcttcaa     240

atgaacagcc tgagagccga ggacacggct gtgtattact gtgcgagaga ctctggttat     300

agtgatccta tgtggggcca gggaaccctg gtcaccgtct cgagc                     345
```

<210> SEQ ID NO 18
<211> LENGTH: 115
<212> TYPE: PRT
<213> ORGANISM: Artificial Sequence
<220> FEATURE:
<223> OTHER INFORMATION: Synthesized

<400> SEQUENCE: 18

```
Arg Ser Leu Val Glu Ser Gly Gly Gly Leu Val Gln Pro Gly Gly Ser
1               5                   10                  15

Leu Arg Leu Ser Cys Thr Ala Ser Gly Phe Thr Ile Ser Ser Tyr His
            20                  25                  30

Met Gln Trp Val Arg Gln Ala Pro Gly Lys Gly Leu Glu Tyr Ile Gly
        35                  40                  45

Thr Ile Ser Ser Gly Gly Asn Val Tyr Tyr Ala Ser Ser Ala Arg Gly
    50                  55                  60

Arg Phe Thr Ile Ser Arg Pro Ser Ser Lys Asn Thr Val Asp Leu Gln
65                  70                  75                  80

Met Asn Ser Leu Arg Ala Glu Asp Thr Ala Val Tyr Tyr Cys Ala Arg
                85                  90                  95

Asp Ser Gly Tyr Ser Asp Pro Met Trp Gly Gln Gly Thr Leu Val Thr
            100                 105                 110

Val Ser Ser
        115
```

<210> SEQ ID NO 19
<211> LENGTH: 333
<212> TYPE: DNA
<213> ORGANISM: Artificial Sequence
<220> FEATURE:
<223> OTHER INFORMATION: Synthesized

<400> SEQUENCE: 19

```
gacgttgtga tgacccagtc tccatcttcc gtgtctgcat ctgtaggaga cagagtcacc      60

atcacctgtc aggccagtca gaacattagg acttacttat cctggtatca gcagaaacca     120

gggaaagccc ctaagctcct gatctatgct gcagccaatc tggcatctgg ggtcccatca     180

aggttcagcg gcagtggatc tgggacagat ttcactctca ccatcagcga cctggagcct     240

ggcgatgctg caacttacta ttgtcagtct acctatcttg gtactgatta tgttggcggt     300

gctttcggcg gagggaccaa ggtggagatc aaa                                  333
```

<210> SEQ ID NO 20
<211> LENGTH: 111
<212> TYPE: PRT
<213> ORGANISM: Artificial Sequence
<220> FEATURE:

```
<223> OTHER INFORMATION: Synthesized

<400> SEQUENCE: 20

Asp Val Val Met Thr Gln Ser Pro Ser Ser Val Ser Ala Ser Val Gly
1               5                   10                  15

Asp Arg Val Thr Ile Thr Cys Gln Ala Ser Gln Asn Ile Arg Thr Tyr
            20                  25                  30

Leu Ser Trp Tyr Gln Gln Lys Pro Gly Lys Ala Pro Lys Leu Leu Ile
        35                  40                  45

Tyr Ala Ala Ala Asn Leu Ala Ser Gly Val Pro Ser Arg Phe Ser Gly
    50                  55                  60

Ser Gly Ser Gly Thr Asp Phe Thr Leu Thr Ile Ser Asp Leu Glu Pro
65                  70                  75                  80

Gly Asp Ala Ala Thr Tyr Tyr Cys Gln Ser Thr Tyr Leu Gly Thr Asp
                85                  90                  95

Tyr Val Gly Gly Ala Phe Gly Gly Gly Thr Lys Val Glu Ile Lys
            100                 105                 110


<210> SEQ ID NO 21
<211> LENGTH: 345
<212> TYPE: DNA
<213> ORGANISM: Artificial Sequence
<220> FEATURE:
<223> OTHER INFORMATION: Synthesized

<400> SEQUENCE: 21

gaggtgcagc tgttggagtc tgggggaggc ttggtacagc ctggggggtc cctgagactc      60

tcctgtgcag cctctggaat cgacttcagt aggagatact acatgtgctg ggtccgccag     120

gctccaggga aggggctgga gtggatcgca tgcatatata ctggtagccg cgatactcct     180

cactacgcga gctccgcgaa aggccggttc accatctcca gagacaattc caagaacacg     240

ctgtatctgc aaatgaacag cctgagagcc gaggacacgg ccgtatatta ctgtgcgaga     300

gaaggtagcc tgtggggcca gggaaccctg gtcaccgtct cgagc                     345


<210> SEQ ID NO 22
<211> LENGTH: 115
<212> TYPE: PRT
<213> ORGANISM: Artificial Sequence
<220> FEATURE:
<223> OTHER INFORMATION: Synthesized

<400> SEQUENCE: 22

Glu Val Gln Leu Leu Glu Ser Gly Gly Gly Leu Val Gln Pro Gly Gly
1               5                   10                  15

Ser Leu Arg Leu Ser Cys Ala Ala Ser Gly Ile Asp Phe Ser Arg Arg
            20                  25                  30

Tyr Tyr Met Cys Trp Val Arg Gln Ala Pro Gly Lys Gly Leu Glu Trp
        35                  40                  45

Ile Ala Cys Ile Tyr Thr Gly Ser Arg Asp Thr Pro His Tyr Ala Ser
    50                  55                  60

Ser Ala Lys Gly Arg Phe Thr Ile Ser Arg Asp Asn Ser Lys Asn Thr
65                  70                  75                  80

Leu Tyr Leu Gln Met Asn Ser Leu Arg Ala Glu Asp Thr Ala Val Tyr
                85                  90                  95

Tyr Cys Ala Arg Glu Gly Ser Leu Trp Gly Gln Gly Thr Leu Val Thr
            100                 105                 110

Val Ser Ser
```

115

<210> SEQ ID NO 23
<211> LENGTH: 333
<212> TYPE: DNA
<213> ORGANISM: Artificial Sequence
<220> FEATURE:
<223> OTHER INFORMATION: Synthesized

<400> SEQUENCE: 23
gacatccaga tgacccagtc tccttccacc ctgtctgcat ctgtaggaga cagagtcacc 60
atcacttgcc agtccagtca gagtgtttat agtaactggt tctcctggta tcagcagaaa 120
ccagggaaag cccctaagct cctgatctat tctgcatcca ctctggcatc tggggtccca 180
tcaaggttca gcggcagtgg atctgggaca gaattcactc tcaccatcag cagcctgcag 240
cctgatgatt ttgcaactta ttactgcgca ggcggttaca atactgttat tgatactttt 300
gctttcggcg gagggaccaa ggtggagatc aaa 333

<210> SEQ ID NO 24
<211> LENGTH: 111
<212> TYPE: PRT
<213> ORGANISM: Artificial Sequence
<220> FEATURE:
<223> OTHER INFORMATION: Synthesized

<400> SEQUENCE: 24

Asp Ile Gln Met Thr Gln Ser Pro Ser Thr Leu Ser Ala Ser Val Gly
1 5 10 15

Asp Arg Val Thr Ile Thr Cys Gln Ser Ser Gln Ser Val Tyr Ser Asn
20 25 30

Trp Phe Ser Trp Tyr Gln Gln Lys Pro Gly Lys Ala Pro Lys Leu Leu
35 40 45

Ile Tyr Ser Ala Ser Thr Leu Ala Ser Gly Val Pro Ser Arg Phe Ser
50 55 60

Gly Ser Gly Ser Gly Thr Glu Phe Thr Leu Thr Ile Ser Ser Leu Gln
65 70 75 80

Pro Asp Asp Phe Ala Thr Tyr Tyr Cys Ala Gly Gly Tyr Asn Thr Val
85 90 95

Ile Asp Thr Phe Ala Phe Gly Gly Gly Thr Lys Val Glu Ile Lys
100 105 110

<210> SEQ ID NO 25
<211> LENGTH: 357
<212> TYPE: DNA
<213> ORGANISM: Artificial Sequence
<220> FEATURE:
<223> OTHER INFORMATION: Synthesized

<400> SEQUENCE: 25
cagtcgctgg tggagtctgg gggaggcttg gtccagcctg gggggtccct gagactctcc 60
tgtactgcct ctggattctc cctcagtagg tactacatga cctgggtccg ccaggctcca 120
gggaaggggc tggagtggat cggaaccatt tatactagtg gtagtacatg gtacgcgagc 180
tggacaaaag gcagattcac catctccaaa gacaatacca agaacacggt ggatcttcaa 240
atgaacagcc tgagagccga ggacacggct gtgtattact gtgcgagatc ctattatggc 300
ggtgataaga ctggtttagg catctggggc cagggaactc tggttaccgt ctcttca 357

<210> SEQ ID NO 26

<211> LENGTH: 119
<212> TYPE: PRT
<213> ORGANISM: Artificial Sequence
<220> FEATURE:
<223> OTHER INFORMATION: Synthesized

<400> SEQUENCE: 26

```
Gln Ser Leu Val Glu Ser Gly Gly Gly Leu Val Gln Pro Gly Gly Ser
1               5                   10                  15

Leu Arg Leu Ser Cys Thr Ala Ser Gly Phe Ser Leu Ser Arg Tyr Tyr
            20                  25                  30

Met Thr Trp Val Arg Gln Ala Pro Gly Lys Gly Leu Glu Trp Ile Gly
        35                  40                  45

Thr Ile Tyr Thr Ser Gly Ser Thr Trp Tyr Ala Ser Trp Thr Lys Gly
    50                  55                  60

Arg Phe Thr Ile Ser Lys Asp Asn Thr Lys Asn Thr Val Asp Leu Gln
65                  70                  75                  80

Met Asn Ser Leu Arg Ala Glu Asp Thr Ala Val Tyr Tyr Cys Ala Arg
                85                  90                  95

Ser Tyr Tyr Gly Gly Asp Lys Thr Gly Leu Gly Ile Trp Gly Gln Gly
            100                 105                 110

Thr Leu Val Thr Val Ser Ser
        115
```

<210> SEQ ID NO 27
<211> LENGTH: 339
<212> TYPE: DNA
<213> ORGANISM: Artificial Sequence
<220> FEATURE:
<223> OTHER INFORMATION: Synthesized

<400> SEQUENCE: 27

```
gacatccaga tgacccagtc tccttccacc ctgtctgcat ctgtaggaga cagagtcacc      60

atcacttgcc aggccagtca gagcattgat agttggttat cctggtatca gcagaaacca     120

gggaaagccc ctaagctcct gatctatcag gcatccactc tggcatctgg ggtcccatca     180

aggttcagcg gcagtggatc tgggacagag ttcactctca ccatcagcag cctgcagcct     240

gatgattttg caacttatta ctgccaatct gcttatggtg ttagtggtac tagtagttat     300

ttatatactt tcggcggagg gaccaaggtg gagatcaaa                            339
```

<210> SEQ ID NO 28
<211> LENGTH: 113
<212> TYPE: PRT
<213> ORGANISM: Artificial Sequence
<220> FEATURE:
<223> OTHER INFORMATION: Synthesized

<400> SEQUENCE: 28

```
Asp Ile Gln Met Thr Gln Ser Pro Ser Thr Leu Ser Ala Ser Val Gly
1               5                   10                  15

Asp Arg Val Thr Ile Thr Cys Gln Ala Ser Gln Ser Ile Asp Ser Trp
            20                  25                  30

Leu Ser Trp Tyr Gln Gln Lys Pro Gly Lys Ala Pro Lys Leu Leu Ile
        35                  40                  45

Tyr Gln Ala Ser Thr Leu Ala Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80
```

```
Asp Asp Phe Ala Thr Tyr Tyr Cys Gln Ser Ala Tyr Gly Val Ser Gly
                85                  90                  95

Thr Ser Ser Tyr Leu Tyr Thr Phe Gly Gly Gly Thr Lys Val Glu Ile
            100                 105                 110

Lys


<210> SEQ ID NO 29
<211> LENGTH: 366
<212> TYPE: DNA
<213> ORGANISM: Artificial Sequence
<220> FEATURE:
<223> OTHER INFORMATION: Synthesized

<400> SEQUENCE: 29

gaggtgcagc tgttggagtc tgggggaggc ttggtacagc ctggggggtc cctgagactc      60

tcctgtgcag cctctggatt caccatcagt cgctaccaca tgacttgggt ccgccaggct     120

ccagggaagg ggctggagtg gatcggacat atttatgtta ataatgatga cacagactac     180

gcgagctccg cgaaaggccg gttcaccatc tccagagaca attccaagaa cacgctgtat     240

ctgcaaatga acagcctgag agccgaggac acggccacct atttctgtgc gagattggat     300

gttggtggtg gtggtgctta tattggggac atctggggcc agggaactct ggttaccgtc     360

tcttca                                                                366


<210> SEQ ID NO 30
<211> LENGTH: 122
<212> TYPE: PRT
<213> ORGANISM: Artificial Sequence
<220> FEATURE:
<223> OTHER INFORMATION: Synthesized

<400> SEQUENCE: 30

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Ile Ser Arg Tyr
            20                  25                  30

His Met Thr Trp Val Arg Gln Ala Pro Gly Lys Gly Leu Glu Trp Ile
        35                  40                  45

Gly His Ile Tyr Val Asn Asn Asp Asp Thr Asp Tyr Ala Ser Ser Ala
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Thr Tyr Phe Cys
                85                  90                  95

Ala Arg Leu Asp Val Gly Gly Gly Gly Ala Tyr Ile Gly Asp Ile Trp
            100                 105                 110

Gly Gln Gly Thr Leu Val Thr Val Ser Ser
        115                 120


<210> SEQ ID NO 31
<211> LENGTH: 339
<212> TYPE: DNA
<213> ORGANISM: Artificial Sequence
<220> FEATURE:
<223> OTHER INFORMATION: Synthesized

<400> SEQUENCE: 31

gacatccaga tgacccagtc tccatcctcc ctgtctgcat ctgtaggaga cagagtcacc      60

atcacttgcc agtccagtca gagtgtttat aacaacaacg acttagcctg gtatcagcag     120
```

```
aaaccaggga aagttcctaa gctcctgatc tattatgctt ccactctggc atctggggtc    180

ccatctcggt tcagtggcag tggatctggg acagatttca ctctcaccat cagcagcctg    240

cagcctgaag atgttgcaac ttattactgt gcaggcggtt atgatacgga tggtcttgat    300

acgtttgctt tcggcggagg gaccaaggtg gagatcaaa                           339


<210> SEQ ID NO 32
<211> LENGTH: 113
<212> TYPE: PRT
<213> ORGANISM: Artificial Sequence
<220> FEATURE:
<223> OTHER INFORMATION: Synthesized

<400> SEQUENCE: 32

Asp Ile Gln Met Thr Gln Ser Pro Ser Ser Leu Ser Ala Ser Val Gly
1               5                   10                  15

Asp Arg Val Thr Ile Thr Cys Gln Ser Ser Gln Ser Val Tyr Asn Asn
            20                  25                  30

Asn Asp Leu Ala Trp Tyr Gln Gln Lys Pro Gly Lys Val Pro Lys Leu
        35                  40                  45

Leu Ile Tyr Tyr Ala Ser Thr Leu Ala Ser Gly Val Pro Ser Arg Phe
    50                  55                  60

Ser Gly Ser Gly Ser Gly Thr Asp Phe Thr Leu Thr Ile Ser Ser Leu
65                  70                  75                  80

Gln Pro Glu Asp Val Ala Thr Tyr Tyr Cys Ala Gly Gly Tyr Asp Thr
                85                  90                  95

Asp Gly Leu Asp Thr Phe Ala Phe Gly Gly Gly Thr Lys Val Glu Ile
            100                 105                 110

Lys


<210> SEQ ID NO 33
<211> LENGTH: 345
<212> TYPE: DNA
<213> ORGANISM: Artificial Sequence
<220> FEATURE:
<223> OTHER INFORMATION: Synthesized

<400> SEQUENCE: 33

gaggtgcagc tggtggagtc tgggggaggc ttggtccagc ctggggggtc cctgagactc     60

tcctgtactg cctctggatt ctccctcagt agctatgcaa tgagctgggt ccgccaggct    120

ccagggaggg ggctggagtg gatcggaatc atttatgcta gtggtagcac atactacgcg    180

agctcggcga aaggcagatt caccatctcc aaagacaata ccaagaacac ggtggatctt    240

caaatgaaca gcctgagagc cgaggacacg gctgtgtatt actgtgcgag aatttatgac    300

ggcatggacc tctggggcca gggaactctg gttaccgtct cttca                    345


<210> SEQ ID NO 34
<211> LENGTH: 115
<212> TYPE: PRT
<213> ORGANISM: Artificial Sequence
<220> FEATURE:
<223> OTHER INFORMATION: Synthesized

<400> SEQUENCE: 34

Glu Val Gln Leu Val Glu Ser Gly Gly Gly Leu Val Gln Pro Gly Gly
1               5                   10                  15

Ser Leu Arg Leu Ser Cys Thr Ala Ser Gly Phe Ser Leu Ser Ser Tyr
            20                  25                  30
```

```
Ala Met Ser Trp Val Arg Gln Ala Pro Gly Arg Gly Leu Glu Trp Ile
        35                  40                  45

Gly Ile Ile Tyr Ala Ser Gly Ser Thr Tyr Tyr Ala Ser Ser Ala Lys
    50                  55                  60

Gly Arg Phe Thr Ile Ser Lys Asp Asn Thr Lys Asn Thr Val Asp Leu
65                  70                  75                  80

Gln Met Asn Ser Leu Arg Ala Glu Asp Thr Ala Val Tyr Tyr Cys Ala
                85                  90                  95

Arg Ile Tyr Asp Gly Met Asp Leu Trp Gly Gln Gly Thr Leu Val Thr
            100                 105                 110

Val Ser Ser
        115
```

<210> SEQ ID NO 35
<211> LENGTH: 321
<212> TYPE: DNA
<213> ORGANISM: Artificial Sequence
<220> FEATURE:
<223> OTHER INFORMATION: Synthesized

<400> SEQUENCE: 35

```
gacatccaga tgacccagtc tccatcctcc ctgtctgcat ctgtaggaga cagagtcacc     60

atcaattgcc aggccagtca gaacatttac agctacttat cctggtatca gcagaaacca    120

gggaaagttc ctaagcgcct gatctatctg gcatctactc tggcatctgg ggtcccatct    180

cggttcagtg gcagtggatc tgggacagat tacactctca ccatcagcag cctgcagcct    240

gaagatgttg caacttatta ctgtcaaagc aattataacg gtaattatgg tttcggcgga    300

gggaccaagg tggagatcaa a                                              321
```

<210> SEQ ID NO 36
<211> LENGTH: 107
<212> TYPE: PRT
<213> ORGANISM: Artificial Sequence
<220> FEATURE:
<223> OTHER INFORMATION: Synthesized

<400> SEQUENCE: 36

```
Asp Ile Gln Met Thr Gln Ser Pro Ser Ser Leu Ser Ala Ser Val Gly
1               5                   10                  15

Asp Arg Val Thr Ile Asn Cys Gln Ala Ser Gln Asn Ile Tyr Ser Tyr
            20                  25                  30

Leu Ser Trp Tyr Gln Gln Lys Pro Gly Lys Val Pro Lys Arg Leu Ile
        35                  40                  45

Tyr Leu Ala Ser Thr Leu Ala Ser Gly Val Pro Ser Arg Phe Ser Gly
    50                  55                  60

Ser Gly Ser Gly Thr Asp Tyr Thr Leu Thr Ile Ser Ser Leu Gln Pro
65                  70                  75                  80

Glu Asp Val Ala Thr Tyr Tyr Cys Gln Ser Asn Tyr Asn Gly Asn Tyr
                85                  90                  95

Gly Phe Gly Gly Gly Thr Lys Val Glu Ile Lys
            100                 105
```

<210> SEQ ID NO 37
<211> LENGTH: 360
<212> TYPE: DNA
<213> ORGANISM: Artificial Sequence
<220> FEATURE:
<223> OTHER INFORMATION: Synthesized

<400> SEQUENCE: 37

```
gaggtgcagc tggtggagtc tgggggaggc ttggtccagc ctgggggtc cctgagactc     60

tcctgtgcag cctctggatt ctccctcaat aactactgga tgagctgggt ccgccaggct    120

ccagggaagg ggctggagtg gatcggaacc attagtagtg gtgcgtatac atggttcgcc    180

acctgggcga caggcagatt caccatctcc agagacaatt ccaagaacac gctgtatctt    240

caaatgaaca gcctgagagc cgaggacacg gctgtgtatt actgtgcgag atattcttct    300

actactgatt ggacctactt taacatctgg ggccagggaa ctctggttac cgtctcttca    360
```

<210> SEQ ID NO 38
<211> LENGTH: 120
<212> TYPE: PRT
<213> ORGANISM: Artificial Sequence
<220> FEATURE:
<223> OTHER INFORMATION: Synthesized

<400> SEQUENCE: 38

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Ser Leu Asn Asn Tyr
            20                  25                  30

Trp Met Ser Trp Val Arg Gln Ala Pro Gly Lys Gly Leu Glu Trp Ile
        35                  40                  45

Gly Thr Ile Ser Ser Gly Ala Tyr Thr Trp Phe Ala Thr Trp Ala Thr
    50                  55                  60

Gly Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Tyr Cys Ala
                85                  90                  95

Arg Tyr Ser Ser Thr Thr Asp Trp Thr Tyr Phe Asn Ile Trp Gly Gln
            100                 105                 110

Gly Thr Leu Val Thr Val Ser Ser
        115                 120
```

<210> SEQ ID NO 39
<211> LENGTH: 324
<212> TYPE: DNA
<213> ORGANISM: Artificial Sequence
<220> FEATURE:
<223> OTHER INFORMATION: Synthesized

<400> SEQUENCE: 39

```
gacatccaga tgacccagtc tccttccacc ctgtctgcat ctgtaggaga cagagtcacc     60

atcacttgcc aggccagtca gagcattaat aactacttag cctggtatca gcagaaacca    120

gggaaagccc ctaagctcct gatctatagg gcatccactc tggaatctgg ggtcccatca    180

aggttcagcg gcagtggatc tgggacagaa ttcactctca ccatcagcag cctgcagcct    240

gatgattttg caacttatta ctgccaaagc tataatggtg ttggtaggac tgctttcggc    300

ggagggacca aggtggagat caaa                                           324
```

<210> SEQ ID NO 40
<211> LENGTH: 108
<212> TYPE: PRT
<213> ORGANISM: Artificial Sequence
<220> FEATURE:
<223> OTHER INFORMATION: Synthesized

<400> SEQUENCE: 40

```
Asp Ile Gln Met Thr Gln Ser Pro Ser Thr Leu Ser Ala Ser Val Gly
1               5                   10                  15

Asp Arg Val Thr Ile Thr Cys Gln Ala Ser Gln Ser Ile Asn Asn Tyr
            20                  25                  30

Leu Ala Trp Tyr Gln Gln Lys Pro Gly Lys Ala Pro Lys Leu Leu Ile
        35                  40                  45

Tyr Arg Ala Ser Thr Leu Glu Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Asp Asp Phe Ala Thr Tyr Tyr Cys Gln Ser Tyr Asn Gly Val Gly Arg
                85                  90                  95

Thr Ala Phe Gly Gly Gly Thr Lys Val Glu Ile Lys
            100                 105
```

<210> SEQ ID NO 41
<211> LENGTH: 354
<212> TYPE: DNA
<213> ORGANISM: Artificial Sequence
<220> FEATURE:
<223> OTHER INFORMATION: Synthesized

<400> SEQUENCE: 41

```
gaggtgaagc tggatgagac tggaggaggc ttggtgcaac ctgggaggcc catgaaactc      60

tcctgtgttg cctctggatt cacttttagt gactactgga tgaactgggt ccgccagtct     120

ccagagaaag gactggagtg ggtagcacaa attagaaaca aaccttataa ttatgaaaca     180

tattattcag attctgtgaa aggcagattc accatctcaa gagatgattc caaaagtagt     240

gtctacctgc aaatgaacaa cttaagagtt gaagacatgg gtatctatta ctgtacgggt     300

tcttactatg gtatggacta ctggggtcaa ggaacctcag tcaccgtctc ctca           354
```

<210> SEQ ID NO 42
<211> LENGTH: 118
<212> TYPE: PRT
<213> ORGANISM: Artificial Sequence
<220> FEATURE:
<223> OTHER INFORMATION: Synthesized

<400> SEQUENCE: 42

```
Glu Val Lys Leu Asp Glu Thr Gly Gly Gly Leu Val Gln Pro Gly Arg
1               5                   10                  15

Pro Met Lys Leu Ser Cys Val Ala Ser Gly Phe Thr Phe Ser Asp Tyr
            20                  25                  30

Trp Met Asn Trp Val Arg Gln Ser Pro Glu Lys Gly Leu Glu Trp Val
        35                  40                  45

Ala Gln Ile Arg Asn Lys Pro Tyr Asn Tyr Glu Thr Tyr Tyr Ser Asp
    50                  55                  60

Ser Val Lys Gly Arg Phe Thr Ile Ser Arg Asp Asp Ser Lys Ser Ser
65                  70                  75                  80

Val Tyr Leu Gln Met Asn Asn Leu Arg Val Glu Asp Met Gly Ile Tyr
                85                  90                  95

Tyr Cys Thr Gly Ser Tyr Tyr Gly Met Asp Tyr Trp Gly Gln Gly Thr
            100                 105                 110

Ser Val Thr Val Ser Ser
        115
```

<210> SEQ ID NO 43
<211> LENGTH: 336
<212> TYPE: DNA
<213> ORGANISM: Artificial Sequence
<220> FEATURE:
<223> OTHER INFORMATION: Synthesized

<400> SEQUENCE: 43

```
gatgtcgtga tgacccaaac tccactctcc ctgcctgtca gtcttggaga tcaagcctcc     60

atctcttgca gatctagtca gagccttgta cacagtaatg gaaacaccta tttacgttgg    120

tacctgcaga agccaggcca gtctccaaag gtcctgatct acaaagtttc caaccgattt    180

tctggggtcc cagacaggtt cagtggcagt ggatcaggga cagatttcac actcaagatc    240

agcagagtgg aggctgagga tctgggagtt tatttctgct ctcaaagtac acatgttccg    300

tggacgttcg gtggaggcac caagctggaa atcaaa                              336
```

<210> SEQ ID NO 44
<211> LENGTH: 112
<212> TYPE: PRT
<213> ORGANISM: Artificial Sequence
<220> FEATURE:
<223> OTHER INFORMATION: Synthesized

<400> SEQUENCE: 44

```
Asp Val Val Met Thr Gln Thr Pro Leu Ser Leu Pro Val Ser Leu Gly
1               5                   10                  15

Asp Gln Ala Ser Ile Ser Cys Arg Ser Ser Gln Ser Leu Val His Ser
            20                  25                  30

Asn Gly Asn Thr Tyr Leu Arg Trp Tyr Leu Gln Lys Pro Gly Gln Ser
        35                  40                  45

Pro Lys Val Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Phe Cys Ser Gln Ser
                85                  90                  95

Thr His Val Pro Trp Thr Phe Gly Gly Gly Thr Lys Leu Glu Ile Lys
            100                 105                 110
```

<210> SEQ ID NO 45
<211> LENGTH: 987
<212> TYPE: DNA
<213> ORGANISM: Artificial Sequence
<220> FEATURE:
<223> OTHER INFORMATION: Synthesized

<400> SEQUENCE: 45

```
gctagcacca agggcccatc ggtcttcccc ctggcaccct cctccaagag cacctctggg     60

ggcacagcgg ccctgggctg cctggtcaag gactacttcc ccgaaccggt gacggtgtcg    120

tggaactcag gcgccctgac cagcggcgtg cacaccttcc cggctgtcct acagtcctca    180

ggactctact ccctcagcag cgtggtgacc gtgccctcca gcagcttggg cacccagacc    240

tacatctgca acgtgaatca caagcccagc aacaccaagg tggacaagag agttgagccc    300

aaatcttgtg acaaaactca cacatgccca ccgtgcccag cacctgaagc cgcgggggca    360

ccgtcagtct tcctcttccc cccaaaaccc aaggacaccc tcatgatctc ccggacccct    420

gaggtcacat gcgtggtggt ggacgtgagc cacgaagacc ctgaggtcaa gttcaactgg    480
```

```
tacgtggacg gcgtggaggt gcataatgcc aagacaaagc cgcgggagga gcagtacaac    540

agcacgtacc gtgtggtcag cgtcctcacc gtcctgcacc aggactggct gaatggcaag    600

gagtacaagt gcgcggtctc caacaaagcc ctcccagccc ccatcgagaa aaccatctcc    660

aaagccaaag ggcagccccg agaaccacag gtgtacaccc tgcccccatc ccgggatgag    720

ctgaccaaga accaggtcag cctgacctgc ctggtcaaag gcttctatcc cagcgacatc    780

gccgtggagt gggagagcaa tgggcagccg gagaacaact acaagaccac gcctcccgtg    840

ctggactccg acggctcctt cttcctctat agcaagctca ccgtggacaa gagcaggtgg    900

cagcagggga acgtcttctc atgctccgtg atgcatgagg ctctgcacaa ccactacacg    960

cagaagagcc tctccctgtc tccgggt                                        987
```

<210> SEQ ID NO 46
<211> LENGTH: 329
<212> TYPE: PRT
<213> ORGANISM: Artificial Sequence
<220> FEATURE:
<223> OTHER INFORMATION: Synthesized

<400> SEQUENCE: 46

```
Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Arg Val Glu Pro Lys Ser Cys Asp Lys Thr His Thr Cys Pro Pro Cys
            100                 105                 110

Pro Ala Pro Glu Ala Ala Gly Ala Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Ala Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270
```

```
Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly
                325
```

<210> SEQ ID NO 47
<211> LENGTH: 321
<212> TYPE: DNA
<213> ORGANISM: Artificial Sequence
<220> FEATURE:
<223> OTHER INFORMATION: Synthesized

<400> SEQUENCE: 47

```
cgtacggtgg ctgcaccatc tgtcttcatc ttcccgccat ctgatgagca gttgaaatct     60

ggaactgcct ctgttgtgtg cctgctgaat aacttctatc ccagagaggc caaagtacag    120

tggaaggtgg ataacgccct ccaatcgggt aactcccagg agagtgtcac agagcaggac    180

agcaaggaca gcacctacag cctcagcagc accctgacgc tgagcaaagc agactacgag    240

aaacacaaag tctacgcctg cgaagtcacc catcagggcc tgagctcgcc cgtcacaaag    300

agcttcaaca ggggagagtg t                                               321
```

<210> SEQ ID NO 48
<211> LENGTH: 107
<212> TYPE: PRT
<213> ORGANISM: Artificial Sequence
<220> FEATURE:
<223> OTHER INFORMATION: Synthesized

<400> SEQUENCE: 48

```
Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
        35                  40                  45

Ser Gly Asn Ser Gln Glu Ser Val Thr Glu Gln Asp Ser Lys Asp Ser
    50                  55                  60

Thr Tyr Ser Leu Ser Ser Thr Leu Thr Leu Ser Lys Ala Asp Tyr Glu
65                  70                  75                  80

Lys His Lys Val Tyr Ala Cys Glu Val Thr His Gln Gly Leu Ser Ser
                85                  90                  95

Pro Val Thr Lys Ser Phe Asn Arg Gly Glu Cys
            100                 105
```

<210> SEQ ID NO 49
<211> LENGTH: 3681
<212> TYPE: DNA
<213> ORGANISM: Artificial Sequence
<220> FEATURE:
<223> OTHER INFORMATION: Synthesized

<400> SEQUENCE: 49

```
gacatccaga tgacccagtc tccttccacc ctgtctgcat ctgtaggaga cagagtcacc     60

atcacttgcc agtccagtca gagtgtttat agtaactggt tctcctggta tcagcagaaa    120
```

```
ccagggaaag cccctaagct cctgatctat tctgcatcca ctctggcatc tggggtccca    180
tcaaggttca gcggcagtgg atctgggaca gaattcactc tcaccatcag cagcctgcag    240
cctgatgatt ttgcaactta ttactgcgca ggcggttaca atactgttat tgatactttt    300
gctttcggcg gagggaccaa ggtggagatc aaaggcggtg gcggtagtgg gggaggcggt    360
tctggcggcg gagggtccgg cggtggagga tcagaggtgc agctgttgga gtctggggga    420
ggcttggtac agcctggggg gtccctgaga ctctcctgtg cagcctctgg aatcgacttc    480
agtaggagat actacatgtg ctgggtccgc caggctccag ggaaggggct ggagtggatc    540
gcatgcatat atactggtag ccgcgatact cctcactacg cgagctccgc gaaaggccgg    600
ttcaccatct ccagagacaa ttccaagaac acgctgtatc tgcaaatgaa cagcctgaga    660
gccgaggaca cggccgtata ttactgtgcg agagaaggta gcctgtgggg ccagggaacc    720
ctggtcaccg tctcgagcgg cggtggaggg tccggcggtg gtggatccca gtcggtggag    780
gagtctgggg gaggcttggt ccagcctggg gggtccctga gactctcctg tacagcctct    840
ggaatcgacc ttaataccta cgacatgatc tgggtccgcc aggctccagg caaggggcta    900
gagtgggttg gaatcattac ttatagtggt agtagatact acgcgaactg ggcgaaaggc    960
cgattcacca tctccaaaga caataccaag aacacggtgt atctgcaaat gaacagcctg   1020
agagctgagg acacggctgt gtattactgt gccagagatt atatgagtgg ttcccacttg   1080
tggggccagg gaaccctggt caccgtctct agtgctagca ccaagggccc atcggtcttc   1140
cccctggcac cctcctccaa gagcacctct gggggcacag cggccctggg ctgcctggtc   1200
aaggactact tccccgaacc ggtgacggtg tcgtggaact caggcgccct gaccagcggc   1260
gtgcacacct tcccggctgt cctacagtcc tcaggactct actccctcag cagcgtggtg   1320
accgtgccct ccagcagctt gggcacccag acctacatct gcaacgtgaa tcacaagccc   1380
agcaacacca aggtggacaa gagagttgag cccaaatctt gtgacaaaac tcacacatgc   1440
ccaccgtgcc cagcacctga agccgcgggg gcaccgtcag tcttcctctt ccccccaaaa   1500
cccaaggaca ccctcatgat ctcccggacc cctgaggtca catgcgtggt ggtggacgtg   1560
agccacgaag accctgaggt caagttcaac tggtacgtgg acggcgtgga ggtgcataat   1620
gccaagacaa agccgcggga ggagcagtac aacagcacgt accgtgtggt cagcgtcctc   1680
accgtcctgc accaggactg gctgaatggc aaggagtaca agtgcgcggt ctccaacaaa   1740
gccctcccag cccccatcga gaaaaccatc tccaaagcca aagggcagcc ccgagaacca   1800
caggtgtata ccctgccccc atcccgggat gagctgacca agaaccaggt cagcctgacc   1860
tgcctggtca aaggcttcta tcccagcgac atcgccgtgg agtgggagag caatgggcag   1920
ccggagaaca actacaagac cacgcctccc gtgctggact ccgacggctc cttcttcctc   1980
tatagcaagc tcaccgtgga caagagcagg tggcagcagg ggaacgtctt ctcatgctcc   2040
gtgatgcatg aggctctgca caaccactac acgcagaaga gcctctccct gtctccgggt   2100
ggcggtggag ggtccggcgg tggtggatcc gaggtgcagc tgttggagtc tgggggaggc   2160
ttggtacagc ctggggggtc cctgagactc tcctgtgcag cctctggatt caccatcagt   2220
cgctaccaca tgacttgggt ccgccaggct ccagggaagg ggctggagtg gatcggacat   2280
atttatgtta ataatgatga cacagactac gcgagctccg cgaaaggccg gttcaccatc   2340
tccagagaca attccaagaa cacgctgtat ctgcaaatga acagcctgag agccgaggac   2400
acggccacct atttctgtgc gagattggat gttggtggtg gtggtgctta tattggggac   2460
atctggggcc agggaactct ggttaccgtc tcttcaggcg gtggcggtag tgggggaggc   2520
```

```
ggttctggcg gcggagggtc cggcggtgga ggatcagaca tccagatgac ccagtctcca   2580

tcctccctgt ctgcatctgt aggagacaga gtcaccatca cttgccagtc cagtcagagt   2640

gtttataaca acaacgactt agcctggtat cagcagaaac cagggaaagt tcctaagctc   2700

ctgatctatt atgcttccac tctggcatct ggggtcccat ctcggttcag tggcagtgga   2760

tctgggacag atttcactct caccatcagc agcctgcagc ctgaagatgt tgcaacttat   2820

tactgtgcag gcggttatga tacggatggt cttgatacgt ttgctttcgg cggagggacc   2880

aaggtggaga tcaaaggcgg tggagggtcc ggcggtggtg gatccgaggt gcagctggtg   2940

gagtctgggg gaggcttggt ccagcctggg gggtccctga gactctcctg tgcagcctct   3000

ggattcacca tcagtaccaa tgcaatgagc tgggtccgcc aggctccagg gaaggggctg   3060

gagtggatcg gagtcattac tggtcgtgat atcacatact acgcgagctg ggcgaaaggc   3120

agattcacca tctccagaga caattccaag aacacgctgt atcttcaaat gaacagcctg   3180

agagccgagg acacggctgt gtattactgt gcgcgcgacg gtggatcatc tgctattact   3240

agtaacaaca tttggggcca aggaactctg gtcaccgttt cttcaggcgg tggcggtagt   3300

gggggaggcg gttctggcgg cggagggtcc ggcggtggag gatcagacgt cgtgatgacc   3360

cagtctcctt ccaccctgtc tgcatctgta ggagacagag tcaccatcaa ttgccaagcc   3420

agtgagagca ttagcagttg gttagcctgg tatcagcaga aaccagggaa agcccctaag   3480

ctcctgatct atgaagcatc caaactggca tctggggtcc catcaaggtt cagcggcagt   3540

ggatctggga cagagttcac tctcaccatc agcagcctgc agcctgatga ttttgcaact   3600

tattactgcc aaggctattt ttattttatt agtcgtactt atgtaaattc tttcggcgga   3660

gggaccaagg tggagatcaa a                                             3681
```

<210> SEQ ID NO 50
<211> LENGTH: 1227
<212> TYPE: PRT
<213> ORGANISM: Artificial Sequence
<220> FEATURE:
<223> OTHER INFORMATION: Synthesized

<400> SEQUENCE: 50

```
Asp Ile Gln Met Thr Gln Ser Pro Ser Thr Leu Ser Ala Ser Val Gly
1               5                   10                  15

Asp Arg Val Thr Ile Thr Cys Gln Ser Ser Gln Ser Val Tyr Ser Asn
            20                  25                  30

Trp Phe Ser Trp Tyr Gln Gln Lys Pro Gly Lys Ala Pro Lys Leu Leu
        35                  40                  45

Ile Tyr Ser Ala Ser Thr Leu Ala Ser Gly Val Pro Ser Arg Phe Ser
    50                  55                  60

Gly Ser Gly Ser Gly Thr Glu Phe Thr Leu Thr Ile Ser Ser Leu Gln
65                  70                  75                  80

Pro Asp Asp Phe Ala Thr Tyr Tyr Cys Ala Gly Gly Tyr Asn Thr Val
                85                  90                  95

Ile Asp Thr Phe Ala Phe Gly Gly Gly Thr Lys Val Glu Ile Lys Gly
            100                 105                 110

Gly Gly Gly Ser Gly Gly Gly Gly Ser Gly Gly Gly Gly Ser Gly Gly
        115                 120                 125

Gly Gly Ser Glu Val Gln Leu Leu Glu Ser Gly Gly Gly Leu Val Gln
    130                 135                 140

Pro Gly Gly Ser Leu Arg Leu Ser Cys Ala Ala Ser Gly Ile Asp Phe
```

```
145                 150                 155                 160

Ser Arg Arg Tyr Tyr Met Cys Trp Val Arg Gln Ala Pro Gly Lys Gly
                165                 170                 175

Leu Glu Trp Ile Ala Cys Ile Tyr Thr Gly Ser Arg Asp Thr Pro His
            180                 185                 190

Tyr Ala Ser Ser Ala Lys Gly Arg Phe Thr Ile Ser Arg Asp Asn Ser
        195                 200                 205

Lys Asn Thr Leu Tyr Leu Gln Met Asn Ser Leu Arg Ala Glu Asp Thr
    210                 215                 220

Ala Val Tyr Tyr Cys Ala Arg Glu Gly Ser Leu Trp Gly Gln Gly Thr
225                 230                 235                 240

Leu Val Thr Val Ser Ser Gly Gly Gly Gly Ser Gly Gly Gly Gly Ser
                245                 250                 255

Gln Ser Val Glu Glu Ser Gly Gly Gly Leu Val Gln Pro Gly Gly Ser
            260                 265                 270

Leu Arg Leu Ser Cys Thr Ala Ser Gly Ile Asp Leu Asn Thr Tyr Asp
        275                 280                 285

Met Ile Trp Val Arg Gln Ala Pro Gly Lys Gly Leu Glu Trp Val Gly
    290                 295                 300

Ile Ile Thr Tyr Ser Gly Ser Arg Tyr Tyr Ala Asn Trp Ala Lys Gly
305                 310                 315                 320

Arg Phe Thr Ile Ser Lys Asp Asn Thr Lys Asn Thr Val Tyr Leu Gln
                325                 330                 335

Met Asn Ser Leu Arg Ala Glu Asp Thr Ala Val Tyr Tyr Cys Ala Arg
            340                 345                 350

Asp Tyr Met Ser Gly Ser His Leu Trp Gly Gln Gly Thr Leu Val Thr
        355                 360                 365

Val Ser Ser Ala Ser Thr Lys Gly Pro Ser Val Phe Pro Leu Ala Pro
    370                 375                 380

Ser Ser Lys Ser Thr Ser Gly Gly Thr Ala Ala Leu Gly Cys Leu Val
385                 390                 395                 400

Lys Asp Tyr Phe Pro Glu Pro Val Thr Val Ser Trp Asn Ser Gly Ala
                405                 410                 415

Leu Thr Ser Gly Val His Thr Phe Pro Ala Val Leu Gln Ser Ser Gly
            420                 425                 430

Leu Tyr Ser Leu Ser Ser Val Val Thr Val Pro Ser Ser Ser Leu Gly
        435                 440                 445

Thr Gln Thr Tyr Ile Cys Asn Val Asn His Lys Pro Ser Asn Thr Lys
    450                 455                 460

Val Asp Lys Arg Val Glu Pro Lys Ser Cys Asp Lys Thr His Thr Cys
465                 470                 475                 480

Pro Pro Cys Pro Ala Pro Glu Ala Ala Gly Ala Pro Ser Val Phe Leu
                485                 490                 495

Phe Pro Pro Lys Pro Lys Asp Thr Leu Met Ile Ser Arg Thr Pro Glu
            500                 505                 510

Val Thr Cys Val Val Val Asp Val Ser His Glu Asp Pro Glu Val Lys
        515                 520                 525

Phe Asn Trp Tyr Val Asp Gly Val Glu Val His Asn Ala Lys Thr Lys
    530                 535                 540

Pro Arg Glu Glu Gln Tyr Asn Ser Thr Tyr Arg Val Val Ser Val Leu
545                 550                 555                 560

Thr Val Leu His Gln Asp Trp Leu Asn Gly Lys Glu Tyr Lys Cys Ala
                565                 570                 575
```

```
Val Ser Asn Lys Ala Leu Pro Ala Pro Ile Glu Lys Thr Ile Ser Lys
            580                 585                 590

Ala Lys Gly Gln Pro Arg Glu Pro Gln Val Tyr Thr Leu Pro Pro Ser
        595                 600                 605

Arg Asp Glu Leu Thr Lys Asn Gln Val Ser Leu Thr Cys Leu Val Lys
    610                 615                 620

Gly Phe Tyr Pro Ser Asp Ile Ala Val Glu Trp Glu Ser Asn Gly Gln
625                 630                 635                 640

Pro Glu Asn Asn Tyr Lys Thr Thr Pro Pro Val Leu Asp Ser Asp Gly
                645                 650                 655

Ser Phe Phe Leu Tyr Ser Lys Leu Thr Val Asp Lys Ser Arg Trp Gln
            660                 665                 670

Gln Gly Asn Val Phe Ser Cys Ser Val Met His Glu Ala Leu His Asn
        675                 680                 685

His Tyr Thr Gln Lys Ser Leu Ser Leu Ser Pro Gly Gly Gly Gly Gly
    690                 695                 700

Ser Gly Gly Gly Gly Ser Glu Val Gln Leu Leu Glu Ser Gly Gly Gly
705                 710                 715                 720

Leu Val Gln Pro Gly Gly Ser Leu Arg Leu Ser Cys Ala Ala Ser Gly
                725                 730                 735

Phe Thr Ile Ser Arg Tyr His Met Thr Trp Val Arg Gln Ala Pro Gly
            740                 745                 750

Lys Gly Leu Glu Trp Ile Gly His Ile Tyr Val Asn Asn Asp Asp Thr
        755                 760                 765

Asp Tyr Ala Ser Ser Ala Lys Gly Arg Phe Thr Ile Ser Arg Asp Asn
    770                 775                 780

Ser Lys Asn Thr Leu Tyr Leu Gln Met Asn Ser Leu Arg Ala Glu Asp
785                 790                 795                 800

Thr Ala Thr Tyr Phe Cys Ala Arg Leu Asp Val Gly Gly Gly Gly Ala
                805                 810                 815

Tyr Ile Gly Asp Ile Trp Gly Gln Gly Thr Leu Val Thr Val Ser Ser
            820                 825                 830

Gly Gly Gly Gly Ser Gly Gly Gly Gly Ser Gly Gly Gly Gly Ser Gly
        835                 840                 845

Gly Gly Gly Ser Asp Ile Gln Met Thr Gln Ser Pro Ser Ser Leu Ser
    850                 855                 860

Ala Ser Val Gly Asp Arg Val Thr Ile Thr Cys Gln Ser Ser Gln Ser
865                 870                 875                 880

Val Tyr Asn Asn Asn Asp Leu Ala Trp Tyr Gln Gln Lys Pro Gly Lys
                885                 890                 895

Val Pro Lys Leu Leu Ile Tyr Tyr Ala Ser Thr Leu Ala Ser Gly Val
            900                 905                 910

Pro Ser Arg Phe Ser Gly Ser Gly Ser Gly Thr Asp Phe Thr Leu Thr
        915                 920                 925

Ile Ser Ser Leu Gln Pro Glu Asp Val Ala Thr Tyr Tyr Cys Ala Gly
    930                 935                 940

Gly Tyr Asp Thr Asp Gly Leu Asp Thr Phe Ala Phe Gly Gly Gly Thr
945                 950                 955                 960

Lys Val Glu Ile Lys Gly Gly Gly Gly Ser Gly Gly Gly Gly Ser Glu
                965                 970                 975

Val Gln Leu Val Glu Ser Gly Gly Gly Leu Val Gln Pro Gly Gly Ser
            980                 985                 990
```

```
Leu Arg Leu Ser Cys Ala Ala Ser  Gly Phe Thr Ile Ser  Thr Asn Ala
        995                 1000                 1005

Met Ser  Trp Val Arg Gln Ala  Pro Gly Lys Gly Leu  Glu Trp Ile
    1010                 1015                 1020

Gly Val  Ile Thr Gly Arg Asp  Ile Thr Tyr Tyr Ala  Ser Trp Ala
    1025                 1030                 1035

Lys Gly  Arg Phe Thr Ile Ser  Arg Asp Asn Ser Lys  Asn Thr Leu
    1040                 1045                 1050

Tyr Leu  Gln Met Asn Ser Leu  Arg Ala Glu Asp Thr  Ala Val Tyr
    1055                 1060                 1065

Tyr Cys  Ala Arg Asp Gly Gly  Ser Ser Ala Ile Thr  Ser Asn Asn
    1070                 1075                 1080

Ile Trp  Gly Gln Gly Thr Leu  Val Thr Val Ser Ser  Gly Gly Gly
    1085                 1090                 1095

Gly Ser  Gly Gly Gly Gly Ser  Gly Gly Gly Gly Ser  Gly Gly Gly
    1100                 1105                 1110

Gly Ser  Asp Val Val Met Thr  Gln Ser Pro Ser Thr  Leu Ser Ala
    1115                 1120                 1125

Ser Val  Gly Asp Arg Val Thr  Ile Asn Cys Gln Ala  Ser Glu Ser
    1130                 1135                 1140

Ile Ser  Ser Trp Leu Ala Trp  Tyr Gln Gln Lys Pro  Gly Lys Ala
    1145                 1150                 1155

Pro Lys  Leu Leu Ile Tyr Glu  Ala Ser Lys Leu Ala  Ser Gly Val
    1160                 1165                 1170

Pro Ser  Arg Phe Ser Gly Ser  Gly Ser Gly Thr Glu  Phe Thr Leu
    1175                 1180                 1185

Thr Ile  Ser Ser Leu Gln Pro  Asp Asp Phe Ala Thr  Tyr Tyr Cys
    1190                 1195                 1200

Gln Gly  Tyr Phe Tyr Phe Ile  Ser Arg Thr Tyr Val  Asn Ser Phe
    1205                 1210                 1215

Gly Gly  Gly Thr Lys Val Glu  Ile Lys
    1220                 1225
```

<210> SEQ ID NO 51
<211> LENGTH: 651
<212> TYPE: DNA
<213> ORGANISM: Artificial Sequence
<220> FEATURE:
<223> OTHER INFORMATION: Synthesized

<400> SEQUENCE: 51

```
gcctatgata tgacccagtc tccatcttcc gtgtctgcat ctgtaggaga cagagtcacc     60

atcaagtgtc aggccagtga ggacatttat agcttcttgg cctggtatca gcagaaacca    120

gggaaagccc ctaagctcct gatccattct gcatcctctc tggcatctgg ggtcccatca    180

aggttcagcg gcagtggatc tgggacagat ttcactctca ccatcagcag cctgcagcct    240

gaagattttg caacttacta ttgtcaacag ggttatggta aaaataatgt tgataatgct    300

ttcggcggag ggaccaaggt ggagatcaaa cgtacggtgg ctgcaccatc tgtcttcatc    360

ttcccgccat ctgatgagca gttgaaatct ggaactgcct ctgttgtgtg cctgctgaat    420

aacttctatc ccagagaggc caaagtacag tggaaggtgg ataacgccct ccaatcgggt    480

aactcccagg agagtgtcac agagcaggac agcaaggaca gcacctacag cctcagcagc    540

accctgacgc tgagcaaagc agactacgag aaacacaaag tctacgcctg cgaagtcacc    600

catcagggcc tgagctcgcc cgtcacaaag agcttcaaca ggggagagtg t             651
```

```
<210> SEQ ID NO 52
<211> LENGTH: 217
<212> TYPE: PRT
<213> ORGANISM: Artificial Sequence
<220> FEATURE:
<223> OTHER INFORMATION: Synthesized

<400> SEQUENCE: 52

Ala Tyr Asp Met Thr Gln Ser Pro Ser Ser Val Ser Ala Ser Val Gly
1               5                   10                  15

Asp Arg Val Thr Ile Lys Cys Gln Ala Ser Glu Asp Ile Tyr Ser Phe
            20                  25                  30

Leu Ala Trp Tyr Gln Gln Lys Pro Gly Lys Ala Pro Lys Leu Leu Ile
        35                  40                  45

His Ser Ala Ser Ser Leu Ala Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Gly Tyr Gly Lys Asn Asn
                85                  90                  95

Val Asp Asn Ala Phe Gly Gly Gly Thr Lys Val Glu Ile Lys Arg Thr
            100                 105                 110

Val Ala Ala Pro Ser Val Phe Ile Phe Pro Pro Ser Asp Glu Gln Leu
        115                 120                 125

Lys Ser Gly Thr Ala Ser Val Val Cys Leu Leu Asn Asn Phe Tyr Pro
    130                 135                 140

Arg Glu Ala Lys Val Gln Trp Lys Val Asp Asn Ala Leu Gln Ser Gly
145                 150                 155                 160

Asn Ser Gln Glu Ser Val Thr Glu Gln Asp Ser Lys Asp Ser Thr Tyr
                165                 170                 175

Ser Leu Ser Ser Thr Leu Thr Leu Ser Lys Ala Asp Tyr Glu Lys His
            180                 185                 190

Lys Val Tyr Ala Cys Glu Val Thr His Gln Gly Leu Ser Ser Pro Val
        195                 200                 205

Thr Lys Ser Phe Asn Arg Gly Glu Cys
    210                 215
```